United States Patent
Pipkin et al.

(10) Patent No.: US 10,864,183 B2
(45) Date of Patent: *Dec. 15, 2020

(54) INJECTABLE NITROGEN MUSTARD COMPOSITIONS COMPRISING A CYCLODEXTRIN DERIVATIVE AND METHODS OF MAKING AND USING THE SAME

(71) Applicant: Cydex Pharmaceuticals, Inc., Lenexa, KS (US)

(72) Inventors: James D. Pipkin, Lawrence, KS (US); Stephen G. Machatha, Overland Park, KS (US)

(73) Assignee: Cydex Pharmaceuticals, Inc., Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,840

(22) Filed: Dec. 27, 2019

(65) Prior Publication Data

US 2020/0268698 A1 Aug. 27, 2020

Related U.S. Application Data

(63) Continuation of application No. 14/229,523, filed on Mar. 28, 2014, which is a continuation-in-part of application No. 14/108,169, filed on Dec. 16, 2013, which is a continuation of application No. 12/790,724, filed on May 28, 2010, now abandoned.

(Continued)

(51) Int. Cl.
*A61K 9/19* (2006.01)
*A61K 47/40* (2006.01)
*A61K 31/198* (2006.01)
*A61K 9/00* (2006.01)

(52) U.S. Cl.
CPC .......... *A61K 31/198* (2013.01); *A61K 9/0019* (2013.01); *A61K 9/19* (2013.01); *A61K 47/40* (2013.01)

(58) Field of Classification Search
None
See application file for complete search history.

(56) References Cited

U.S. PATENT DOCUMENTS 3,032,584 A 5/1962 Bergel et al.
3,032,585 A 5/1962 Bergel et al.
(Continued)

FOREIGN PATENT DOCUMENTS

EP 0317281 5/1989
KR 10-2005-0046776 5/2005
(Continued)

OTHER PUBLICATIONS

Ma et al., New injectable melphalan formulations utilizing (SBE)7m—B—CD or HP—B—CD, International Journal of Pharmaceutics (1999) 189: 227-234, 8 pages. (Year: 1999).*

(Continued)

*Primary Examiner* — Ernst V Arnold
(74) *Attorney, Agent, or Firm* — K&L Gates LLP; Louis C. Cullman; Hal Gibson

(57) ABSTRACT

The present disclosure is directed to pharmaceutical compositions comprising a nitrogen mustard and a cyclodextrin derivative, and methods of making and using the same.

10 Claims, 6 Drawing Sheets

Related U.S. Application Data

(60) Provisional application No. 61/182,560, filed on May 29, 2009.

(56) References Cited

U.S. PATENT DOCUMENTS

| | | |
|---|---|---|
| 4,983,586 A | 1/1991 | Bodor |
| 4,997,651 A | 3/1991 | Poole et al. |
| 5,002,935 A | 3/1991 | Bodor |
| 5,017,566 A | 5/1991 | Bodor |
| 5,024,998 A | 6/1991 | Bodor |
| 5,068,227 A | 11/1991 | Weinshenker |
| 5,134,127 A | 7/1992 | Stella et al. |
| 5,180,716 A | 1/1993 | Yaksh et al. |
| 5,241,059 A | 8/1993 | Yoshinaga |
| 5,324,718 A | 6/1994 | Loftson |
| 5,324,750 A | 6/1994 | Lincoln et al. |
| 5,376,645 A | 12/1994 | Stella et al. |
| 5,407,672 A | 4/1995 | Griffith et al. |
| 5,446,030 A | 8/1995 | Weisz et al. |
| 5,472,954 A | 12/1995 | Loftsson |
| 5,486,508 A | 1/1996 | Uda et al. |
| 5,523,084 A | 6/1996 | Bigner et al. |
| 5,602,112 A | 2/1997 | Rubinfeld |
| 5,646,131 A | 7/1997 | Badwan et al. |
| 5,718,905 A | 2/1998 | Skiba et al. |
| 5,759,573 A | 6/1998 | Kim |
| 5,760,015 A | 6/1998 | Joullie et al. |
| 5,770,222 A | 6/1998 | Unger et al. |
| 5,773,029 A | 6/1998 | Chiesi et al. |
| 5,804,568 A | 9/1998 | Rubinfeld |
| 5,846,954 A | 12/1998 | Joullie et al. |
| 5,855,916 A | 1/1999 | Chiesi et al. |
| 5,874,418 A | 2/1999 | Stella et al. |
| 5,925,669 A | 7/1999 | Katz et al. |
| 5,935,941 A | 8/1999 | Pitha |
| 6,046,177 A | 4/2000 | Stella et al. |
| 6,048,736 A | 4/2000 | Kosak |
| 6,048,845 A | 4/2000 | Rubinfeld |
| 6,133,248 A | 10/2000 | Stella |
| 6,153,746 A | 11/2000 | Shah et al. |
| 6,204,256 B1 | 3/2001 | Shalaby et al. |
| 6,218,374 B1 | 4/2001 | Rubinfeld |
| 6,284,747 B1 | 9/2001 | Rubinfeld |
| 6,407,079 B1 | 6/2002 | Muller et al. |
| 6,495,160 B2 | 12/2002 | Esposito et al. |
| 6,537,585 B1 | 3/2003 | Dang et al. |
| 6,576,261 B1 | 6/2003 | Pitha |
| 6,583,125 B2 | 6/2003 | Rubinfeld |
| 6,602,860 B1 | 8/2003 | Pitha |
| 6,699,505 B2 | 3/2004 | Shastri et al. |
| 6,780,324 B2 | 8/2004 | Le Garrec et al. |
| 6,881,421 B1 | 4/2005 | da Silveira et al. |
| 6,916,788 B2 | 7/2005 | Seo et al. |
| 7,034,013 B2 | 4/2006 | Thompson et al. |
| 7,115,586 B2 | 10/2006 | Loftsson |
| 7,214,663 B2 | 5/2007 | Bebbington et al. |
| 7,229,645 B2 | 6/2007 | Maa et al. |
| 7,229,841 B2 | 6/2007 | Tamarkin et al. |
| 7,629,331 B2 | 12/2009 | Pipkin et al. |
| 7,635,773 B2 | 12/2009 | Antle |
| 2002/0142953 A1 | 10/2002 | Ballinger et al. |
| 2003/0073665 A1 | 4/2003 | Thompson et al. |
| 2003/0087961 A1 | 5/2003 | Ko et al. |
| 2003/0119761 A1 | 6/2003 | Christian |
| 2003/0162721 A1 | 8/2003 | Mehlem |
| 2004/0091541 A1 | 5/2004 | Unger |
| 2004/0109888 A1 | 6/2004 | Pun et al. |
| 2005/0004074 A1 | 1/2005 | Lyons et al. |
| 2005/0186267 A1 | 8/2005 | Thompson et al. |
| 2005/0215520 A1 | 9/2005 | Liu et al. |
| 2005/0276841 A1 | 12/2005 | Davis et al. |
| 2006/0105045 A1 | 5/2006 | Buchanan et al. |
| 2006/0128611 A1 | 6/2006 | Lewis et al. |
| 2006/0128645 A1 | 6/2006 | Ozawa et al. |
| 2006/0189547 A1 | 8/2006 | Christian |
| 2007/0031402 A1 | 2/2007 | Zhang et al. |
| 2007/0116729 A1 | 5/2007 | Palepu |
| 2008/0085882 A1 | 4/2008 | Siede et al. |
| 2009/0012042 A1 | 1/2009 | Ren et al. |
| 2010/0311838 A1 | 12/2010 | Pipkin et al. |
| 2014/0213650 A1 | 7/2014 | Pipkin et al. |
| 2014/0221488 A1 | 8/2014 | Pipkin et al. |

FOREIGN PATENT DOCUMENTS

| | | |
|---|---|---|
| WO | 1991/004026 | 4/1991 |
| WO | 1991/013100 | 9/1991 |
| WO | 1993/017711 | 9/1993 |
| WO | 2003/033025 | 4/2003 |
| WO | 2003/043602 | 5/2003 |
| WO | 2004/024126 | 3/2004 |
| WO | 2005/117911 | 12/2005 |
| WO | 2006/063154 | 6/2006 |
| WO | 2008/067027 | 6/2008 |
| WO | 2009/018069 | 2/2009 |
| WO | 2009/150278 | 12/2009 |
| WO | 2010/138920 | 12/2010 |

OTHER PUBLICATIONS

Alkeran® (prescribing information for injection 2002, 11 pages). (Year: 2002).*

Chang et al. (J Pharm Pharmacol. 1979,31:853-854). (Year: 1979).*

Kang et al. (European Journal of Pharmaceutical Sciences 2002;15:163-170) (Year: 2002).*

Alkeran® (melphalan hydrochloride) for Injection, Prescribing Information, GlaxoSmithKline, United States, 9 pages (Mar. 2008).

Brewster et al., Effect of various cyclodextrins on solution stability and dissolution rate of doxorubicin hydrochloride. Int. J. Pharm. 79:289-299, Elsevier Science Publishers B.V., Netherlands (1992).

Charman et al., Alteration of the intravenous pharmacokinetics of a synthetic ozonide antimalarial in the presence of a modified cyclodextrin. J. Pharm. Sci. 95:256-267, Wiley-Liss, Inc. and the American Pharmacists Assoc., United States (2006).

Ganguly et al., Mathematical model for the chemotherapeutic drug efficacy in arresting tumor growth based on the cancer stem cell hypothesis. Cell Prolif. 40:338-354, Blackwell Publishing, Ltd., United Kingdom (2007).

Green, A.R., The effects of dimethyl-β-cyclodextrin and related compounds on the physical and chemical properties of chlorambucil and melphalan. Dissertations Abstracts International 50:1427-B, ProQuest LLC, United States, 1 page (1989).

International Search Report for International Application No. PCT/US2010/036736 dated Aug. 4, 2010, ISA/US, Alexandria, VA.

Lazarus et al., High-dose melphalan and the development of hematopoietic stem-cell transplantation: 25 years later. J. Clin. Oncol. 26:2240-2243, American Society of Clinical Oncology, United States (May 2008).

Loftsson et al, The effects of 2-hydroxypropyl-β-cyclodextrin on the solubility and stability of chlorambucil and melphalan in aqueous solution. Int. J. Pharm. 57:63-72, Elsevier, Netherlands (1989).

Loftsson et al., Comparative study on inclusion complexation of acetylsalicylic acid, cholecalciferol and melphalan with β- and γ-cyclodextrin and some of their derivatives. Acta Pharm. Nord. 2:303-312, Swedish Pharmaceutical Press, Sweden (1990).

Lokich et al., Dose intensity for bolus versus infusion chemotherapy administration: Review of the literature for 27 anti-neoplastic agents. Ann. Oncol. 8:15-25, Kluwer Academic Publishers, United Kingdom (1997).

Ma et al., Application Process of Cyclodextrin in Drugs and Pharmaceutical Analysis, Journal of Yanan University, vol. 17, No. 2, Jun. 1998.

Ma et al., Comparative effects of (SBE)7m-β-CD or HP-β-CD on stability of two anti-neoplastic agents, melphalan and carmustine. J. Pharm. Sci. 89:275-287, Wiley-Liss, Inc. and the American Pharmacists Assoc, United States (2000).

Ma et al, New injectable melphalan formulations utilizing (Sbe)7m-β-CD or HP-β-CD. Int. J. Pharm. 189:227-234, Elsevier, Netherlands (1999).

(56) References Cited

OTHER PUBLICATIONS

Medlicott et al., Comparison of the effects of potential parenteral vehicles for poorly water soluble anticancer drugs (organic cosolvents and cyclodextrin solutions) on cultured endothelial cells (HUV-EC). J. Pharm. Sci., 87:1138-1143, American Chemical Society and American Pharmaceutical Assoc., United States (1998).

Mougenot et al., In vitro cytotoxic effect of melphalan and pilot phase II study in hormone-refractory prostate cancer. Anticancer Res. 26:2197-2204, Potamitis Press, Greece (2006).

Mougenot et al., Population pharmacokinetics of melphalan, infused over a 24 hour period, in patients with advanced malignancies. Cancer Chemother. Pharmacol. 53:503-512, Springer-Verlag, Germany (2004).

Nath et al., Population pharmacokinetics of melphalan in patients with multiple myeloma undergoing high dose therapy. Br. J. Clin. Pharmacol. 69:484-497, The British Pharmacological Society, United Kingdom (Feb. 2010).

Norda et al., Pharmacokinetics of melphalan in isolated limb perfusion. Cancer Chemother. Pharmacol. 1999, 43: 35-42.

Oh et al., Comparison of microvessel density before and after peripheral blood stem cell transplantation in multiple myeloma patients and its clinical implications: multicenter trial. International Journal of Hematology, 76, 2002: 465-470.

Pinguet et al., Influence of the schedule of exposure on the cytotoxic effect of melphalan on human 8226 and A2780 cells. Eur. J. Cancer 35:1402-1406, Elsevier, United Kingdom (1999).

Stella et al., Mechanisms of drug release from cyclodextrin complexes. Adv. Drug. Del. Rev. 36:3-16, Elsevier, Netherlands (1999).

Stout et al., The hydrolysis of L-phenylalanine mustard (melphalan). Int. J. Pharm. 24:193-208, Elsevier, Netherlands (1985).

Wood et al., Reduction of tumour intracellular pH and enhancement of melphalan cytotoxicity by the ionophore nigericin. Int. J. Cancer, 60, 264-268 (1995).

Written Opinion for International Application No. PCT/US2010/036736 dated Aug. 4, 2010, ISA.US, Alexandria, AV.

Iyakuhin-Tenkabutu-Jiten 2007, Yakuji-nipposha, Jul. 25, 2007, p. 253 the section of "povidone."

Nihon Iyakuhin Shu, Iryoyaku 2009th Edition, Jiho Inc., Sep. 1, 2008, p. 2586-2589 the section of "melphalan."

Pan Xuemei et al., Application Progress of Hydroxypropyl-β-cyclodextrin and Sulfobutyl ether-β-cyclodextrin, Tianjin Pharmacy, vol. 17, No. 5, p. 59-61, Oct. 2005.

Halls (Halls.md, Body Surface Area Calculator for medication doses [Retrieved from internet <URL: http://halls.md/body-surfacearea/bsa.htm >], 2014).

Perfusion (Perfusion.com, Isolated Limb Perfusion: An Overview (Sep. 1, 2004) [Retrieved from internet <URL: http://www.perfusion.com/cgi-bin/absolutenm/templates/articledisplay.asp?articleid=1552#.VZ7nik3bLDA >], 2 pages).

UConn (UConn Health, UConn Musculoskeletal Institute, Bone Tumors and Oncology Conditions and Treatments, Benign and Malignant Bone Tumors [Retrieved from Internet <URL: http://nemsi.uchc.edu/clinical_services/orthopaedic/bonetumors/bonetumors.html >], 5 pages.).

Alkeran® (melphalan hydrochloride) for Injection, Prescribing Information, 2002, 11 pages, GlaxoSmithKline.

Arima et al., Comparative Studies of the Enhancing Effects of Cyclodextrins on the Solubility and Oral Bioavailability of Tacrolimus in Rats, Journal of Pharmaceutical Sciencs, vol. 90, No. 6, pp. 690-701 (2001).

Bosanquet, Stability of solutions of antineoplastic agents during preparation and storage for in vitro assays. Cancer Chemotherapy and Pharmacology, 14:83-95 (1985).

Bousanquet, Stability of melphalan solutions during preparation nd staorage. Journal of Pharmaceutical Sciences, vol. 74, No. 3, pp. 348-351 (1985).

Cancer Network, Consider High-Dose Melphalan as Standard Conditioning for Multiple Myeloma, vol. 9(2), 3 pp. (2000).

Challa et al., Cyclodextrins in Drug Delivery: An Updated Review. AAPS PharmSciTech, 6(2):E329-E357, Article 43 (2005).

Cutrignelli et al., Comparative effects of some hydrophilic excipients on the rate of gabapentin and baclofen lactamization in lyophilized formulations, International Journal of Pharmaceutics 332, pp. 98-106 (2007).

Gidwani et al., Review Article: A Comprehensive Review on Cyclodextrin-Based Carriers for Delivery of Chemotherapeutic Cytotoxic Anticancer Drugs. Hindawi Publishing Coporation, BioMed Research International, vol. 2015 Article ID 198268, 15 pages (2015).

Hara et al., Double-conditioning regimens consisting of thiotepa, melphalan and busulfan with stem cell rescue for the treatment of pediatric solid tumors. Bone Marrow Transplantation, 22:7-12 (1998).

Hong et al.' Effect of Cyclodextrin Derivation and Amorphous State of Complex on Accelerated Degradation of Ziprasidone, Journal of Pharmaceutical Sciences, vol. 100, No. 7, pp. 2703-2715 (2011).

Loftsson et al., Cyclodextrin-accelerated degradation of beta-lactam antibiotics in aqueous solutions, International Journal of Pharmaceutics 67, pp. R5-R7 (1991).

Loftsson et al., Pharmaceutical applications of cyclodextrins. 1. Drug solubilization and stabilization. Journal of Pharmaceutical Sciences, vol. 85, No. 10, pp. 1017-1025 (1996).

Rajewski et al., Preliminary safety evaluation of parenterally administered sulfoalkyl ether b-cyclodextrin derivatives. Abstract. J. Pharm. Sci. 84(8), pp. 927-932 (1995).

Teshima et al., Effects of Cyclodextrins on Degradations of Emetine and Cephaeline in Aqueous Solution, Chem. & Pharm Bull, vol. 37, No. 6, pp. 1591-1594 (1989).

* cited by examiner

INJECTABLE NITROGEN MUSTARD COMPOSITIONS COMPRISING A CYCLODEXTRIN DERIVATIVE AND METHODS OF MAKING AND USING THE SAME

CROSS-REFERENCE TO RELATED APPLICATIONS

This application is a continuation of U.S. patent application Ser. No. 14/229,523, filed Mar. 28, 2014, which is a continuation-in-part of U.S. patent application Ser. No. 14/108,169, filed Dec. 16, 2013, which is a continuation of U.S. patent application Ser. No. 12/790,724, filed May 28, 2010, which claims the benefit of the filing date of U.S. Appl. No. 61/182,560, filed May 29, 2009, all of which are incorporated herein by reference in their entirety.

BACKGROUND

Field

The present embodiments relate to pharmaceutical compositions comprising a nitrogen mustard, such as melphalan, mechlorethamine, cyclophosphamide, ifosfamide, bendamustine, etc., and a cyclodextrin derivative, and methods of making and using the same, for example, to treat disorders and diseases that are therapeutically responsive to the nitrogen mustard.

BACKGROUND

Melphalan is an alkylating agent of the bischloroethylamine type, and is active against both resting and rapidly dividing tumor cells. An injectable melphalan composition (ALKERAN® for Injection, GlaxoSmithKline) has been approved by the U.S. Food and Drug Administration for the palliative treatment of patients with multiple myeloma for whom oral therapy is not appropriate, and an oral melphalan composition (ALKERAN® Tablets, GlaxoSmithKline) has been approved for the palliative treatment of multiple myeloma and for the palliation of non-resectable epithelial carcinoma of the ovary.

ALKERAN® for Injection (GlaxoSmithKline) is administered intravenously after first diluting a sterile, nonpyrogenic, freeze-dried powder containing melphalan hydrochloride (equivalent to 50 mg melphalan) and 20 mg povidone with a sterile diluent that contains sodium citrate (0.2 g), propylene glycol (6 mL), ethanol (96%, 0.52 mL), and water, for a total volume of 10 mL. The usual intravenous dose is 16 mg/m$^2$, which is administered as a single infusion over 15 to 20 minutes. Melphalan is intravenously administered in 4 doses at 2-week intervals, then, after adequate recovery from toxicity, at 4-week intervals.

According to the ALKERAN® for Injection (GlaxoSmithKline) label, following administration of ALKERAN® for Injection, drug plasma concentrations of melphalan decline rapidly in a biexponential manner with distribution phase and terminal elimination phase half-lives of approximately 10 and 75 minutes, respectively. The average total body clearance is 7 to 9 mL/min/kg (250 to 325 mL/min/m$^2$). A study has reported that on repeat dosing of 0.5 mg/kg every 6 weeks, the clearance of melphalan decreased from 8.1 mL/min/kg after the first course, to 5.5 mL/min/kg after the third course, but did not decrease appreciably after the third course. Mean (±SD) peak melphalan plasma concentrations in myeloma patients after administration of 10 or 20 mg/m$^2$ doses of melphalan were 1.2±0.4 and 2.8±1.9 μg/mL, respectively. After intravenous administration of 50 mg of melphalan, the steady-state volume of distribution of melphalan is 0.5 L/kg. The extent of melphalan binding to plasma proteins ranges from 60% to 90%. Serum albumin is the major binding protein, while $\alpha_1$-acid glycoprotein appears to account for about 20% of the plasma protein binding. Approximately 30% of the drug is (covalently) irreversibly bound to plasma proteins. Interactions with immunoglobulins have been found to be negligible.

Melphalan is eliminated from plasma primarily by chemical hydrolysis to monohydroxymelphalan and dihydroxymelphalan. Aside from these hydrolysis products, no other melphalan metabolites have been observed in humans.

Controlled trials comparing intravenous to oral melphalan have shown greater myelosuppression with the intravenously administered melphalan. Furthermore, hypersensitivity reactions, including anaphylaxis, have occurred in approximately 2% of patients who have received intravenous melphalan. Melphalan also undergoes rapid hydrolysis in aqueous solution. Melphalan in the ALKERAN® For Injection (GlaxoSmithKline) product also rapidly forms a citrate derivative upon reconstitution and cannot be refrigerated due to precipitation of melphalan from solution.

Melphalan compositions comprising a cyclodextrin derivative as a carrier and/or a diluent are known.

BRIEF SUMMARY

What may be useful is a melphalan formulation that can minimize the toxicology and side-effect profile of intravenous melphalan. What may also be useful is an intravenous melphalan formulation having increased bioavailability and/or an improved rate of therapeutic onset. Also potentially useful is a melphalan composition suitable for intravenous administration that is stable under ambient and/or refrigerated conditions, and can provide fully dissolved melphalan without the need for organic solubilizers (e.g., ethanol and/or propylene glycol, and the like). What may also be helpful is a composition free from components that rapidly form a derivative with melphalan. What may also be helpful is a melphalan composition suitable for intravenous administration that has improved stability, thereby enabling longer duration infusions, and lengthening the melphalan exposure time that a patient receives from a single, convenient administration. As described herein, compositions suitable for oral or parenteral administration that include melphalan and a cyclodextrin derivative have been developed.

Some embodiments include a pharmaceutical composition comprising 25 mg to 125 mg of a nitrogen mustard, such as melphalan, mechlorethamine, cyclophosphamide, ifosfamide, bendamustine, etc., as a hydrochloride salt, an optional buffer, and a cyclodextrin derivative of formula I:

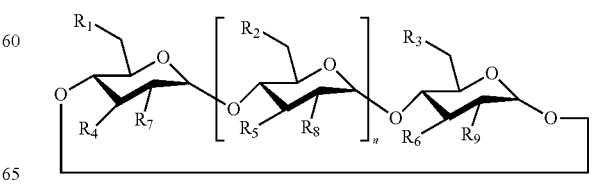

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the pharmaceutical composition has a pH of about 4 to about 6. In some embodiments, the nitrogen mustard comprises melphalan wherein dilution of the pharmaceutical composition with an aqueous solution provides a melphalan solution ready for infusion in which the melphalan degrades by 2% or less at about 25° C. within 5 hours, or 4% or less at about 25° C. within 10 hours after the dilution; and wherein the cyclodextrin derivative is present in a ratio of 50:1 to 100:1 (w/w) relative to the melphalan.

Some embodiments include pharmaceutical composition comprising 150 mg, to 250 mg of a nitrogen mustard, such as melphalan, mechlorethamine, cyclophosphamide, ifosfamide, bendamustine, etc., as a hydrochloride salt, an optional buffer, and a cyclodextrin derivative of formula I:

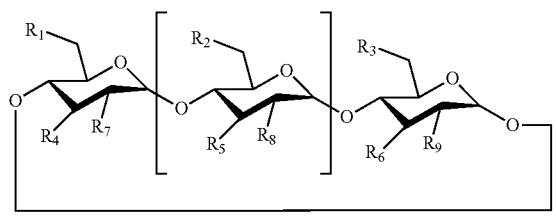

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the pharmaceutical composition has a pH of about 4 to about 6. In some embodiments, the nitrogen mustard comprises melphalan, wherein dilution of the pharmaceutical composition with an aqueous solution provides a melphalan solution ready for infusion in which the melphalan degrades by 2% or less at about 25° C. within 5 hours, or 4% or less at about 25° C. within 10 hours after the dilution, and wherein the cyclodextrin derivative is present in a ratio of 25:1 to 35:1 (w/w) relative to the melphalan.

In some embodiments, the cyclodextrin derivative is a compound of formula II:

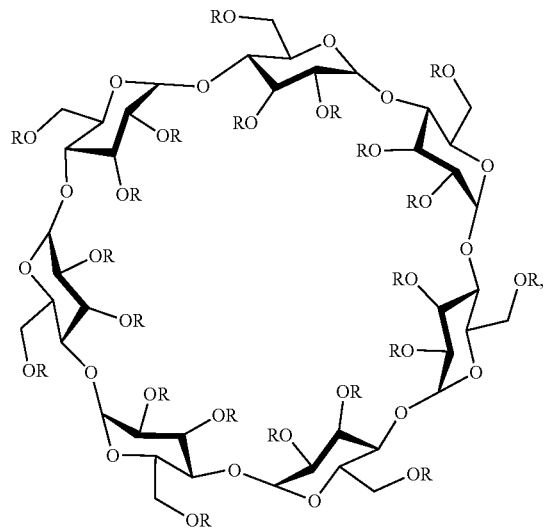

wherein 21-x of the R groups are H and x of the R groups are —$(CH_2)_4^-$ $SO_3^-Na^+$, and x=6.0-7.1.

In some embodiments, the cyclodextrin derivative is a compound of formula II:

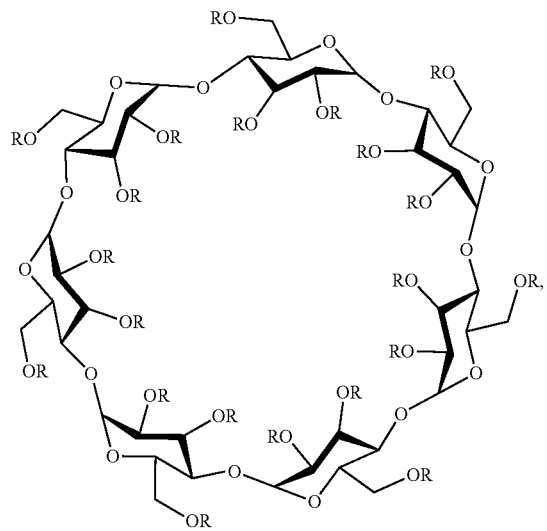

wherein 21-x of the R groups are H and x of the R groups are —$(CH_2)_4^-SO_3^-Na^+$, and x=6.0-7.1; and
    the pharmaceutical composition comprises about 50 mg of melphalan as a hydrochloride salt and the cyclodextrin derivative is present in a concentration of 50:1 to 100:1 (w/w) relative to the melphalan; or
    the pharmaceutical composition comprises about 50 mg of melphalan as a hydrochloride salt the cyclodextrin derivative is present in a ratio of about 55:1 (w/w) relative to the melphalan; or
    the pharmaceutical composition comprises about 200 mg of melphalan as a hydrochloride salt and the cyclodextrin derivative is present in a ratio of 25:1 to 35:1 (w/w) relative to the melphalan; or the pharmaceutical composition comprises about 200 mg of melphalan as a hydrochloride salt and the cyclodextrin derivative is present in a ratio of about 27:1, about 30:1, or about 32:1 (w/w) relative to the melphalan.

The present disclosure is directed to a method of treating a subject suffering from a neoplastic disorder, the method comprising diluting a composition with an aqueous diluent to provide a dilute pharmaceutical composition comprising 25 mg to 125 mg of a nitrogen mustard, such as melphalan, mechlorethamine, cyclophosphamide, ifosfamide, bendamustine, etc., and a cyclodextrin derivative of formula I:

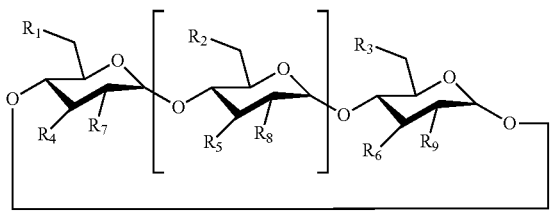

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the dilute pharmaceutical composition has a pH of about 4 to about 6. In some embodiments, the nitrogen mustard comprises melphalan, wherein the cyclodextrin derivative is present in a concentration of at, least 50:1 (w/w) relative to the melphalan; wherein the melphalan in the dilute pharmaceutical composition degrades by 2% or less at about 25° C. within 5 hours, or 4% or less at about 25° C. within 10 hours after the diluting; and administering the dilute pharmaceutical composition by injection to the subject in need thereof.

In some embodiments, the neoplastic disorder is: myeloma, multiple myeloma, acute myelogenous leukemia, melanoma, malignant melanoma, breast cancer, ovarian cancer, testicular cancer, advanced prostate cancer, a neuroendocrine cancer, metastatic melanoma (e.g., metastatic ocular melanoma, metastatic cutaneous melanoma, and the like), a metastatic neuroendocrine tumor, a metastatic adenocarcinoma tumor, hepatocellular carcinoma, osteogenic sarcoma, polycythemia veraplasma, plasma cell neoplasm, amyloidosis, scleromyxedema, or a combination thereof. In some embodiments, the neoplastic disorder is multiple myeloma and the administering is systemic and provides palliative treatment of the multiple myeloma.

Some embodiments include a method for conditioning a subject in need of a stem cell transplantation, the method comprising administering a nitrogen mustard, such as melphalan, at a dose of 50 mg/m² to 300 mg/m² per day to the subject in need of the stem cell transplantation, wherein the nitrogen mustard is administered in a pharmaceutical composition comprising the nitrogen mustard and a cyclodextrin derivative of formula I:

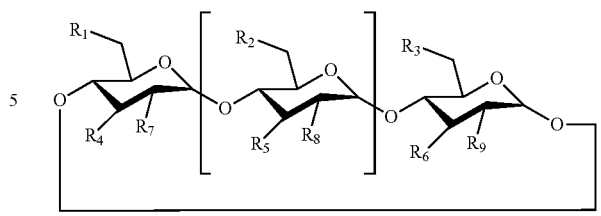

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the pharmaceutical composition has, a pH of about 4 to about 6. In some embodiments, the nitrogen mustard is melphalan and the cyclodextrin derivative is present in a ratio of at least 25:1 (w/w) relative to the melphalan.

In some embodiments, at least one of $R_1$, $R_2$, $R_3$, $R_4$, $R_5$, $R_6$, $R_7$, $R_8$ and $R_9$ is a hydroxy-substituted-$C_3$ group.

In some embodiments, $R_1$, $R_2$, $R_3$, $R_4$, $R_5$, $R_6$, $R_7$, $R_8$ and $R_9$ are independently a straight-chain or branched $C_1$-$C_8$-(alkylene)-$SO_3^-$ group having a degree of substitution of 4 to 8 per cyclodextrin derivative, and the remaining substituents are —H.

In some embodiments, at least one of $R_1$, $R_2$, $R_3$, $R_4$, $R_5$, $R_6$, $R_7$, $R_8$ and $R_9$ is substituted with a straight-chain $C_4$-(alkylene)-$SO_3^-$ group.

In some embodiments, a pharmaceutical composition or a dilute pharmaceutical composition is substantially free of an alcohol.

In some embodiments, the aqueous diluent is a saline solution.

In some embodiments, a dilute pharmaceutical composition is stored about 0.5 hours to about 48 hours prior to the administering. In some embodiments, the nitrogen mustard, such as melphalan, in a pharmaceutical composition degrades by 2% or less at about 25° C. within 5 hours, or 4% or less at about 25° C. within 10 hours after the diluting.

In some embodiments, a subject suffering from a neoplastic disorder or in need of a stem cell transplantation is a pediatric subject.

In some embodiments, the administering is performed intravenously. In some embodiments, the administering is performed via a limb perfusion.

In some embodiments, the administering is for a period of two or more days.

In some embodiments, the administering provides a nitrogen mustard $C_{max}$ in a subject that is at least 20% or greater than a nitrogen mustard $C_{max}$ provided by a nitrogen mustard formulation containing an equivalent dose of nitrogen mustard and lacking the cyclodextrin derivative. In some embodiments, the administering provides a nitrogen mustard $AUC_{0-t}$ in a subject that is at least 20% or greater than a nitrogen mustard $AUC_{0-t}$ provided by a nitrogen mustard formulation containing an equivalent dose of nitrogen mustard and lacking the cyclodextrin derivative.

In some embodiments, the administering provides a melphalan $C_{max}$ in a subject that is at least 20% or greater than a melphalan $C_{max}$ provided by a melphalan formulation containing an equivalent dose of melphalan and lacking the cyclodextrin derivative. In some embodiments, the administering provides a melphalan $AUC_{0-t}$ in a subject that is at least 20% or greater than a melphalan $AUC_{0-t}$ provided by a melphalan formulation containing an equivalent dose of melphalan and lacking the cyclodextrin derivative.

Some methods comprise diluting a concentrated nitrogen mustard composition, such as a composition of melphalan, mechlorethamine, cyclophosphamide, ifosfamide, bendamustine, etc., with an aqueous diluent to provide the pharmaceutical composition. In some embodiments, a concentrated nitrogen mustard composition comprises 50 mg to 500 mg of the nitrogen mustard. In some embodiments, a concentrated melphalan composition comprises about 200 mg of the nitrogen mustard.

Some methods comprise diluting a concentrated melphalan composition with an aqueous diluent to provide the pharmaceutical composition. In some embodiments, a concentrated melphalan composition comprises 50 mg to 500 mg of melphalan. In some embodiments, a concentrated melphalan composition comprises about 200 mg of melphalan.

In some embodiments, a first container comprises povidone in an amount of 10 mg to 30 mg, and a second container comprises a pH-adjusting agent in a concentration sufficient to provide a pH of about 4 to about 6 when the first container and the second container are combined.

In some embodiments, the cyclodextrin derivative present in the second container is a compound of formula II:

II

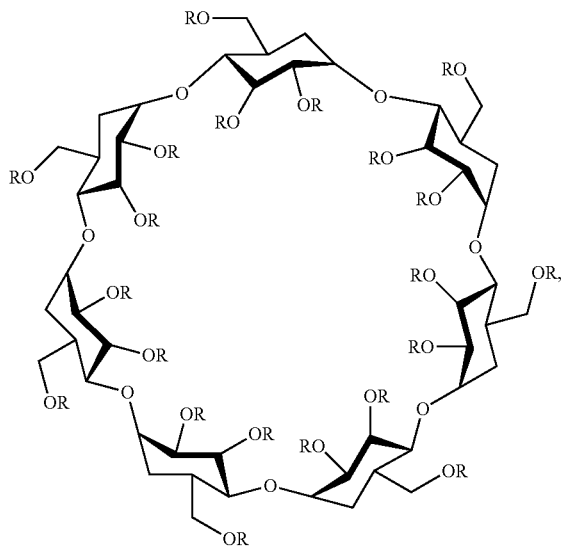

wherein 21-x of the R groups are H and x of the R groups are —(CH$_2$)$_4$-SO$_3^-$Na$^+$, and x=6.0-7.1; wherein the first container comprises about 200 mg of a nitrogen mustard, such as melphalan, mechlorethamine, cyclophosphamide, ifosfamide, bendamustine, etc., as a hydrochloride salt; and wherein the cyclodextrin derivative is present in the second container in an amount of about 27:1, about 30:1, or about 32:1 (w/w) relative to the nitrogen mustard.

Some embodiments include a pharmaceutical kit comprising a first container comprising 25 mg to 125 mg of melphalan as a hydrochloride salt and an optional water-soluble polymer; and a second container comprising an aqueous diluent, an optional buffer, and a cyclodextrin derivative of formula I:

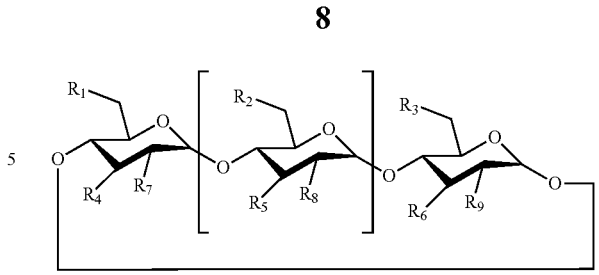

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-SO$_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-SO$_3^-$ group; wherein the cyclodextrin derivative is present in the second container in a concentration of at least 50:1 (w/w) relative to the melphalan; and wherein combining the first container and the second container provides a dilute pharmaceutical composition having a pH of about 4 to about 6 that degrades by 2% or less at about 25° C. within 5 hours, or 4% or less at about 25° C. within 10 hours after the diluting.

Some embodiments include a pharmaceutical kit comprising a first container comprising 150 mg to 250 mg of melphalan as a hydrochloride salt and an optional water-soluble polymer; and a second container comprising an aqueous diluent, an optional buffer, and a cyclodextrin derivative of formula I:

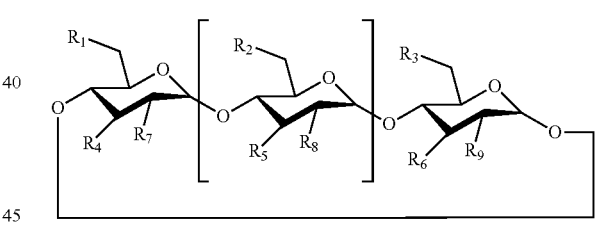

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-SO$_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-SO$_3^-$ group; wherein the cyclodextrin derivative is present in the second container in a concentration of 25:1 to 35:1 (w/w) relative to the melphalan; and wherein combining the first container and the second container provides a dilute pharmaceutical composition having a pH of about 4 to about 6 that degrades by 2% or less at about 25° C. within 5 hours, or 4% or less at about 25° C. within 10 hours after the diluting.

In some embodiments, a first container comprises povidone in an amount of 10 mg to 30 mg, and a second container comprises a pH-adjusting agent in a concentration sufficient to provide a pH of about 4 to about 6 when the first container and the second container are combined.

In some embodiments, the cyclodextrin derivative present in the second container is a compound of formula II:

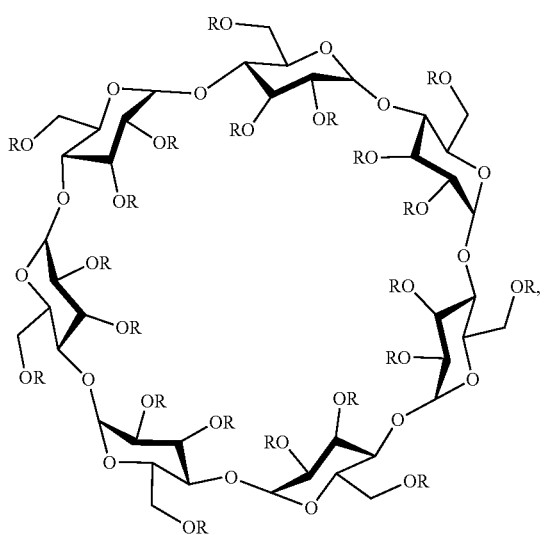

wherein 21-x of the R groups are H and x of the R groups are —$(CH_2)_4$-$SO_3^-$$Na^+$, and x=6.0-7.1; wherein the first container comprises about 200 mg of melphalan as a hydrochloride salt; and wherein the cyclodextrin derivative is present in the second container in an amount of about 27:1, about 30:1, or about 32:1 (w/w) relative to the melphalan.

Further embodiments, features, and advantages of the present embodiments, as well as the composition, structure and operation of the various embodiments, are described in detail below with reference to the accompanying drawings.

BRIEF DESCRIPTION OF THE FIGURES

The accompanying drawings, which are incorporated herein and form a part of the specification, illustrate one or more embodiments and, together with the description, further serve to explain the principles of the embodiments and to enable a person skilled in the pertinent art to make and use various embodiments.

Figure 1:
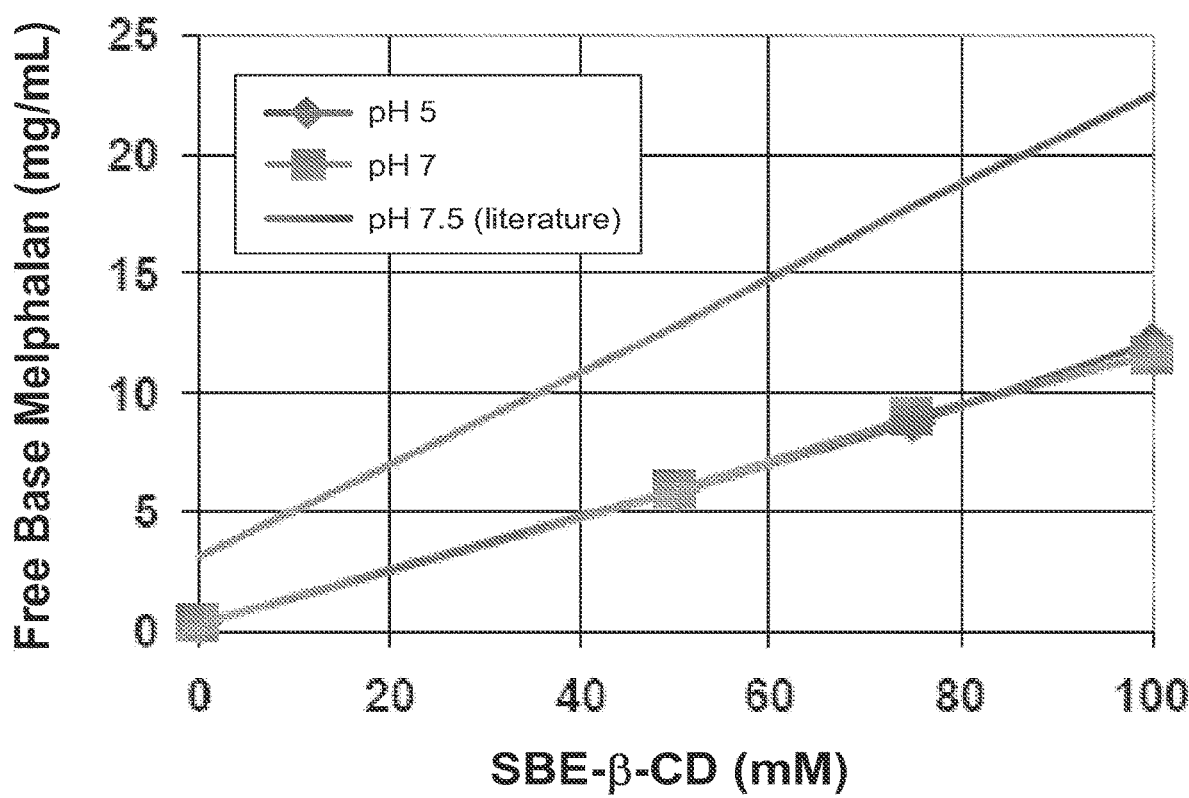
FIG. 1 provides a graphic representation of the solubility of free base melphalan as a function of pH and the concentration of a cyclodextrin derivative.

One or more embodiments of the present invention will now be described with reference to the accompanying drawings. In the drawings, like reference numbers can indicate identical or functionally similar elements. Additionally, the left-most digit(s) of a reference number can identify the drawing in which the reference number first appears.

DETAILED DESCRIPTION

Throughout the specification, use of the term "about" with respect to any quantity is contemplated to include that quantity. For example, "about 10 mL" is contemplated herein to include "10 mL," as well as values understood in the art to be approximately 10 mL with respect to the entity described.

Combinations and sub-combinations of the various aspects and embodiments disclosed herein are specifically contemplated. Further, when a particular feature, structure, or characteristic is described in connection with an embodiment, it is understood that it is within the knowledge of one skilled in the art to effect such feature, structure, or characteristic in connection with other embodiments whether or not explicitly described. These and other embodiments will be apparent upon reference to the following detailed description, examples, claims and attached figures.

Nitrogen Mustards

A composition, formulation, or unit dosage form can include a nitrogen mustard compound, such as mechlorethamine, mustine, cyclophosphamide, chlorambucil, uramustine, ifosfamide, melphalan, bendamustine, etc. A nitrogen mustard having one or more chiral centers could include an enantiomerically or diastereomerically pure form any isomer, or could contain any mixture of isomers. A nitrogen mustard may also be in an alternate solid form, such as an addition salt, a polymorph, a solvate, a hydrate, a dehydrate, a co-crystal, an anhydrous form, and or an amorphous form, etc.

Melphalan

In some embodiments, a composition, formulation or unit dosage form can comprise melphalan, which has the following chemical structure:

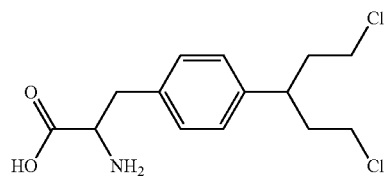 [SMILES: NC(Cc1ccc(C(CCCl)CCCl)cc1)C(=O)O]

As used herein, the term "melphalan" refers to the L-isomer of the above compound, 4-[bis(chloroethyl)amino]phenylalanine, as well as addition salts, polymorphs, solvates, hydrates, dehydrates, co-crystals, anhydrous, and amorphous forms thereof. Melphalan contains a chiral atom, and thus, as used herein, "melphalan" can refer to the substantially pure form of the L-isomer. As used herein, "substantially pure" refers to melphalan having a purity of 90% or higher, 95% or higher, 98% or higher, 99% or higher, 99.5% or higher, or 99.9% or higher.

The D-isomer of the above compound, known as melphalan, is less active against certain animal tumors, and the dose needed to produce effects on chromosomes is larger than that required with melphalan. The racemic (DL-) form is known as merphalan or sarcolysin. Some melphalan compositions are substantially free of merphalan. In some embodiments, melphalan is present as a hydrochloride salt having a purity of 95% or greater, 98% or greater, 99% or greater, 99.9% or greater, or 99.99% or greater.

Melphalan is a bifunctional alkylating agent that is active against selected human neoplastic diseases. The molecular formula for melphalan is $C_{13}H_{18}Cl_2N_2O_2$, and the molecular weight of the free base form is 305.20 g/mol. Melphalan is practically insoluble in water (pH 7) and has a $pK_a$ of about 2.5.

In some embodiments, the pharmaceutical compositions and dosage forms comprise a nitrogen mustard, such as melphalan, mechlorethamine, cyclophosphamide, ifosfamide, bendamustine, etc. as a hydrochloride salt. As used herein, reference to a nitrogen mustard as a hydrochloride salt, e.g. "melphalan as a hydrochloride salt," refers to the hydrochloric acid addition salt of the nitrogen mustard compound. However, amounts and concentrations of a nitrogen mustard are provided in reference to an equivalent mass of free base of the nitrogen mustard. For example, 5 mg of "melphalan as a hydrochloride salt" refers to 5 mg of the active agent melphalan, exclusive of the hydrochloride addition salt, which if considered would provide a total mass of about 5.6 mg. Reference to an amount of a nitrogen mustard refers to the equivalent amount of the free base, but does not limit the form of the nitrogen mustard. For example, "5 mg of melphalan" could include 5 mg of melphalan free base, 5.6 mg of the hydrochloride addition salt of melphalan, or an equivalent amount of another salt of melphalan.

With respect to any pharmaceutical product or composition comprising a nitrogen mustard, such as melphalan, mechlorethamine, cyclophosphamide, ifosfamide, bendamustine, etc. and a cyclodextrin derivative, in some embodiments a single vial of the product or composition contains about 10 mg to about 500 mg, about 50 mg to about 200 mg, about 50 mg to about 100 mg, about 50 mg, about 100 mg, or about 150 mg of a nitrogen mustard, such as melphalan, mechlorethamine, cyclophosphamide, ifosfamide, bendamustine, etc.

Cyclodextrin Derivatives

The compositions, formulations and/or unit dosage forms comprise a cyclodextrin derivative, such as a water-soluble cyclodextrin derivative. As used herein, "cyclodextrin derivative" includes a cyclic oligosaccharide comprising five or more α-D-glucopyranoside units linked in a circular 1→4 configuration, and comprising a substituent group attached to one or more of the glucopyranoside units at the 2, 3 and/or 6 position(s) through an ether bond (—O—R—, where R refers to the substituent group).

In some embodiments, the cyclodextrin derivative is a compound of formula I:

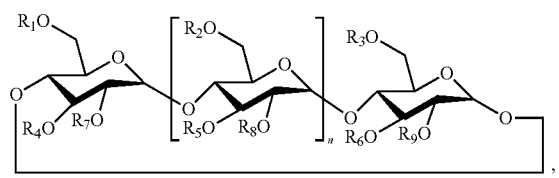

I wherein n is 4, 5 or 6, wherein $R_1$, $R_2$, $R_3$, $R_4$, $R_5$, $R_6$, $R_7$, $R_8$ and $R_9$ are independently selected from: —H, a straight-chain or branched $C_1$-$C_8$-(alkylene)-$SO_3^-$ group, and an optionally substituted straight-chain or branched $C_1$-$C_6$ group. Compounds of Formula 1 can often be water soluble.

In some embodiments, a cyclodextrin is selected based upon an average degree of substitution ("ADS"), which as used herein refers to the average number of substituent groups per cyclodextrin molecule. The average degree of substitution for cyclodextrin derivatives is described in detail in WO 2009/018069, which is incorporated herein by reference in its entirety. As used herein, a cyclodextrin derivative composition is referred to by the following notation: the substituent(s) are abbreviated (e.g., sulfobutyl ether groups are abbreviated as "SBE") with a subscript denoting the ADS of the substituent, and cyclodextrin structure is defined. For example, a sulfobutyl ether-derivatized β-cyclodextrin composition having an ADS of 6.5 is referred to as "$SBE_{6.5}$-β-CD." As a second example, a (β-cyclodextrin composition comprising cyclodextrin molecules derivatized with both sulfobutyl ether and hydroxypropyl groups is referred to as "$SBE_{4.2}$-$HP_{2.5}$-β-CD," wherein the ADS of the sulfobutyl ether groups is 4.2 and the ADS of the hydroxypropyl groups is 2.5.

Cyclodextrin derivatives suitable for use include cyclodextrin compositions bearing substituent groups ($R_1$-$R_9$ and R in formulas I and II, respectively) that are independently selected from: —H, a straight-chain or branched $C_1$-$C_8$-(alkylene)-$SO_3^-$ group, and an optionally substituted straight-chain or branched $C_1$-$C_6$ group.

In some embodiments, at least one of $R_1$, $R_2$, $R_3$, $R_4$, $R_5$, $R_6$, $R_7$, $R_8$ and $R_9$ of formula I is substituted with a straight-chain $C_4$-(alkylene)-$SO_3^-$ group. Exemplary $C_1$-$C_8$-(alkylene)-$SO_3^-$ groups suitable for use include, but are not limited to, sulfoethyl, sulfopropyl, 1-methyl-sulfopropyl, sulfobutyl, 1-methyl-sulfobutyl, 2-methyl-sulfobutyl, 1-methyl-sulfobut-3-yl, 2-ethyl-sulfobutyl, 3-ethyl-sulfobutyl, sulfopentyl, 1-sulfopent-3-yl, sulfohexyl, sulfoheptyl, sulfooctyl, and the like, and combinations thereof.

In some embodiments, $R_1$, $R_2$, $R_3$, $R_4$, $R_5$, $R_6$, $R_7$, $R_8$ and $R_9$ of formula I are independently a straight-chain or branched $C_1$-$C_8$-(alkylene)-$SO_3^-$ group having an ADS of 4 to 8, 4 to 7.5, 4 to 7, 4 to 6.5, 4.5 to 8, 4.5 to 7.5, 4.5 to 7, 5 to 8, 5 to 7.5, 5 to 7, 5.5 to 8, 5.5 to 7.5, 5.5 to 7, 5.5 to 6.5, 6 to 8, 6 to 7.5, 6 to 7.1, 6.5 to 7, about 6.5, or about 7 per cyclodextrin derivative, and the remaining substituents are —H.

In some embodiments, a substituent is an optionally substituted straight-chain or branched $C_1$-$C_6$ group. As used herein, "optionally substituted" refers to one or more optional substituents such as: halogen (i.e., —F, —Cl, —Br, —I), —$NO_2$, —C≡N, —$OR_{22}$, —$SR_{22}$, —$SO_2R_{22}$, —C(=O)$OR_{22}$, —C(=O)$R_{22}$, —C(=O)N($R_{22}$)$_2$, —$SO_2$N($R_{22}$)$_2$, —$SO_2$N(H)C(=O)$R_{22}$, —$SO_2$N(H)C(=O)$OR_{22}$ (wherein $R_{22}$ is not H), —N($R_{22}$)$_2$, —N($R_{22}$)$SO_2R_{22}$, —N($R_{22}$)C(O)$_mR_{22}$ (wherein m=1 or 2), —N($R_{22}$)C(O)N($R_{22}$)$_2$, —N($R_{22}$)$SO_2$N($R_{22}$)$_2$, —O—C(=O)$R_{22}$, —O—C(=O)$OR_{22}$, —O—C(=O)N($R_{22}$)$_2$, —C(=O)N(H)$SO_2$N($R_{22}$)$_2$, —C(=O)N(H)$SO_2R_{22}$, oxo (or keto, i.e., =O), thioxo (i.e., =S), imino (i.e., =$NR_{22}$), —$NR_{22}$—C(=$NR_{22}$)$R_{22}$, —$NR_{22}$—C(=$NR_{22}$)N($R_{22}$)$_2$, —C(=$NR_{22}$)N($R_{22}$)$_2$, —O—C(=$NR_{22}$)N($R_{22}$)$_2$, —O—C(=$NR_{22}$)$R_{22}$, —C(=$NR_{22}$)$R_{22}$, —C(=$NR_{22}$)$OR_{22}$, and ionic forms thereof (e.g., —$N^+$($R_{22}$)$_2X^-$, and the like, wherein $X^-$ is a pharmaceutically acceptable anion), wherein $R_{22}$ is independently selected at each occurrence from H, and $C_1$-$C_4$ alkyl.

Exemplary optionally substituted straight-chain or branched $C_1$-$C_6$ groups include, but are not limited to, 2-hydroxypropyl, 3-hydroxypropyl, 2,3-dihydroxypropyl, 3-oxobutyl, and 2-ethoxy-ethyl.

In some embodiments, at least one of $R_1$, $R_2$, $R_3$, $R_4$, $R_5$, $R_6$, $R_7$, $R_8$ and $R_9$ of formula I is a hydroxy-substituted-$C_3$ group. In some embodiments, the cyclodextrin derivative comprises β-cyclodextrin that includes a hydroxy-substituted-$C_3$ group having an ADS of 1 to 8, 2 to 8, 3 to 7, 4 to 7.5, 4.3 to 7.5, about 1, about 2, about 2.5, about 3, about 3.5, about 4, about 4.3, about 5, about 5.5, about 6, about 6.5, about 7, or about 7.5.

Exemplary cyclodextrin compositions, and methods of making the same, also include those described in U.S. Pat. Nos. 5,134,127, 5,241,059, 5,376,645, 5,874,418, 6,046,177, 6,133,248, 6,153,746, 6,204,256, 7,034,013, 7,629,331, and 7,635,773, U.S. Pub. No. 2009/0012042, and PCT Pub. No. WO 2005/117911, the contents of each of which is incorporated herein by reference in the entirety.

In some embodiments, the cyclodextrin derivative is a compound of formula II:

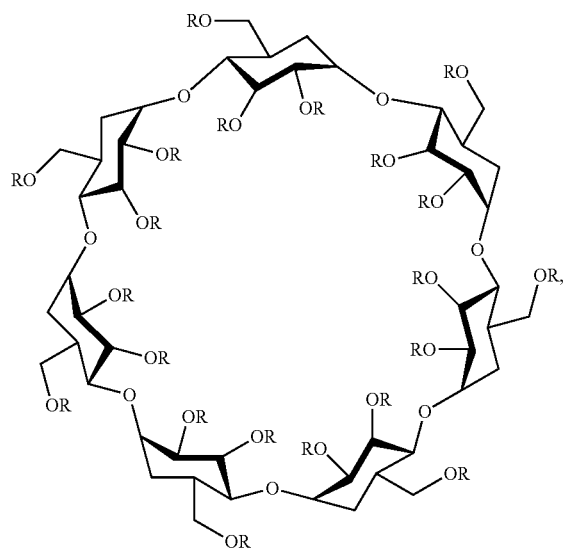

wherein 21-x of the R groups are H and x of the R groups are —$(CH_2)_4^-SO_3^-Na^+$. In some embodiments, x=6.0-7.1. In some embodiments, the cyclodextrin derivative of formula II has an average molecular weight of about 2163 g/mol.

In some embodiments, the water soluble cyclodextrin derivative is an sulfobutylether-β-cyclodextrin [(SBE)-β-cyclodextrin]. In some embodiments, an (SBE)-β-cyclodextrin can have an ADS of about 1 to about 10, about 3 to about 10, about 5 to about 9, about 6 to about 8, about 6 to about 7, or about 6.5. For convenience, with respect to any pharmaceutical product or composition comprising a nitrogen mustard compound, such as melphalan, and a cyclodextrin derivative, any suitable cyclodextrin derivative can be referred to as an "(SBE)$_{x\ m}$-β-cyclodextrin, wherein x refers to the ADS. For example, (SBE)$_{6.5\ m}$-β-cyclodextrin has an ADS of about 6.5.

In some embodiments, the cyclodextrin derivative is a sulfobutyl ether-β-cyclodextrin having an ADS of about 7 (e.g., CAPTISOL®, CyDex Pharmaceuticals, Inc., Lenexa, Kans.). CAPTISOL® cyclodextrin is a polyanionic β-cyclodextrin derivative with a sodium sulfonate salt separated from the lipophilic cyclodextrin cavity by a butyl ether spacer group, or sulfobutylether (SBE). CAPTISOL® cyclodextrin has been shown to be safe when administered parenterally, orally, or via inhalation and does not exhibit the nephrotoxicity associated with (β-cyclodextrin. Relative to β-cyclodextrin, CAPTISOL® sulfoalkyl ether cyclodextrin provides comparable or higher complexation characteristics and superior water solubility in excess of 90 g per 100 mL, a 50-fold improvement. Melphalan has a low binding affinity with CAPTISOL® ($K_a=3\times10^2$ $M^{-1}$).

In some embodiments, the cyclodextrin derivative includes a substituent that bears an ionic group that can optionally form a salt with a pharmaceutically acceptable anion or cation. Pharmaceutically acceptable cations suitable for forming salts with negatively charged cyclodextrin derivatives include, but are not limited to, $H^+$, $Li^+$, $Na^+$, $K^+$, $Mg^{2+}$, $Ca^{2+}$, ammonium and amine cations such as cations of ($C_1$-$C_6$)-alkylamines, ($C_4$-$C_8$)-cycloalkylamines (e.g., piperidine, pyrazine, and the like), ($C_1$-$C_6$)-alkanolamines, and ($C_4$-$C_8$)-cycloalkanolamines, and the like, and combinations thereof. In some embodiments, a pharmaceutically acceptable cation is $Na^+$. Pharmaceutically acceptable anions suitable for forming salts with positively charged cyclodextrin derivatives include, but are not limited to, halides (e.g., $Cl^-$ and the like), anions of ($C_1$-$C_6$)-alkyl acids (e.g., acetate, oxalate, fumarate, succinate, and the like, and combinations thereof.

In some embodiments, the water soluble cyclodextrin derivative can comprise a combination of two different types of cyclodextrin derivatives, such as sulfoalkylether β-cyclodextrin (i.e. sulfobutylether β-cyclodextrin) and hydroxyalkyl β-cyclodextrin (i.e. hydroxypropyl β-cyclodextrin). In some embodiments, the water soluble cyclodextrin derivative is a mixture of sulfobutylether β-cyclodextrin and hydroxypropyl β-cyclodextrin. The two types of cyclodextrin ratio may have a molar ratio of about 4 (4 moles sulfoalkylether β-cyclodextrin to 1 mole hydroxyalkyl β-cyclodextrin) to about 0.25, about 2 to about 0.5, about 1.2 to about 0.8, or about 1. In some embodiments, such a mixture may have a cyclodextrin to nitrogen mustard ratio (e.g. cyclodextrin to melphalan ratio) of about 5 (5 moles cyclodextrin to 1 mole nitrogen mustard such as melphalan) to about 100, about 7 to about 20, about 8 to about 12, or about 10.

With respect to any pharmaceutical product or composition comprising a nitrogen mustard, such as melphalan, mechlorethamine, cyclophosphamide, ifosfamide, bendamustine, etc., and a water-soluble cyclodextrin derivative, any suitable amount of water-soluble cyclodextrin derivative can be used. In some embodiments, a single vial of pharmaceutical product or composition can contain about 1000 mg to about 5000 mg, about 2000 mg to about 4000 mg, about 2000 mg to about 3000 mg, or about 2500 mg to about 3000 mg of the water-soluble cyclodextrin derivative.

With respect to any pharmaceutical product or composition comprising a nitrogen mustard, such as melphalan, mechlorethamine, cyclophosphamide, ifosfamide, bendamustine, etc., and a cyclodextrin derivative, any suitable ratio of nitrogen mustard compound and cyclodextrin derivative may be used. In some embodiments, a cyclodextrin derivative, such as a water-soluble cyclodextrin derivative [e.g. an (SBE)-β-cyclodextrin], and a nitrogen mustard, such as melphalan, mechlorethamine, cyclophosphamide, ifosfamide, bendamustine, etc., can have a weight ratio (cyclodextrin derivative:nitrogen mustard) of at least about 50:1, about 50:1 to about 100:1, about 55:1 to about 60:1, about 50:1, about 55:1, or about 60:1.

With respect to any pharmaceutical product or composition comprising a nitrogen mustard and a water-soluble cyclodextrin derivative, in some embodiments, a nitrogen mustard, such as melphalan, mechlorethamine, cyclophosphamide, ifosfamide, bendamustine, etc., and the water-soluble cyclodextrin derivative are present in a solid. With respect to any composition comprising a nitrogen mustard, such as melphalan, mechlorethamine, cyclophosphamide, ifosfamide, bendamustine, etc., and a cyclodextrin derivative, the composition may have any suitable pH, such as about 2 to about 8, about 4 to about 6, about 5 to about 6, or about 5 to about 5.5.

Pharmaceutical Compositions and Unit Dosage Forms

The present disclosure is directed to pharmaceutical compositions and unit dosage forms comprising a nitrogen mustard, such as melphalan, mechlorethamine, cyclophosphamide, ifosfamide, bendamustine, etc., and a cyclodextrin derivative, e.g. the nitrogen mustard and the cyclodextrin can be present together in a single vial. The pharmaceutical compositions of the present disclosure are suitable for parenteral administration to a subject. Parenteral administration of the pharmaceutical compositions can include, but is not limited to, an injection. Because parenteral administration can bypass a subject's natural defenses against contaminants, the pharmaceutical compositions are sterile or capable of being sterilized prior to administration.

Exemplary pharmaceutical compositions include, but are not limited to, solutions, suspensions or emulsions ready for administration, solutions, suspensions or emulsions ready to be dissolved in and/or diluted with a pharmaceutically acceptable vehicle, and dry products ready to be dissolved in and/or diluted with a pharmaceutically acceptable vehicle.

Generally, the pharmaceutical compositions of the present disclosure comprise a nitrogen mustard, such as melphalan, mechlorethamine, cyclophosphamide, ifosfamide, bendamustine, etc., in a concentration suitable for treating a condition that is amenable to treatment with the nitrogen mustard. Thus, the pharmaceutical compositions of the present disclosure can be used to prepare a unit dosage form comprising a therapeutically effective amount of a nitrogen mustard for administering to a subject in need thereof. Some embodiments include a unit dosage form that comprises a nitrogen mustard in a concentration that is suitable for administration without dilution. Alternatively, a unit dosage form of the present disclosure can be diluted prior to administration to a subject in need thereof.

The present disclosure is also directed to a pharmaceutical composition comprising 25 mg to 125 mg, 25 mg to 100 mg, 25 mg to 75 mg, 25 mg to 50 mg, 50 mg to 125 mg, 50 mg to 100 mg, 75 to 125 mg, 100 to 125 mg, about 25 mg, about 50 mg, about 75 mg, about 100 mg, or about 125 mg of a nitrogen mustard, such as melphalan, as a hydrochloride salt, an optional buffer, and a cyclodextrin derivative of formula I:

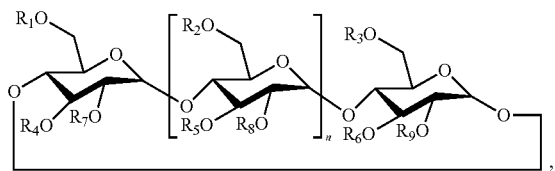

wherein n is 4, 5 or 6; wherein $R_1$, $R_2$, $R_3$, $R_4$, $R_5$, $R_6$, $R_7$, $R_8$ and $K_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the pharmaceutical composition has a pH of about 4 to about 6, about 4 to about 5, about 4.5 to about 6, about 5 to about 6, about 5.5 to about 6, about 4, about 4.5, about 5, about 5.5, or about 6. In some embodiments, the nitrogen mustard comprises melphalan, wherein dilution of the pharmaceutical composition with an aqueous solution provides a solution in which the melphalan degrades by 2% or less at about 25° C. within 5 hours, or by 4% or less at about 25° C. within 10 hours after the dilution; and wherein the cyclodextrin derivative is present in a ratio of 50:1 to 100:1, 55:1 to 60:1, about 50:1, about 55:1, or about 60:1 (w/w) relative to the melphalan.

The present disclosure is also directed to a pharmaceutical composition comprising 150 mg to 300 mg, 150 mg to 250 mg, 150 mg to 225 mg, 175 mg to 250 mg, 200 mg to 250 mg, about 150 mg, about 175 mg, about 200 mg, about 225 mg, or about 250 mg of a nitrogen mustard, such as melphalan, as a hydrochloride salt, an optional buffer, and a cyclodextrin derivative of formula I:

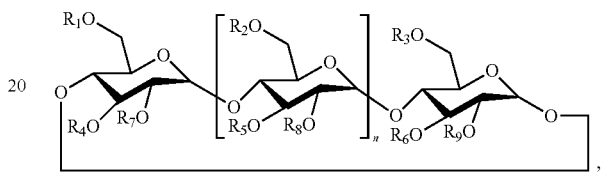

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the pharmaceutical composition has a pH of about 4 to about 6. In some embodiments, the nitrogen mustard comprises melphalan wherein dilution of the pharmaceutical composition with an aqueous solution provides a melphalan solution in which the melphalan degrades by 2% or less at about 25° C. within 5 hours, or 4% or less at about 25° C. within 10 hours after the dilution; and wherein the cyclodextrin derivative is present in a ratio of 25:1 to 35:1, about 27:1, about 30:1, or about 32:1 (w/w) relative to the melphalan.

In some embodiments, the cyclodextrin derivative is a compound of formula II:

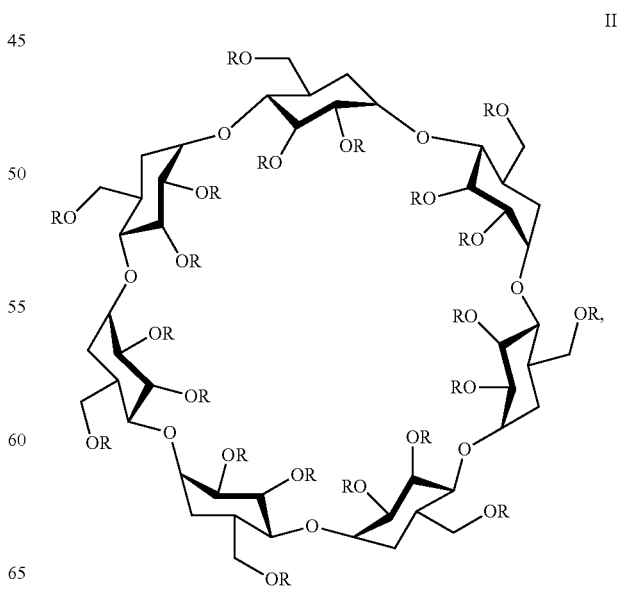

wherein 21-x of the R groups are H and x of the R groups are —(CH$_2$)$_4$$^-$SO$_3$$^-$Na$^+$, and x=6.0-7.1.

In some embodiments, the cyclodextrin derivative is a compound of formula II:

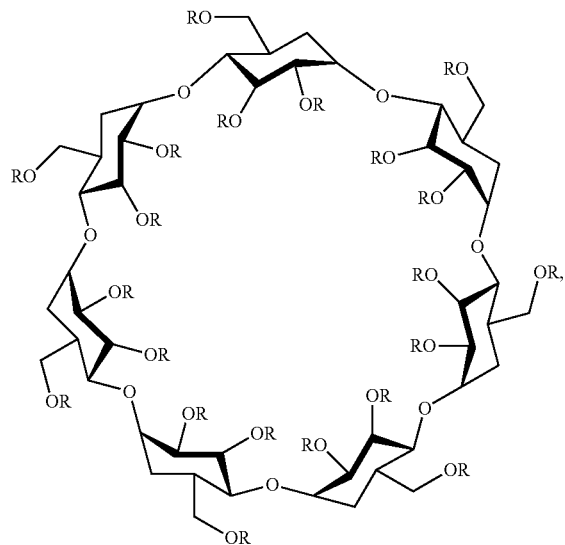

II wherein 21-x of the R groups are H and x of the R groups are —(CH$_2$)$_4$$^-$SO$_3$$^-$Na$^+$, and x=6.0-7.1; and the pharmaceutical composition comprises about 50 mg of a nitrogen mustard, such as melphalan, as a hydrochloride salt and the cyclodextrin derivative is present in a concentration of 50:1 to 100:1, 55:1 to 60:1, about 50:1, about 55:1, or about 60:1 (w/w) relative to the nitrogen mustard; or the pharmaceutical composition comprises about 200 mg of the nitrogen mustard, such as melphalan, as a hydrochloride salt and the cyclodextrin derivative is present in a ratio of 25:1 to 35:1, about 27:1, about 30:1, or about 32:1 (w/w) relative to the nitrogen mustard.

Sterile solutions, suspensions, emulsions and the like can be prepared by incorporating a nitrogen mustard, such as melphalan, mechlorethamine, cyclophosphamide, ifosfamide, bendamustine, etc., into an appropriate solvent or carrier with the other optional ingredients enumerated herein, followed by sterilization. Sterile powders can be prepared by spray drying, aseptic spray drying, vacuum drying, or freeze drying a sterile solution, suspension, or emulsion to provide a dried solid (e.g., a powder) comprising a nitrogen mustard, such as melphalan, mechlorethamine, cyclophosphamide, ifosfamide, bendamustine, etc., along with any additional excipients.

Some embodiments include a solid pharmaceutical composition consisting of about 50 mg of a nitrogen mustard, such as melphalan, as a hydrochloride salt, an amount sufficient of an acid, a base, or a combination thereof to provide a pH of about 4 to about 6 upon dilution with a saline solution to a volume of about 10 mL, and a cyclodextrin derivative of formula II

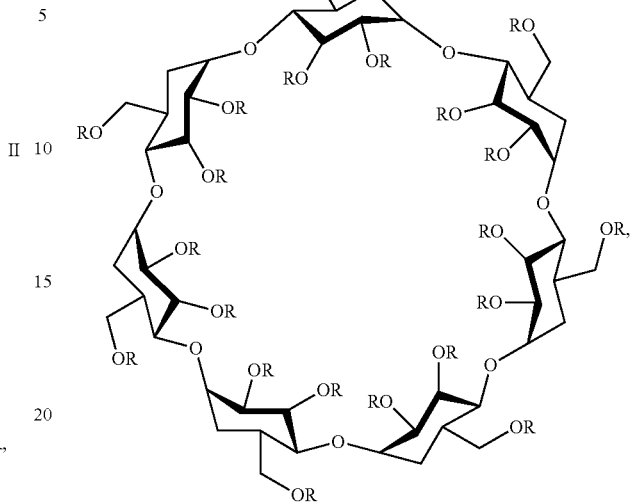

II wherein 21-x of the R groups are H and x of the R groups are —(CH$_2$)$_4$$^-$SO$_3$$^-$Na$^+$, and x-6.0-7.1, wherein dilution of the solid pharmaceutical composition with an aqueous solution provides a nitrogen mustard solution in which the nitrogen mustard has improved stability, and wherein the cyclodextrin derivative is present in a ratio of about 55:1 (w/w) relative to the nitrogen mustard.

In some embodiments, the molar ratio of water soluble cyclodextrin derivative to nitrogen mustard, such as melphalan, is about 7 (10 moles cyclodextrin to 1 mole nitrogen mustard) to about 100, about 10 to about 20, about 9 to about 11, or about 10.

Some embodiments include a solid pharmaceutical composition consisting of about 50 mg of melphalan as a hydrochloride salt, an amount sufficient of an acid, a base, or a combination thereof to provide a pH of about 4 to about 6 upon dilution with a saline solution to a volume of about 10 mL, and a cyclodextrin derivative of formula II

II

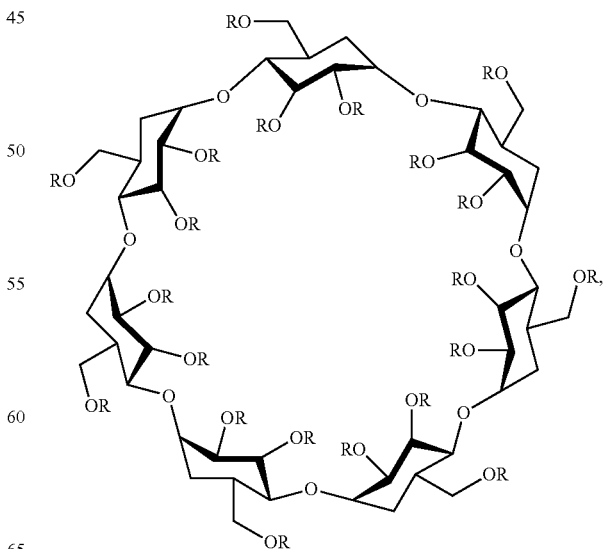

wherein 21-x of the R groups are H and x of the R groups are $-(CH_2)_4{}^-SO_3{}^-Na^+$, and x-6.0-7.1, wherein dilution of the solid pharmaceutical composition with an aqueous solution provides a melphalan solution in which the melphalan degrades by 2% or less at about 25° C. within 5 hours, or by 4% or less at about 25° C. within 10 hours after the diluting, and wherein the cyclodextrin derivative is present in a ratio of about 55:1 (w/w) relative to the melphalan.

In some embodiments, the present disclosure is directed to a solid pharmaceutical composition consisting of about 200 mg of a nitrogen mustard, such as melphalan, as a hydrochloride salt, an amount sufficient of an acid, a base, or a combination thereof to provide a pH of about 4 to about 6 upon dilution with a saline solution to a volume of about 20 mL, and a cyclodextrin derivative of formula II:

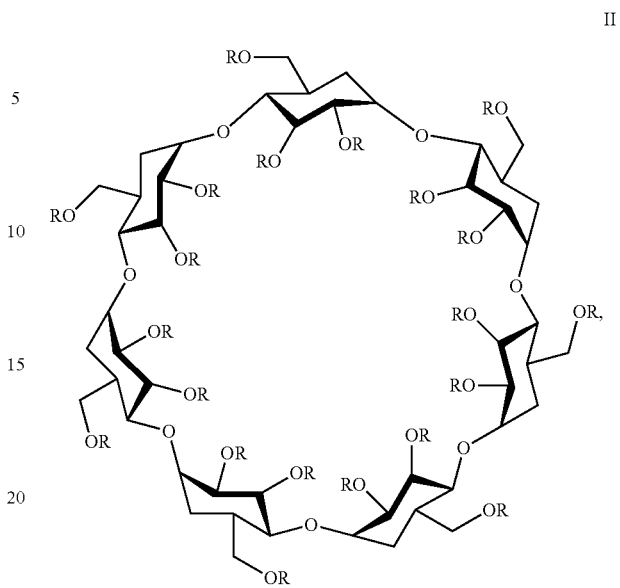

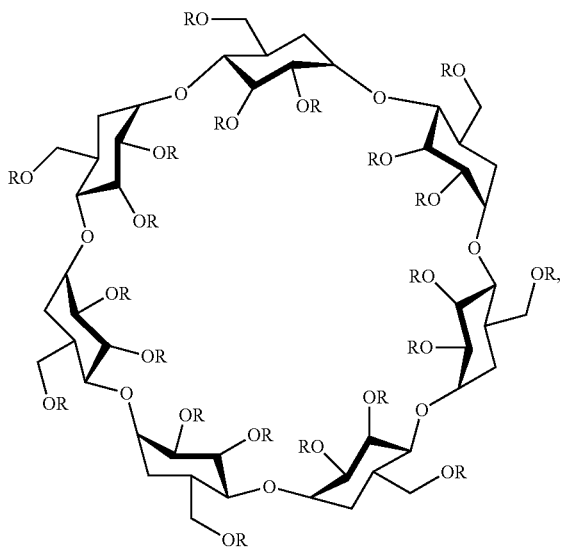

wherein 21-x of the R groups are H and x of the R groups are $—(CH_2)_4{}^-SO_3{}^-Na^+$, and x=6.0-7.1, wherein dilution of the solid pharmaceutical composition with an aqueous solution provides a nitrogen mustard solution in which the nitrogen mustard has improved stability, and wherein the cyclodextrin derivative is present in a ratio of about 27:1, about 30:1, about 32:1, or about 50:1 (w/w), or greater, relative to the nitrogen mustard.

In some embodiments, the present disclosure is directed to a solid pharmaceutical composition consisting of about 200 mg of melphalan as a hydrochloride salt, an amount sufficient of an acid, a base, or a combination thereof to provide a pH of about 4 to about 6 upon dilution with a saline solution to a volume of about 20 mL, and a cyclodextrin derivative of formula II:

wherein 21-x of the R groups are H and x of the R groups are $—(CH_2)_4{}^-SO_3Na^+$, and x=6.0-7.1, wherein dilution of the solid pharmaceutical composition with an aqueous solution provides a melphalan solution in which the melphalan degrades by 2% or less at about 25° C. within 5 hours, or by 4% or less at about 25° C. within 10 hours after the diluting, and wherein the cyclodextrin derivative is present in a ratio of about 27:1, about 30:1, about 32:1, or about 50:1 (w/w), or greater, relative to the melphalan.

In some embodiments, a pharmaceutical composition or unit dosage form comprises a solid (e.g., a powder) or a liquid solution that is diluted with a liquid carrier or diluent prior to administration to a subject. Thus, the pharmaceutical compositions and unit dosage forms include sterile aqueous solutions, suspensions and dispersions, as well as sterile solids (e.g., powders) comprising a nitrogen mustard, such as melphalan, mechlorethamine, cyclophosphamide, ifosfamide, bendamustine, etc., that can be extemporaneously diluted or solubilized to provide a sterile solution, suspension or dispersion.

In some embodiments, the compositions, formulations and/or unit dosage forms comprise a pharmaceutically acceptable excipient. As used herein, "pharmaceutically acceptable" refers to those excipients, compounds, materials, and/or compositions which are, within the scope of sound medical judgment, suitable for contact with the tissues of human beings and animals without excessive toxicity, irritation, allergic response, or other possible complications commensurate with a reasonable benefit/risk ratio.

In some embodiments, the pharmaceutical compositions and unit dosage forms are substantially homogeneous. As used herein, "homogeneous" refers to mixtures, solutions, suspensions, compositions, dosage forms, and/or formulations of the present disclosure that have a uniform distribution of ingredients throughout. Homogeneity is synonymous with uniformity and can refer to intra-sample uniformity, batch-to-batch uniformity, run-to-run uniformity, and/or dosage form-to-dosage form uniformity. For example, intra-sample uniformity can be determined by analyzing a first portion of a sample, mixture, or composition and comparing this with a second portion of the same sample, mixture, or composition. Typical deviations of a composition (e.g., variation in the percentage by weight of excipients and the like) of a substantially homogeneous composition are about 5% or less, about 3% or less, about 2% or less, about 1% or less, or within experimental error.

In some embodiments, a pharmaceutical composition or unit dosage form comprises a pharmaceutically acceptable excipient. As used herein, the term "excipient" refers to any inert substance that can be combined with a nitrogen mustard, such as melphalan, mechlorethamine, cyclophosphamide, ifosfamide, bendamustine, etc., and the sulfoalkyl ether cyclodextrin for preparing the pharmaceutical compositions.

Pharmaceutically acceptable excipients suitable for use with the present disclosure include, but are not limited to, a carrier, a water-soluble polymer, a preservative, an antioxidant, a pH-adjusting agent (e.g., an acidifying agent, an alkalinizing agent, and/or a buffer), a bulking agent, a complexation enhancing agent, a cryoprotectant, a density modifier, an electrolyte, a flavor, a fragrance, a lyophilizing aid (e.g., a bulking agent and/or stabilizing agent), a plasticizer, a solubility-enhancing agent, a stabilizing agent, a sweetener, a surface tension modifier, a volatility modifier, a viscosity modifier, and combinations thereof. In addition, one of skill in the art will recognize that pharmaceutically acceptable excipients can be used in the present disclosure including those listed in *The Handbook of Pharmaceutical Excipients*, 5th Ed., The Pharmaceutical Press and American Pharmacists Association, London, UK and Washington, D.C. (2006), which is incorporated herein by reference in its entirety.

In some embodiments, a composition comprising a nitrogen mustard, such as melphalan, mechlorethamine, cyclophosphamide, ifosfamide, bendamustine, etc., and a water soluble cyclodextrin derivative, further comprises a bulking agent, such as mannitol, lactose, or a sugar.

In some embodiments, a pharmaceutical composition or unit dosage form comprises a pharmaceutically acceptable carrier. As used herein, a "carrier" refers to a vehicle suitable for transferring and/or diluting a pharmaceutical composition or unit dosage form. Pharmaceutically acceptable carriers suitable for use include, but are not limited to, liquids, solids, colloids, gels, and combinations thereof. Liquid carriers suitable for use include solvents, liquid dispersion mediums, and the like, such as, but not limited to, water, ethanol, a polyol (e.g., glycerol, propylene glycol, liquid polyethylene glycols, and the like), a vegetable oil, a nontoxic glyceryl ester, and combinations thereof. In some embodiments, a liquid carrier is selected from: a dextrose solution, a saline solution, plasma, and lactated Ringer's solution.

In some embodiments, a pharmaceutical composition or unit dosage form does not include propylene glycol. In some embodiments, a pharmaceutical composition or unit dosage form does not include ethanol. In some embodiments, a pharmaceutical composition or unit dosage form does not include propylene glycol or ethanol.

In some embodiments, a pharmaceutical composition or unit dosage form comprises a water-soluble polymer such as, but not limited to, homopolymers of N-polyvinylpyrrolidone (e.g., "povidone"), low molecular weight hydroxypropyl cellulose, low molecular weight methyl cellulose, low molecular weight hydroxypropyl methyl cellulose, and the like, and combinations thereof.

In some embodiments, after dilution a cyclodextrin derivative is present in the diluted pharmaceutical composition in a concentration of about 75 mM, about 100 mM, or about 125 mM.

In some embodiments, after dilution a nitrogen mustard, such as melphalan, mechlorethamine, cyclophosphamide, ifosfamide, bendamustine, etc., is present in the diluted pharmaceutical composition in a concentration of 0.1 mg/mL to 50 mg/mL, 0.15 mg/mL to 40 mg/mL, 0.2 mg/mL to 30 mg/mL, 0.3 mg/mL to 25 mg/mL, 0.4 mg/mL to 20 mg/mL, 0.45 mg/mL to 15 mg/mL, 0.5 mg/mL to 10 mg/mL, about 0.45 mg/mL, about 1 mg/mL, about 1.5 mg/mL, about 2 mg/mL, about 2.5 mg/mL, or about 5 mg/m L.

In some embodiments, a pharmaceutical composition and/or a diluent for use with a composition of the present disclosure is free of a solubilizing agent such as, but not limited to, water, an alcohol (e.g., ethanol and the like), a polyol (e.g., glycerol, propylene glycol, liquid polyethylene glycols, and the like), a vegetable oil, a nontoxic glyceryl ester, and combinations thereof. Thus, in some embodiments the diluent consists essentially of water and optional tonicity-adjusting agents (e.g., 0.9% saline solution for injection, and the like).

In some embodiments, the pH of a pharmaceutical composition or unit dosage form is controlled. In some embodiments, a pharmaceutical composition or unit dosage form comprises a pharmaceutically acceptable buffer and/or pH adjusting agent (e.g., an acidifying agent and/or alkalinizing agent). In some embodiments, a pharmaceutical composition or unit dosage form has a pH of about 4 to about 6, about 4 to about 5, about 5 to about 6, about 4, about 5, about 5.5, or about 6 after dilution with an aqueous diluent.

In some embodiments, a pharmaceutical composition or unit dosage form that is to be diluted prior to administration to a subject has a pH of about 2 to about 6, about 3 to about 6, about 4 to about 6, or about 5 to about 6. In some embodiments, after dilution (e.g., with an liquid carrier) a unit dosage form of the present disclosure has a pH of about 4 to about 6, about 4 to about 5, about 5 to about 6, about 4, about 4.5, about 5, about 5.5, or about 6 at the time of administration to a subject in need thereof.

In some embodiments, a composition that is to be lyophilized has a pH of about 2 to about 6, about 3 to about 6, about 4 to about 6, or about 5 to about 6. In some embodiments, after dilution (e.g., with an liquid carrier) a unit dosage form of the present disclosure has a pH of about 4 to about 6, about 4 to about 5, about 5 to about 6, about 4, about 4.5, about 5, about 5.5, or about 6 at the time of administration to a subject in need thereof.

In some embodiments, a pharmaceutical composition or unit dosage form comprises a buffer. In some embodiments, a pharmaceutical composition or unit dosage form comprises a buffer suitable to provide a dilute composition having a pH of about 4 to about 6, about 4 to about 5, about 5 to about 6, about 4, about 4.5, about 5 about 5.5, or about 6. In some embodiments, a buffer is present in a concentration of about 0.01 M to about 10 M, about 0.01 M to about 5 M, or about 0.01 M to about 1 M.

In some embodiments, a pharmaceutical composition or unit dosage form comprises a pH-adjusting agent such as, but not limited to, an acidifying agent (e.g., citric acid, HCl, and the like), an alkalinizing agent (e.g., NaOH and the like), a salt form of an acid (e.g., sodium citrate and the like), and combinations thereof. In some embodiments, a pharmaceutical composition or unit dosage form comprises a pH-adjusting agent in an amount sufficient to provide a dilute composition having a pH of about 4 to about 6, about 4 to about 5, about 5 to about 6, about 4, about 4.5, about 5 about 5.5, or about 6. In some embodiments, In some embodiments, a pharmaceutical composition or unit dosage form comprises sodium citrate in an amount of 50 mg to 500 mg, 75 mg to 400 mg, 100 mg to 300 mg, 150 mg to 250 mg, or about 200 mg.

In some embodiments, a pharmaceutical composition or unit dosage form comprises a second therapeutic agent. Suitable second therapeutic agents include, but are not limited to, a platinum compound, an antimetabolite, a nitrosourea, a corticosteroid, a calcineurin inhibitor, a monoclonal antibody, a polyclonal antibody, a cytotoxic antibiotic, an interferon, an opioid, an antihistamine, a volume expander, a pressor agent, and combinations thereof. Additional second therapeutic agents include, but are not limited to, doxorubicin, bortezomib, rituximab, thalidomide, lenalidomide, gemcitabine, thiotepa, fludarabine, carmustine, etoposide, cytarabine, granulocyte colony-stimulating factor, ADH-1, topotecan, palifermin, prednisone, arsenic trioxide, ascorbic acid, busulfan, buthionine sulfoximine, and combinations thereof.

As used herein, a "unit dosage form" refers to a composition containing a specific amount of a nitrogen mustard, such as melphalan, mechlorethamine, cyclophosphamide, ifosfamide, bendamustine, etc., the whole of which is intended to be administered to a subject in a single dose. A unit dosage form can be distinguished from a supply of a multi-dose amount of a pharmaceutical composition, e.g., a bottle of medicine, from which a unit dose is measured out.

In some embodiments, a unit dosage form of the present disclosure comprises a therapeutically effective amount of a nitrogen mustard, such as melphalan, mechlorethamine, cyclophosphamide, ifosfamide, bendamustine, etc. As used herein, a "therapeutically effective amount" refers to an amount of a nitrogen mustard, such as melphalan, mechlorethamine, cyclophosphamide, ifosfamide, bendamustine, etc., that elicits a biological or medicinal response in a tissue, system, animal or human that is being sought by a researcher, veterinarian, medical doctor or other clinician, which includes alleviation of the symptoms of a disease or disorder being treated.

A unit dosage form typically comprises the pharmaceutical composition of the present disclosure and optionally, one or more pharmaceutically acceptable excipients, wherein the amount of a nitrogen mustard, such as melphalan, mechlorethamine, cyclophosphamide, ifosfamide, bendamustine, etc., present in the unit dosage form is sufficient for a single administration to a subject in need thereof. Unit dosage forms include, but are not limited to, liquid solutions, liquid suspensions, liquid dispersions, emulsions, gels, powders, tablets, capsules, caplets, and the like. Treatment of a disease or condition amenable to treatment with a nitrogen mustard, such as melphalan, mechlorethamine, cyclophosphamide, ifosfamide, bendamustine, etc., can comprise periodic administration of a unit dosage form of the present disclosure, for example, once every two weeks, once every four weeks, or some other interval.

In some embodiments, a unit dosage form of the present disclosure comprises 25 mg to 125 mg, or 150 mg to 250 mg of melphalan as a hydrochloride salt. In some embodiments, a unit dosage form of the present disclosure comprises 50 mg or 200 mg melphalan as a hydrochloride salt.

In some embodiments, a unit dosage form of the present disclosure is a solid. In some embodiments, a solid unit dosage form of the present disclosure is a lyophilized solid or an aseptic spray-dried solid. In some embodiments, a dosage form of the present disclosure is suitable for dilution and/or reconstitution with a predetermined amount of a liquid carrier. For example, a unit dosage form (e.g., a liquid or a solid) of the present disclosure can be diluted with 5 mL to 500 mL, 10 mL to 100 mL, or 10 mL to 50 mL of a liquid carrier.

The pharmaceutical compositions and unit dosage forms are stable. As used herein, stability can refer to either the shelf-life of an undiluted solid or liquid dosage form or the resistance to degradation of a diluted liquid dosage form. In particular, currently available melphalan compositions suitable for intravenous administration must be used as soon as possible after dilution due to the rapid degradation of melphalan in aqueous solution. However, the dosage forms described herein are stable for a considerable time period after dilution, for example, at least 90 minutes up to at least 48 hours or more. Thus, in those embodiments in which a solid or liquid unit dosage form is diluted, the diluting can be performed immediately prior to administering, or sometime before the administering without any significant loss of therapeutic efficacy. This enables a liquid pharmaceutical composition or liquid unit dosage form of the present disclosure to be diluted 90 minutes to 48 hours in advance of use (i.e., in advance of parenteral administration to a subject in need thereof).

In some embodiments, the melphalan in a pharmaceutical composition of the present disclosure degrades by 2% or less at about 25° C. within 5 hours, or by 4% or less at about 25° C. within 10 hours after dilution with an aqueous diluent to provide a diluted composition comprising a cyclodextrin derivative in a concentration of about 75 mM or about 125 mM.

The primary degradation product of melphalan in aqueous solution is melphalan monohydroxide (also known as monohydroxymelphalan), which proceeds via a hydrolysis reaction. See, e.g., S. A. Stout et al., *Int. J. Pharm.* 24:193 (1985). In some embodiments, dilution of a pharmaceutical composition of the present disclosure provides a melphalan monohydroxide concentration (based on a 100% initial concentration of melphalan) of 2% or less within 5 hours of the diluting, when the diluted composition is maintained at room temperature (about 25° C.). In some embodiments, dilution of a pharmaceutical composition of the present disclosure provides a melphalan monohydroxide concentration (based on a 100% initial concentration of melphalan) of 4% or less within 10 hours of the diluting, when the diluted composition is maintained at room temperature (about 25° C.). In some embodiments, dilution of a pharmaceutical composition of the present disclosure provides a melphalan monohydroxide concentration (based on a 100% initial concentration of melphalan) of 2% or less within 24 hours of the diluting, or 4% or less within 48 hours of the diluting when the diluted composition is maintained at a temperature of about 10° C. or less.

Furthermore, the pharmaceutical compositions of the present disclosure can be stored prior to dilution for an extended period of time without any significant loss of melphalan. For example, a solid pharmaceutical composition comprising melphalan and a cyclodextrin derivative contains 2% or less, by weight, of a melphalan degradant after storage at 25° C. for a period of at least 2 years, or 5% or less, by weight, of a melphalan degradant after storage at 25° C. for a period of at least 3 years.

In some embodiments, a dry powder pharmaceutical composition of the present disclosure forms 2% or less of melphalan monohydroxide (based on a 100% initial concentration of melphalan) after storage for 2 years at room temperature.

Pharmaceutical Kits

The present disclosure is also directed to a pharmaceutical kit comprising a first container comprising 25 mg to 125 mg of a nitrogen mustard, such as melphalan, as a hydrochloride salt and an optional water-soluble polymer, and a second container comprising an aqueous diluent, an optional buffer, and a cyclodextrin derivative of formula I:

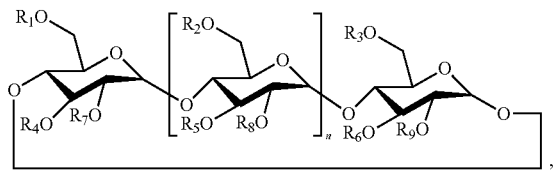

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group; wherein the cyclodextrin derivative is present in the second container in a concentration of at least 50:1 (w/w) relative to the a nitrogen mustard, such as melphalan, mechlorethamine, cyclophosphamide, ifosfamide, bendamustine, etc.; and wherein combining the first container and the second container provides a dilute pharmaceutical composition having a pH of about 4 to about 6 that degrades by 2% or less at about 25° C. within 5 hours after the diluting.

The present disclosure is also directed to a pharmaceutical kit comprising a first container comprising 150 mg to 250 mg of a nitrogen mustard, such as melphalan, as a hydrochloride salt and an optional water-soluble polymer; and a second container comprising an aqueous diluent, an optional buffer, and a cyclodextrin derivative of formula I:

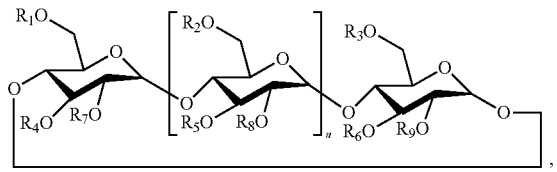

wherein n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$ $R_7$, $R_8$ and $R_9$ is a straight-chain or branched $C_1$-$C_8$-(alkylene)-$SO_3^-$ group; wherein the cyclodextrin derivative is present in the second container in a concentration of 25:1 to 35:1 (w/w) relative to the a nitrogen mustard, such as melphalan, mechlorethamine, cyclophosphamide, ifosfamide, bendamustine, etc.; and wherein combining the first container and the second container provides a dilute pharmaceutical composition having a pH of about 4 to about 6 that degrades by 2% or less at about 25° C. within 5 hours after the diluting.

Alternatively, a first container comprises a nitrogen mustard, such as melphalan, mechlorethamine, cyclophosphamide, ifosfamide, bendamustine, etc., (in an amount described above) and a cyclodextrin derivative (as described above), an optional water-soluble polymer (e.g., povidone and the like), and an optional pH-adjusting agent; and a second container comprises a diluent (e.g., water, saline, and the like), an optional tonicity adjusting agent, and an optional pH-adjusting agent.

Materials suitable for use as the containers with the kits of the present disclosure include, but are not limited to, a glass (e.g., borosilicate glass, amber glass, and the like), a plastic (e.g., polypropylene, high-density polyethylene, poly(ethylene terephthalate, polystyrene, polycarbonate, and the like, and combinations thereof), a metal (e.g., a foil), and the like, and combinations thereof (e.g., a plastic-coated glass and/or metal).

Containers suitable for use with the pharmaceutical kits of the present disclosure include, but are not limited to, vials, bottles, sachets, and the like. The containers can be opened and/or the contents can be removed therefrom, by, for example, tearing, cutting, removing a screw-top, removing a stopper, piercing, squeezing, and the like, and combinations thereof.

In some embodiments, a first container comprises povidone in an amount of 10 mg to 30 mg, 15 mg to 25 mg, or about 20 mg. In some embodiments, a second container comprises a pH-adjusting agent (e.g., an acidifying agent, an alkalinizing agent, and/or a buffer) in a concentration sufficient to provide a pH of about 4 to about 6 when the first container and the second container are combined. In some embodiments, a second container comprises sodium citrate in an amount of 50 mg to 500 mg, 75 mg to 400 mg, 100 mg to 300 mg, 150 mg to 250 mg, or about 200 mg.

In some embodiments, the cyclodextrin derivative present in the second container is a compound of formula II:

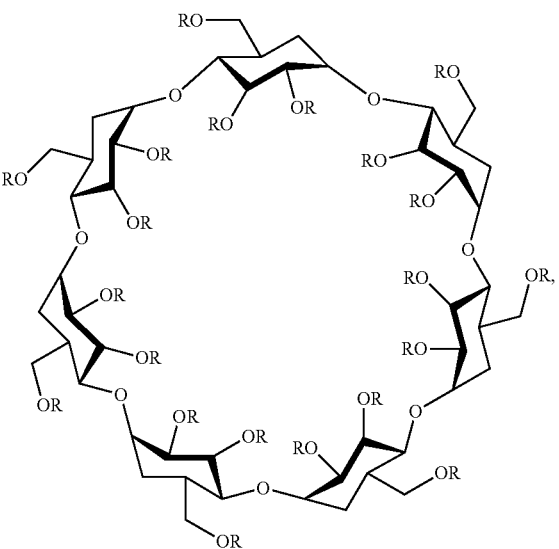

wherein 21-x of the R groups are H and x of the R groups are —$(CH_2)_4^-SO_3^-Na^+$, and x=6.0-7.1; wherein the first container comprises about 200 mg of a nitrogen mustard, such as melphalan, as a hydrochloride salt; and wherein the cyclodextrin derivative is present in the second container in an amount of about 27:1, about 30:1, or about 32:1 (w/w) relative to the a nitrogen mustard, such as melphalan, mechlorethamine, cyclophosphamide, ifosfamide, bendamustine, etc.

Methods of Administering and Treating

Some methods of treating a human being with a nitrogen mustard compound, such as melphalan, can comprise: administering a nitrogen mustard composition, such as a melphalan composition, intravenously to the human being. For these methods a nitrogen mustard composition, such as a melphalan composition, can prepared by reconstituting any solid pharmaceutical composition comprising a nitrogen mustard and a cyclodextrin derivative described herein using a pharmaceutically acceptable diluent. In some embodiments, the pharmaceutically acceptable diluent is normal saline.

A benefit of the method described in the paragraph above is that reconstitution can be rapid. For example, reconstitution can be conducted in about 1 second to about 5 minutes, about 1 second to about 2 minutes, or about 1 second to about 1 minute. Another advantage is that reconstitution can be carried out some time before the composition is administered to the human being. In some embodiments, the reconstituted composition is administered more than 1 hour, more than 2 hours, more than 4 hours, up to about 20 hours, up to about 24 hours, about 4 hours to about 24 hours, about 8 hours to about 12 hours, about 4 hours to about 8 hours, about 4 hours to about 20 hours, or about 8 hours to about 20 hours after reconstitution occurs. Another advantage is that the melphalan composition does not need to be reconstituted by a pharmacist.

In some embodiments, the human being that is being treated with a nitrogen mustard compound is suffering from a neoplastic disorder, such as multiple myeloma.

In some embodiments, the present disclosure is directed to methods of delivering a nitrogen mustard, such as melphalan, mechlorethamine, cyclophosphamide, ifosfamide, bendamustine, etc, to a subject in need thereof, the method comprising administering a pharmaceutical composition or unit dosage form comprising a nitrogen mustard to the subject in need thereof. The methods of the present disclosure include parenteral administration of the pharmaceutical compositions or unit dosage forms.

In some embodiments, the pharmaceutical compositions or unit dosage forms (or diluted forms thereof) are intravenously administered. Intravenous administration includes, but is not limited to, a bolus injection, an intravenous infusion, a limb perfusion, a normothermic isolated limb infusion, a percutaneous hepatic perfusion, and the like, and combinations thereof. Administering the compositions of the present disclosure can also be performed by injection and/or drip line using a cannula, a central line, a peripherally inserted central catheter line, and the like.

In some embodiments, a pharmaceutical composition of the present disclosure is administered as an infusion for a duration of 15 minutes to 6 hours, 30 minutes to 4 hours, 45 minutes to 3 hours, 1 hour to 2 hours, about 15 minutes, about 30 minutes, about 45 minutes, about 1 hour, about 1.5 hours, about 2 hours, about 2.5 hours, about 3 hours, about 4 hours, about 5 hours, or about 6 hours.

In some embodiments, the present disclosure is directed to parenterally administering a pharmaceutical composition or unit dosage form to a subject for which an oral composition of a nitrogen mustard, such as melphalan, is for one or more reasons, not appropriate. For example, oral compositions of a nitrogen mustard may not be appropriate because a subject may be too young, unable to swallow, undergoing surgery, incapacitated, or have a disorder that blocks absorption of a nitrogen mustard administered via the oral route. Further, parenteral administration of the pharmaceutical compositions of the present disclosure are useful for treating conditions in a subject in which a rapid increase in the in vivo concentration of a nitrogen mustard is required.

In some embodiments, the present disclosure is directed to a method of treating and or preventing diseases in a human subject by administering the pharmaceutical compositions and or unit dosage forms to the human subject. In some embodiments, the present disclosure is directed to methods of treating a subject suffering from a disease or disorder amenable to treatment with a nitrogen mustard, such as melphalan, mechlorethamine, cyclophosphamide, ifosfamide, bendamustine, etc. the method comprising administering a pharmaceutical composition or unit dosage form comprising the nitrogen mustard to the subject. As used herein the terms "treat," "treating," and "treatment" refer to administering a composition of the present disclosure prior to the onset of clinical symptoms of a disease state/condition so as to prevent the development of any symptom, as well as administering the composition after the onset of one or more clinical symptoms of a disease state/condition so as to reduce or eliminate any such symptom, aspect or characteristic of the disease state/condition. Such treating need not be absolute to be useful. Additionally, the terms "treat" and "treatment" refer to both therapeutic treatment and prophylactic, maintenance, or preventative measures, wherein the object is to prevent or slow down (lessen) an undesired physiological condition, disorder or disease, or obtain beneficial or desired clinical results. For purposes of this disclosure, beneficial or desired clinical results include, but are not limited to, alleviation of a symptom or a sign; diminishment of extent of a condition, disorder or disease; stabilization (i.e., not worsening) of the state of condition, disorder or disease; delay in onset or slowing of condition, disorder or disease progression; amelioration of a condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

As used herein, the term "subject" refers to warm blooded animals such as mammals, including humans and non-humans, such as, but not limited to, domestic and farm animals, zoo animals, sports animals, and pets (e.g., cats, dogs, mice, guinea pigs, horses, bovine cows, and sheep). In some embodiments, a subject is a human subject. Human subjects suitable for administering the pharmaceutical compositions and unit dosage forms include, but are not limited to, pediatric, adult, and geriatric subjects. In some embodiments of the disclosure, the subject is a pediatric subject. For example, according to the U.S. Food and Drug Administration, a "pediatric" subject is up to 21 years of age, and includes neonates (birth to about 1 month of age), infants (about 1 month to about 2 years of age), children (about 2 to about 12 years of age) and adolescents (about 12 to about 21 years of age). See *Guidance for Industry and FDA Staff, Premarket Assessment of Pediatric Medical Devices*, U.S. Dept. of Health and Human Services, Food and Drug Administration, Center for Devices and Radiological Health, and Center for Biologics Evaluation and Research (May 14, 2004). In some embodiments of the disclosure, the subject is an adult. As used herein, an "adult" subject is 18 years of age or older. In some embodiments, a subject is an adult that is about 50 years or older. In some embodiments of the disclosure, the subject is geriatric. Geriatric subjects are at least about 65 years of age. In some embodiments, a subject is about 70 years of age or older.

In some embodiments, the subject is a pediatric subject suffering from a disorder such as, but not limited to, an inborn defect, an immunodeficiency, a combined immunodeficiency, a severe combined immunodeficiency, a congenital neutropenia with defective stem cells, aplastic anemia, and combinations thereof In some embodiments, a subject is a geriatric subject scheduled to undergo a non-myeloablative procedure.

In some embodiments, the present disclosure comprises a method for treating a subject who has or is at risk for developing a condition amenable to treatment with melphalan, the method comprising administering an effective amount (i.e., a therapeutically effective amount) of a composition of the disclosure to the subject. Conditions amenable to treatment with melphalan include, but are not limited to, neoplastic disorders.

In some embodiments, a therapeutically effective amount for administering to a subject who has or is at risk for developing a condition amenable to treatment with melphalan is 25 mg to 125 mg, 40 mg to 110 mg, 40 mg to 75 mg, 40 mg to 60 mg, about 40 mg, about 50 mg, about 60 mg, about 75 mg, or about 100 mg of melphalan as a hydrochloride salt. The methods of the present disclosure also include titrating upward or downward from an initial melphalan dose in order to provide a therapeutically effective melphalan dosage. A therapeutically effective dose can be administered once, twice, thrice, four times, five times, six times, seven times, eight times, ten times, twelve times, or more as needed.

In some embodiments, the present disclosure is directed to a method of treating a disease, disorder or condition that is therapeutically responsive to a stem cell transplantation, the method comprising administering to a subject in need thereof a pharmaceutical composition or unit dosage form followed by the subject undergoing a stem cell transplantation.

In some embodiments, a method of the present disclosure comprises administering a pharmaceutical composition or unit dosage form (or diluted form thereof) to a subject that suffers from a disorder selected from: myeloma, multiple myeloma, acute myelogenous leukemia, malignant melanoma, metastatic melanoma (e.g., metastatic ocular melanoma, metastatic cutaneous melanoma, and the like), breast cancer, ovarian cancer, testicular cancer, advanced prostate cancer, a myelodysplastic syndrome, a neuroendocrine cancer (e.g., a metastatic neuroendocrine tumor, and the like), a metastatic adenocarcinoma tumor, a hepatocellular carcinoma, osteogenic sarcoma, polycythemia veraplasma, plasma cell neoplasm, amyloidosis, scleromyxedema, and combinations thereof.

In some embodiments, a method of the present disclosure comprises administering a pharmaceutical composition or unit dosage form (or diluted form thereof) to a subject for whom a stem cell transplantation has been indicated (e.g., a hematopoietic stem cell transplantation). In some embodiments, a subject for whom a stem cell transplantation has been indicated suffers from a disease or disorder selected from: a leukemia, a cancer, a non-malignant disease, and combinations thereof. In some embodiments, a subject for whom a stem cell transplantation has been indicated suffers from a disease or disorder selected from: myeloma, multiple myeloma, a lymphoma, non-Hodgkin lymphoma ("NHL"), leukemia, acute myeloid leukemia ("AML"), Hodgkin's disease, acute lymphoblastic leukemia ("ALL"), a myelodysplastic syndrome ("MDS"), a myeloproliferative disorder ("MPD"), chronic myelogenous leukemia ("CML"), neuroblastoma, aplastic anemia, chronic granulocytic leukemia, a neuroblastoma, sickle-cell disease, osteogenic sarcoma, Ewing's sarcoma, a desmoplastic small round cell tumor, plasma cell neoplasm, amyloidosis, scleromyxedema, and combinations thereof. In some embodiments, a subject for whom a stem cell transplantation has been indicated is a subject who would not benefit from prolonged treatment with, or is already resistant to, chemotherapy.

Thus, the pharmaceutical compositions and unit dosage forms are useful for treatment of a condition amenable to treatment with melphalan, as well as use for conditioning a subject in need thereof for receiving a stem cell transplantation.

The amount of the pharmaceutical composition that is administered is therapeutically effective for the treatment that is desired. For example, a therapeutically effective amount for the treatment of multiple myeloma refers to an amount which, when administered, diminishes one or more symptoms associated with this disorder.

In some embodiments, the present disclosure is directed to a method of conditioning a subject in order to conduct a stem cell transplantation, the method comprising administering an effective amount of a pharmaceutical composition or unit dosage of the disclosure (e.g., intravenously) to the subject. Thus, the pharmaceutical compositions and unit dosage forms are useful for treating a subject who suffers from a condition amenable to treatment by a stem cell transplant. As used herein, "stem cell transplantation" includes autologous and/or allogenic transplantation procedures.

The pharmaceutical compositions of the present disclosure are suitable for administering a nitrogen mustard, such as melphalan, in a "high-intensity" or myeloblative conditioning regimen in preparation for a stem cell transplantation, or in a "reduced intensity" conditioning regimen in preparation for a stem cell transplantation. As used herein, "reduced intensity" conditioning refers to dosages in which a nitrogen mustard, such as melphalan, dose of less than 150 $mg/m^2$ is administered to a subject at any one dose. In some embodiments, the pharmaceutical composition is administered to a subject that is 50 years of age or older who suffers from a condition amenable to treatment by a stem cell transplant.

In some embodiments, the melphalan is administered to a subject in need of a stem cell transplantation at a dose of 50 $mg/m^2$ to 300 $mg/m^2$, 50 $mg/m^2$ to 250 $mg/m^2$, 50 $mg/m^2$ to 225 $mg/m^2$, 50 $mg/m^2$ to 200 $mg/m^2$, 50 $mg/m^2$ to 175 $mg/m^2$, 50 $mg/m^2$ to 150 $mg/m^2$, 100 $mg/m^2$ to 300 $mg/m^2$, 100 $mg/m^2$ to 250 $mg/m^2$, 100 $mg/m^2$ to 225 $mg/m^2$, 100 $mg/m^2$ to 200 $mg/m^2$, 100 $mg/m^2$ to 175 $mg/m^2$, 100 $mg/m^2$ to 150 $mg/m^2$, 125 $mg/m^2$ to 300 $mg/m^2$, 125 $mg/m^2$ to 250 $mg/m^2$, 125 $mg/m^2$ to 225 $mg/m^2$, 125 $mg/m^2$ to 200 $mg/m^2$, 150 $mg/m^2$ to 300 $mg/m^2$, 150 $mg/m^2$ to 250 $mg/m^2$, 200 $mg/m^2$ to 300 $mg/m^2$, 200 $mg/m^2$ to 250 $mg/m^2$, about 50 $mg/m^2$, about 100 $mg/m^2$, about 125 $mg/m^2$, about 150 $mg/m^2$, about 175 $mg/m^2$, about 200 $mg/m^2$, about 250 $mg/m^2$, or about 300 $mg/m^2$.

In some embodiments, the administering comprises a dosage administered at four week intervals. In some embodiments, the dosage is administered twice, thrice, four times, five times, six times, eight times, or ten times. For example, in some embodiments a dose of about 100 $mg/m^2$ is administered three times with a four-week interval between the doses. In some embodiments, a dose of about 200 $mg/m^2$ is administered twice with a four-week interval between the doses. The final dose can be followed by a stem cell transplantation.

The pharmaceutical compositions and unit dosage forms can be administered alone or in conjunction with other medications or pharmaceutical compositions. In some embodiments, a method of the present disclosure comprises administering to a subject a second therapeutic agent selected from: an alkylating agent, a platinum compound, an antimetabolite, a nitrosourea, a corticosteroid, a calcineurin inhibitor, a monoclonal antibody, a polyclonal antibody, a cytotoxic antibiotic, an interferon, an opioid, an antihistamine, a volume expander, a pressor agent, and combinations thereof. Additional second therapeutic agents include, but are not limited to, cisplatin, carboplatin, doxorubicin, bortezomib, rituximab, thalidomide, lenalidomide, gemcitabine, thiotepa, fludarabine, carmustine, etoposide, cytarabine, granulocyte colony-stimulating factor (G-CSF), ADH-1, topotecan, paliferm in, prednisone, arsenic trioxide, ascorbic acid, busulfan, cyclophosphamide, N,N',N"-triethylenethiophosphoramide, buthionine sulfoximine, and combinations thereof. A second therapeutic agent can be administered to a subject either in a pharmaceutical composition or unit dosage form that includes at least one additional therapeutic agent (in addition to a nitrogen mustard), or as a separate pharmaceutical composition or unit dosage.

In some embodiments, the pharmaceutical compositions and/or unit dosage forms are administered with other combinations of therapeutic active agents such as, but not limited to, carmustine, etoposide and cytarabine; busulfan and thiotepa; doxorubicin and bortezomib; arsenic trioxide and citric acid; thalidomide and rituximab; thalidomide and prednisone; and busulfan, fludarabine and G-CSF.

In some embodiments, the pharmaceutical compositions and unit dosage forms can enhance the bioavailability, rate of therapeutic onset, and/or therapeutic efficacy of a nitrogen mustard. Thus, the present disclosure is also directed to a method of decreasing the time to therapeutic onset of a nitrogen mustard following administration thereof, the method comprising orally or parenterally administering to a subject in need thereof a pharmaceutical composition or unit dosage form, wherein the time to therapeutic onset of a nitrogen mustard provided by the orally or parenterally administered composition or unit dosage is less than the time to therapeutic onset of a nitrogen mustard provided by an orally administered reference composition that excludes the cyclodextrin derivative and contains an equivalent dose of the nitrogen mustard. In some embodiments, the time to therapeutic onset of the nitrogen mustard following administration of a pharmaceutical composition or unit dosage form is reduced by at least 5%, at least 10%, at least 15%, at least 20%, at least 25%, at least 30%, at least 40%, or at least 50% compared to the time to therapeutic onset of the nitrogen mustard provided by an intravenously administered reference composition that excludes the cyclodextrin derivative and contains an equivalent dose of the nitrogen mustard.

In some embodiments, the dissolution of a nitrogen mustard from the dosage forms can be related to pharmacokinetic parameters and/or the in vivo concentration of a nitrogen mustard and/or its metabolite(s). The in vivo concentration of a nitrogen mustard and its metabolite(s), as well as pharmacokinetic parameters associated with an active form of a nitrogen mustard can be determined by, e.g., sampling the blood plasma of a subject after administering a composition of the present disclosure. Pharmacokinetic parameters that can be measured include, but are not limited to, $AUC_{0-t}$, $AUC_{t-\infty}$, $AUC_{0-\infty}$, and $\ln(AUC_{LAST})$.

As used herein, "$AUC_{0-t}$" refers to the Area Under the Concentration time curve (i.e., plot of plasma concentration vs. time) after nitrogen mustard administration. The area is conveniently determined by the "trapezoidal rule": the data points are connected by straight line segments, perpendiculars are erected from the abscissa to each data point, and the sum of the areas of the triangles and trapezoids so constructed is computed.

As used herein, "$AUC_{t-\infty}$" refers to the Area Under the Concentration time curve, wherein the last concentration is extrapolated to baseline based on the rate constant for elimination.

As used herein, "$AUC_{0-\infty}$" refers to the sum of the Area Under the Concentration time curves for $AUC_{0-t}$ and $AUC_{t-\infty}$.

As used herein, "$\ln(AUC_{LAST})$" refers to the Area Under the Concentration time curve determined by plotting plasma concentration on a natural logarithmic scale, using the last measured plasma concentration as the end point.

As used herein, "IntraCV" refers to an intra-assay coefficient of variation, which is the standard deviation within a sample set divided by the mean value of the sample set, with the result reported as a percentage.

In some embodiments, the bioavailability of melphalan in a human subject from a composition of the present disclosure is substantially greater than that observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)). For example, the dosage forms can have an $AUC_{0-t}$ or $AUC_{0-\infty}$ that is at least 20% or greater, at least 25% or greater, at least 30% or greater, at least 40% or greater, at least 50% or greater, at least 60% or greater, or at least 70% or greater than the $AUC_{0-t}$ or $AUC_{0-\infty}$ observed after administration of a melphalan formulation to a subject that contains the same amount of melphalan and lacks a cyclodextrin derivative (e.g., ALKERAN® for Injection (GlaxoSmithKline) or Melphalan HCl Injectable (Bioniche Pharma USA)).

In some embodiments, the bioavailability of melphalan from a composition of the present disclosure is greater than that observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)). For example, the dosage forms can have an $AUC_{0-t}$ or $AUC_{0-\infty}$ that is at least 20% or greater, at least 25% or greater, at least 30% or greater, at least 40% or greater, at least 50% or greater, at least 60% or greater, or at least 70% or greater than the $AUC_{0-t}$ or $AUC_{0-\infty}$ observed after administration of a melphalan formulation to a subject that contains the same amount of melphalan and lacks a cyclodextrin derivative (e.g., ALKERAN® for Injection (GlaxoSmithKline) or Melphalan HCl Injectable (Bioniche Pharma USA)). In some embodiments, the $AUC_{0-t}$ or $AUC_{0-\infty}$ of melphalan from a composition of the present disclosure is 20% to 70%, 20% to 60%, 20% to 50%, 30% to 70%, 30% to 60%, 30% to 50%, 40% to 70%, 40% to 60%, or 50% to 70% greater than the $AUC_{0-t}$ or $AUC_{0-\infty}$ observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)).

In some embodiments, the maximum plasma concentration ($C_{max}$) of melphalan from a composition of the present disclosure is at least 20% or greater, at least 25% or greater, at least 30% or greater, at least 40% or greater, at least 50% or greater, at least 60% or greater, or at least 70% or greater than a $C_{max}$ observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)). In some embodiments, the maximum plasma concentration ($C_{max}$) of melphalan from a composition of the present disclosure is 20% to 70%, 20% to 60%, 20% to 50%, 30% to 70%, 30% to 60%, 30% to 50%, 40% to 70%, 40% to 60%, or 50% to 70% greater than a $C_{max}$ observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)).

In some embodiments, the rate of therapeutic onset of melphalan from a composition of the present disclosure is faster than that observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)). For example, the dosage forms have a time to $C_{max}$ (i.e., $t_{max}$) that is about 5%, about 10%, about 15%, about 20%, about 25%, or about 30% faster, or about 35% faster than a $t_{max}$ observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)). In some embodiments, the dosage forms have a time to $C_{max}$ (i.e., $t_{max}$) that is 5% to 35%, 5% to 30%, 5% to 25%, 5% to 20%, 10% to 35%, 15% to 35%, 20% to 35%, or 25% to 30% faster than a $t_{max}$ observed upon administration of an equivalent dose of melphalan from a formulation lacking a cyclodextrin derivative (e.g., ALKERAN® for Injection (GlaxoSmithKline) or Melphalan HCl Injectable (Bioniche Pharma USA)).

In some embodiments, the pharmaceutical compositions of the present disclosure provide a reduced rate of hypersensitivity in patients after parenteral administration compared with patients parenterally administered a similar dose of melphalan without a cyclodextrin derivative.

In some embodiments, the pharmaceutical compositions of the present disclosure provide a reduced rate of severe myelotoxicity in patients (e.g., patients who experience a white blood cell count <1,000 per mL and/or platelet count <25,000) after parenteral administration compared with patients parenterally administered a similar dose of melphalan without a cyclodextrin derivative.

In some embodiments, the pharmaceutical compositions of the present disclosure provide a reduced rate of death in patients after parenteral administration compared with patients parenterally administered a similar dose of melphalan without a cyclodextrin derivative.

Having generally described the disclosure, a further understanding can be obtained by reference to the examples provided herein. These examples are given for purposes of illustration only and are not intended to be limiting.

The following is a listing of embodiments that are specifically contemplated herein.

Embodiment 1. A method of treating a subject suffering from a neoplastic disorder, the method comprising:
diluting a composition with an aqueous diluent to provide a dilute pharmaceutical composition comprising 25 mg to 125 mg of melphalan and a cyclodextrin derivative of formula I:

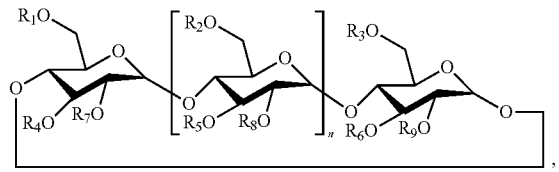

wherein n is 4, 5 or 6;

wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group;

wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3$— group;

wherein the dilute pharmaceutical composition has a pH of about 4 to about 6; wherein the cyclodextrin derivative is present in a concentration of at least 50:1 (w/w) relative to the melphalan;

wherein the melphalan in the dilute pharmaceutical composition degrades by 2% or less at about 25° C. within 5 hours after the diluting; and administering the dilute pharmaceutical composition by injection to the subject in need thereof.

Embodiment 2. The method of embodiment 1, wherein the neoplastic disorder is selected from: myeloma, multiple myeloma, melanoma, acute myelogenous leukemia, malignant melanoma, breast cancer, ovarian cancer, testicular cancer, advanced prostate cancer, a neuroendocrine cancer, metastatic melanoma, a metastatic neuroendocrine tumor, a metastatic adenocarcinoma tumor, hepatocellular carcinoma, osteogenic sarcoma, polycythemia veraplasma, plasma cell neoplasm, amyloidosis, scleromyxedema, and combinations thereof.

Embodiment 3. The method of embodiment 2, wherein the neoplastic disorder is multiple myeloma and the administering is systemic and provides palliative treatment of the multiple myeloma.

Embodiment 4. The method of embodiment 1, wherein at least one of $R_1$, $R_2$, $R_3$, $R_4$, $R_5$, $R_6$, $R_7$, $R_8$ and $R_9$ is a hydroxy-substituted-$C_3$ group.

Embodiment 5. The method of embodiment 1, wherein $R_1$, $R_2$, $R_3$, $R_4$, $R_5$, $R_6$, $R_7$, $R_8$ and $R_9$ are independently a straight-chain or branched $C_1$-$C_8$-(alkylene)-$SO_3^-$ group having a degree of substitution of 4 to 8 per cyclodextrin derivative, and the remaining substituents are —H.

Embodiment 6. The method of embodiment 1, wherein at least one of $R_1$, $R_2$, $R_3$, $R_4$, $R_5$, $R_6$, $R_7$, $R_8$ and $R_9$ is substituted with a straight-chain $C_4$-(alkylene)-$SO_3^-$ group.

Embodiment 7. The method of embodiment 1, wherein the cyclodextrin derivative is a compound of formula II:

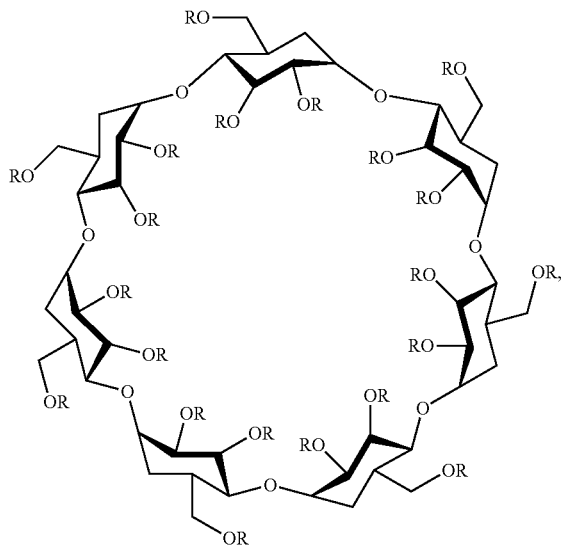

wherein 21-x of the R groups are H and x of the R groups are —$(CH_2)_4$-$SO_3^-$$Na^+$, and x=6.0-7.1;
wherein the pharmaceutical composition comprises about 50 mg of melphalan as a hydrochloride salt; and
wherein the cyclodextrin derivative is present in a concentration of 50:1 to 100:1 (w/w) relative to the melphalan.

Embodiment 8. The method of embodiment 1, wherein the dilute pharmaceutical composition is substantially free of an alcohol.

Embodiment 9. The method of embodiment 1, wherein the aqueous diluent is a saline solution.

Embodiment 10. The method of embodiment 1, wherein the subject suffering from the neoplastic disorder is a pediatric subject.

Embodiment 11. The method of embodiment 1, wherein the melphalan in the dilute pharmaceutical composition degrades by 4% or less at 25° C. within 10 hours after the diluting.

Embodiment 12. The method of embodiment 1, wherein the dilute pharmaceutical composition is stored about 0.5 hours to about 18 hours prior to the administering.

Embodiment 13. The method of embodiment 1, wherein the administering provides a melphalan $C_{max}$ in the subject suffering from a neoplastic disorder that is at least 20% or greater than a melphalan $C_{max}$ provided by a melphalan formulation containing an equivalent dose of melphalan and lacking the cyclodextrin derivative.

Embodiment 14. The method of embodiment 1, wherein the administering provides a melphalan $AUC_{0-t}$ in the subject suffering from a neoplastic disorder that is at least 20% or greater than a melphalan $AUC_{0-t}$ provided by a melphalan formulation containing an equivalent dose of melphalan and lacking the cyclodextrin derivative.

Embodiment 15. A method for conditioning a subject for whom a stem cell transplantation has been indicated, the method comprising:
administering a melphalan dose of 50 mg/m² to 300 mg/m² per day to the subject for whom a stem cell transplantation has been indicated, wherein the melphalan dose is administered in a pharmaceutical composition comprising melphalan and a cyclodextrin derivative of formula I:

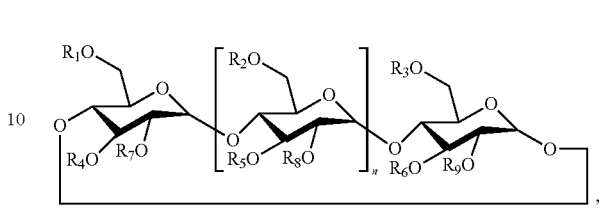

wherein n is 4, 5 or 6;
wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group;
wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group;
wherein the pharmaceutical composition has a pH of about 4 to about 6; and
wherein the cyclodextrin derivative is present in a ratio of at least 25:1 (w/w) relative to the melphalan.

Embodiment 16. The method of embodiment 15, wherein the administering is for a period of two or more days.

Embodiment 17. The method of embodiment 15, wherein the subject in need of the stem cell transplantation is a pediatric subject.

Embodiment 18. The method of embodiment 15, wherein the administering is performed intravenously.

Embodiment 19. The method of embodiment 15, wherein the administering is performed via a limb perfusion.

Embodiment 20. The method of embodiment 15, wherein at least one of $R_1$, $R_2$, $R_3$, $R_4$, $R_5$, $R_6$, $R_7$, $R_8$ and $R_9$ is a hydroxy-substituted-$C_3$ group.

Embodiment 21. The method of embodiment 15, wherein the cyclodextrin derivative is a compound of formula II

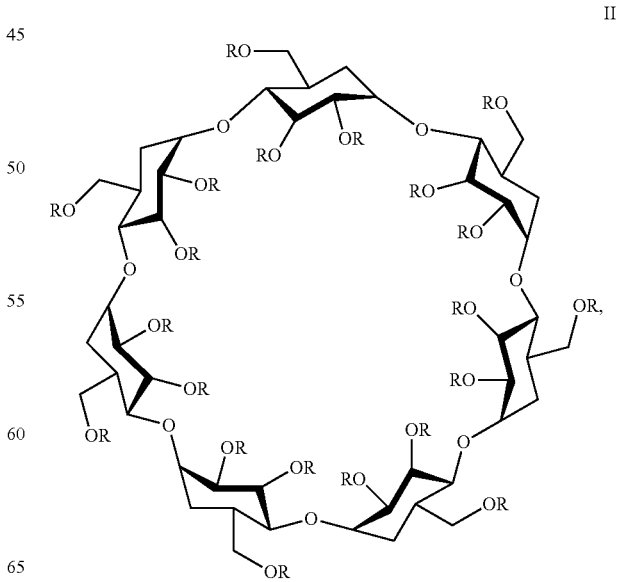

wherein 21-x of the R groups are H and x of the R groups are —(CH$_2$)$_4$-SO$_3^-$ Na$^+$, and x=6.0-7.1;

wherein the pharmaceutical composition comprises about 200 mg of melphalan as a hydrochloride salt; and wherein the cyclodextrin derivative is present in a ratio of 25:1 to 35:1 (w/w) relative to the melphalan.

Embodiment 22. The method of embodiment 15, wherein the subject for whom a stem cell transplantation has been indicated suffers from a disease or disorder selected from: myeloma, multiple myeloma, a lymphoma, non-Hodgkin lymphoma, leukemia, acute myeloid leukemia, Hodgkin's disease, acute lymphoblastic leukemia, a myelodysplastic syndrome, a myeloproliferative disorder, chronic myelogenous leukemia, neuroblastoma, aplastic anemia, chronic granulocytic leukemia, a neuroblastoma, sickle-cell disease, osteogenic sarcoma, Ewing's sarcoma, a desmoplastic small round cell tumor, plasma cell neoplasm, amyloidosis, scleromyxedema, and combinations thereof.

Embodiment 23. The method of embodiment 15, comprising diluting a concentrated melphalan composition with an aqueous diluent to provide the pharmaceutical composition.

Embodiment 24. The method of embodiment 23, wherein the concentrated melphalan composition comprises 50 mg to 500 mg of melphalan.

Embodiment 25. The method of embodiment 23, wherein the concentrated melphalan composition comprises about 200 mg.

Embodiment 26. The method of embodiment 15, wherein the pharmaceutical composition is substantially free of an alcohol.

Embodiment 27. The method of embodiment 23, wherein the aqueous diluent is a saline solution.

Embodiment 28. The method of embodiment 23, wherein the melphalan in the pharmaceutical composition degrades by 4% or less at about 25° C. within 10 hours after the diluting.

Embodiment 29. The method of embodiment 23, wherein the pharmaceutical composition is stored about 0.5 hours to about 12 hours prior to the administering.

Embodiment 30. The method of embodiment 15, wherein the administering provides a melphalan C$_{max}$ in the subject for whom a stem cell transplantation has been indicated that is at least 20% or greater than a melphalan C$_{max}$ provided by a melphalan formulation containing an equivalent dose of melphalan and lacking the cyclodextrin derivative.

Embodiment 31. The method of embodiment 15, wherein the administering provides a melphalan AUC$_{0-t}$ in the subject for whom a stem cell transplantation has been indicated that is at least 20% or greater than a melphalan AUC$_{0-t}$ provided by a melphalan formulation containing an equivalent dose of melphalan and lacking the cyclodextrin derivative.

Embodiment 32. A pharmaceutical composition comprising:

25 mg to 125 mg of melphalan as a hydrochloride salt;

an optional buffer; and a cyclodextrin derivative of formula I:

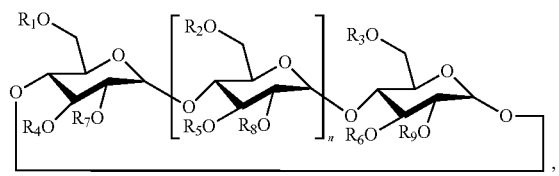

wherein n is 4, 5 or 6;

wherein R$_1$, R$_2$, R$_3$, R$_4$, R$_5$, R$_6$, R$_7$, R$_8$ and R$_9$ are independently —H, a straight-chain or branched C$_1$-C$_8$-(alkylene)-SO$_3^-$ group, or an optionally substituted straight-chain or branched C$_1$-C$_6$ group;

wherein at least one of R$_1$, R$_2$, R$_3$, R$_4$, R$_5$, R$_6$, R$_7$, R$_8$ and R$_9$ is a straight-chain or branched C$_1$-C$_8$-(alkylene)-SO$_3^-$ group;

wherein the pharmaceutical composition has a pH of about 4 to about 6, wherein dilution of the pharmaceutical composition with an aqueous solution provides a dilute pharmaceutical composition in which the melphalan degrades by 2% or less at about 25° C. within 5 hours after the dilution; and wherein the cyclodextrin derivative is present in a ratio of 50:1 to 100:1 (w/w) relative to the melphalan.

Embodiment 33. The pharmaceutical composition of embodiment 32, wherein at least one of R$_1$, R$_2$, R$_3$, R$_4$, R$_5$, R$_6$, R$_7$, R$_8$ and R$_9$ is a hydroxy-substituted-C$_3$ group.

Embodiment 34. The pharmaceutical composition of embodiment 32, wherein the cyclodextrin derivative is a compound of formula II:

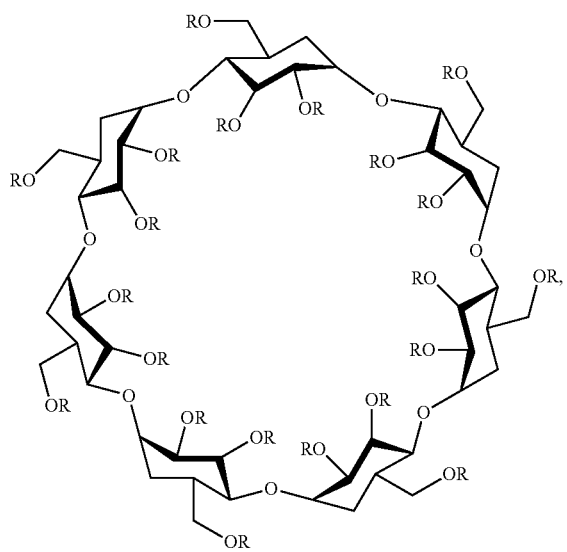

wherein 21-x of the R groups are H and x of the R groups are —(CH$_2$)$_4$-SO$_3^-$Na$^+$, and x=6.0-7.1;

wherein the pharmaceutical composition comprises about 50 mg of melphalan as a hydrochloride salt; and wherein the cyclodextrin derivative is present in a ratio of about 55:1 (w/w) relative to the melphalan.

Embodiment 35. A pharmaceutical composition comprising:
150 mg to 250 mg of melphalan as a hydrochloride salt;
an optional buffer; and
a cyclodextrin derivative of formula I:

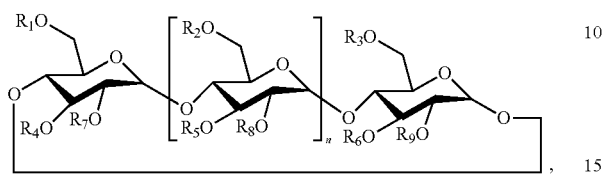

wherein n is 4, 5 or 6;
wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group;
wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group;
wherein the pharmaceutical composition has a pH of about 4 to about 6,
wherein dilution of the pharmaceutical composition with an aqueous solution provides a melphalan solution in which the melphalan degrades by 2% or less at about 25° C. within 5 hours after the dilution; and
wherein the cyclodextrin derivative is present in a ratio of 25:1 to 35:1 (w/w) relative to the melphalan.

Embodiment 36. The pharmaceutical composition of embodiment 35, wherein at least one of $R_1$, $R_2$, $R_3$, $R_4$, $R_5$, $R_6$, $R_7$, $R_8$ and $R_9$ is a hydroxy-substituted-$C_3$ group.

Embodiment 37. The pharmaceutical composition of embodiment 35, wherein the cyclodextrin derivative is a compound of formula II:

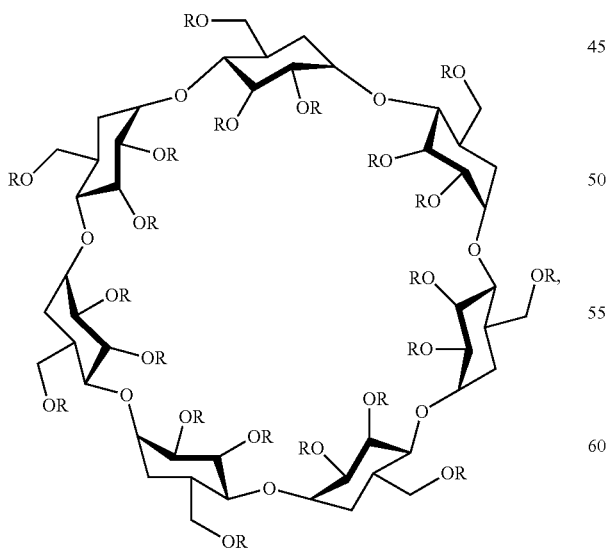

wherein 21-x of the R groups are H and x of the R groups are —$(CH_2)_4$-$SO_3^-Na^+$, and x=6.0-7.1;

wherein the pharmaceutical composition comprises about 200 mg of melphalan as a hydrochloride salt; and
wherein the cyclodextrin derivative is present in a ratio of about 30:1 (w/w) relative to the melphalan.

Embodiment 38. A pharmaceutical kit comprising:
a first container comprising 25 mg to 125 mg of melphalan as a hydrochloride salt and an optional water-soluble polymer; and
a second container comprising an aqueous diluent, an optional buffer, and a cyclodextrin derivative of formula I:

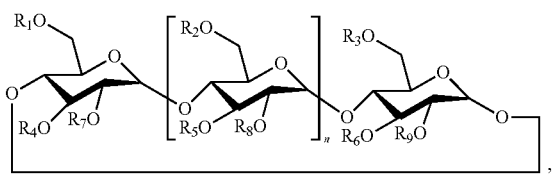

wherein n is 4, 5 or 6;
wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group;
wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group;
wherein the cyclodextrin derivative is present in the second container in a concentration of at least 50:1 (w/w) relative to the melphalan; and
wherein combining the first container and the second container provides a dilute pharmaceutical composition having a pH of about 4 to about 6 that degrades by 2% or less at about 25° C. within 5 hours after the diluting.

Embodiment 39. The pharmaceutical kit of embodiment 38, wherein the first container comprises povidone in an amount of 10 mg to 30 mg, and the second container comprises a pH-adjusting agent in a concentration sufficient to provide a pH of about 4 to about 6 when the first container and the second container are combined.

Embodiment 40. A pharmaceutical kit comprising:
a first container comprising 150 mg to 250 mg of melphalan as a hydrochloride salt and an optional water-soluble polymer; and
a second container comprising an aqueous diluent, an optional buffer, and a cyclodextrin derivative of formula I:

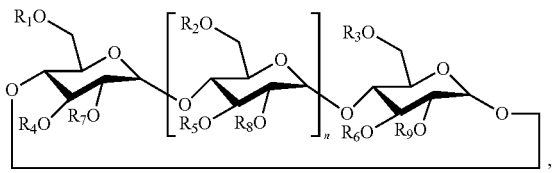

wherein n is 4, 5 or 6;

wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group;

wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group;

wherein the cyclodextrin derivative is present in the second container in a concentration of 25:1 to 35:1 (w/w) relative to the melphalan; and wherein combining the first container and the second container provides a dilute pharmaceutical composition having a pH of about 4 to about 6 that degrades by 2% or less at about 25° C. within 5 hours after the diluting.

Embodiment 41. The pharmaceutical kit of embodiment 40, wherein the first container comprises povidone in an amount of 10 mg to 30 mg, and the second container comprises a pH-adjusting agent in a concentration sufficient to provide a pH of about 4 to about 6 when the first container and the second container are combined.

Embodiment 42. The pharmaceutical kits of embodiment 40, wherein the cyclodextrin derivative is a compound of formula II:

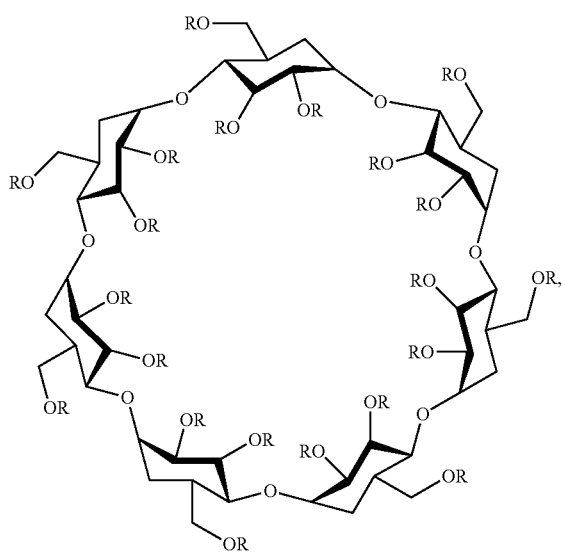

II wherein 21-x of the R groups are H and x of the R groups are —$(CH_2)_4$-$SO_3^-$ $Na^+$, and x=6.0-7.1;

wherein the first container comprises about 200 mg of melphalan as a hydrochloride salt; and wherein the cyclodextrin derivative is present in the second container in an amount of about 30:1 (w/w) relative to the melphalan.

Embodiment 43. A pharmaceutical product comprising a nitrogen mustard compound and a water-soluble cyclodextrin derivative in a single vial, wherein the product does not include propylene glycol or ethanol.

Embodiment 44. The pharmaceutical product of embodiment 43, wherein the nitrogen mustard compound is melphalan.

Embodiment 45. The pharmaceutical product of embodiment 44, wherein the water-soluble cyclodextrin derivative and melphalan have a weight ratio of at least about 50:1.

Embodiment 46. The pharmaceutical product of embodiment 44 or 45, wherein melphalan and the water-soluble cyclodextrin are present in a solid.

Embodiment 47. The pharmaceutical product of embodiment 44, 45, or 46, wherein the vial contains about 50 mg of melphalan.

Embodiment 48. The pharmaceutical product of embodiment 43, 44, 45, 46, or 47, wherein the vial contains about 2500 mg to about 3000 mg of the water-soluble cyclodextrin derivative.

Embodiment 49. The pharmaceutical product of embodiment 43, 44, 45, 46, 47, or 48, wherein the water-soluble cyclodextrin derivative is an (SBE)-β-cyclodextrin.

Embodiment 50. The pharmaceutical product of embodiment 43, 44, 45, 46, 47, 48, or 49, wherein the water-soluble cyclodextrin derivative is $(SBE)_{6.5\ m}$-β-cyclodextrin.

Embodiment 51. A method of treating a human being with melphalan comprising:
administering a melphalan composition intravenously to the human being;
wherein the melphalan composition is prepared by reconstituting contents of the vial of the pharmaceutical product according to embodiment 43, 44, 45, 46, 47, 48, 49, or 50 using a pharmaceutically acceptable diluent;
wherein the reconstituting is conducted in about 1 second to about 5 minutes; and
wherein the melphalan composition is administered more than 1 hour after the melphalan composition is reconstituted.

Embodiment 52. The method of embodiment 51, wherein the pharmaceutically acceptable diluent is normal saline.

Embodiment 53. The method of embodiment 51 or 52, wherein the melphalan composition is administered up to about 24 hours after the melphalan composition is reconstituted.

Embodiment 54. The method of embodiment 51 or 52, wherein the melphalan composition is administered about 4 hours to about 24 hours after the melphalan composition is reconstituted.

Embodiment 55. The method of embodiment 51 or 52, wherein the melphalan composition is administered about 8 hours to about 20 hours after the melphalan composition is reconstituted.

Embodiment 56. The method of embodiment 51, 52, 53, 54, or 55, wherein the melphalan composition is not reconstituted by a pharmacist.

Embodiment 57. The method of embodiment 51, 52, 53, 54, 55, or 56, wherein the melphalan composition has a pH of about 5 to about 5.5.

Embodiment 58. The method of embodiment 51, 52, 53, 54, 55, 56, or 57, wherein the human being is suffering from a neoplastic disorder.

Embodiment 59. The method of embodiment 58, wherein the human being is suffering from multiple myeloma.

Embodiment 60. A pharmaceutical product comprising a nitrogen mustard compound and a water-soluble cyclodextrin derivative in a single vial, wherein the product does not include propylene glycol or ethanol.

Embodiment 61. The pharmaceutical product of embodiment 60, wherein the nitrogen mustard compound is melphalan.

Embodiment 62. The pharmaceutical product of embodiment 61, wherein the water-soluble cyclodextrin derivative and melphalan have a weight ratio of at least about 50:1.

Embodiment 63. The pharmaceutical product of embodiment 61 or 62, wherein melphalan and the water-soluble cyclodextrin are present in a solid.

Embodiment 64. The pharmaceutical product of embodiment 61, 62, or 63, wherein the vial contains about 50 mg of melphalan.

Embodiment 65. The pharmaceutical product of embodiment 61, 62, 63, or 64, wherein the vial contains about 2500 mg to about 3000 mg of the water-soluble cyclodextrin derivative.

Embodiment 66. The pharmaceutical product of embodiment 61, 62, 63, 64, or 65, wherein the water-soluble cyclodextrin derivative is an (SBE)-β-cyclodextrin.

Embodiment 67. The pharmaceutical product of embodiment 61, 62, 63, 64, 65, or 66, wherein the water-soluble cyclodextrin derivative is $(SBE)_{6.5\ m}$-β-cyclodextrin.

Embodiment 68. A method of treating a human being with melphalan comprising:
administering a melphalan composition intravenously to the human being;
wherein the melphalan composition is prepared by reconstituting contents of the vial of the pharmaceutical product according to any one of embodiments 60-67 using a pharmaceutically acceptable diluent;
wherein the reconstituting is conducted in about 1 second to about 5 minutes; and
wherein the melphalan composition is administered more than 1 hour after the melphalan composition is reconstituted.

Embodiment 69. The method of embodiment 68, wherein the pharmaceutically acceptable diluent is normal saline.

Embodiment 70. The method of embodiment 68 or 69, wherein the melphalan composition is administered up to about 24 hours after the melphalan composition is reconstituted.

Embodiment 71. The method of embodiment 68 or 69, wherein the melphalan composition is administered about 4 hours to about 24 hours after the melphalan composition is reconstituted.

Embodiment 72. The method of embodiment 68 or 69, wherein the melphalan composition is administered about 8 hours to about 20 hours after the melphalan composition is reconstituted.

Embodiment 73. The method of any of embodiments 68-72, wherein the melphalan composition is not reconstituted by a pharmacist.

Embodiment 74. The method of any of embodiments 68-73 wherein the melphalan composition has a pH of about 5 to about 5.5.

Embodiment 75. The method of any of embodiments 68-74, wherein the human being is suffering from a neoplastic disorder.

Embodiment 76. The method of embodiment 75, wherein the human being is suffering from multiple myeloma.

EXAMPLES

Example 1

The dissolution rate of free-base melphalan (Chemwerth, Woodbridge, Conn.) in solutions at various pH and at various concentrations of a cyclodextrin derivative were examined. The procedure was as follows: free base melphalan was added to a solution containing a cyclodextrin derivative ($SBE_{6.5}$-β-CD, CAPTISOL®) and then vortex mixed for 1-5 minutes, and, if necessary, sonicated in ice water until a clear solution was achieved.

TABLE

Dissolution times for free base melphalan as a function of cyclodextrin derivative concentration, volume, and pH.

| Target Melphalan Conc. | $SBE_{6.5}$-β-CD Conc. | Volume | pH | Dissolution Time (min) |
|---|---|---|---|---|
| 50 mg/mL | 200 mM | 5 mL | 5 | 50 |
| 50 mg/mL | 125 mM | 6 mL | 5 | 90 |
| 50 mg/mL | 100 mM | 7 mL | 5 | 160 |
| 50 mg/mL | 75 mM | 8 mL | 5 | >180 |
| 50 mg/mL | 50 mM | 10 mL | 5 | 360 |
| 50 mg/mL | 125 mM | 6 mL | 2.7 | 75 |
| 50 mg/mL | 125 mM | 10 mL | 1.8 | 16 |
| 50 mg/mL | 125 mM | 6 mL | 1.3 | 5 |
| 50 mg/mL | 75, 100 125 mM | 10 mL | 1.1 | <5 for all |

Referring to the data in the above Table, the dissolution of free base melphalan was very rapid at pH 1.1 regardless of the concentration of the cyclodextrin derivative. After dissolution, the solution was then neutralized with sodium hydroxide.

The solutions of free base melphalan in this example can be prepared by addition of free base melphalan to a solution that contains the cyclodextrin derivative, or by adding a 0.1 M HCl solution to the melphalan and then adding the cyclodextrin derivative, or dissolving the free base melphalan and cyclodextrin derivative simultaneously. However, sonication was superior to mixing and/or shaking for dissolution enhancement and de-clumping of dry material in solution.

Example 2

The binding of free-base melphalan (Chemwerth, Woodbridge, Conn.) was studied as a function of cyclodextrin derivative concentration at pH 5 and pH 7, and the data was compared with literature reports of free-base melphalan binding. The pH 5 solutions contained 100 mM sodium bitartrate buffer, and was adjusted to pH 5 using sodium hydroxide in 0.9% sodium chloride solution. The pH 7 solutions contained 50 mM each of mono- and di-basic phosphate and 0.9% sodium chloride. Solutions containing 0, 50, 75 and 100 mM $SBE_{6.5}$-β-CD (CAPTISOL®) were prepared, and excess free base melphalan was added to 2 mL samples of each solution. After the addition of free base melphalan, the samples were vortex mixed for 30 seconds, sonicated in ice water bath for 20 minutes, and then mixed by end-over-end rotation at room temperature for 30 minutes. The samples were then centrifuged, the clear supernatant was diluted with water, and analyzed by HPLC.

All melphalan assays performed by HPLC utilized the following protocol. A Shimadzu HPLC equipped with a SCL-10A system controller, SIL-10A auto injector, LC-10AT liquid chromatograph, SPD-10A UV spectrophotometer detector, CTO-10A column oven, and Class-VP chromatography laboratory automated software was utilized. The column was a ZORBAX® RX-C18 4.6 mm by 150 mm column (Agilent Technologies) having a 5 μm particle size. Samples were injected (20 μL) onto the column for isocratic elution using mobile phase of phosphate buffered saline (pH 7.4):methanol:glacial acetic acid in a ratio of 500:250:10 (v/v). The mobile phase was selected in order to decrease or nominally quench melphalan conversion by having a high-chloride concentration. The samples were prepared immediately prior to injection. Detection was at 260 nm.

The literature procedure involved adding an excess amount of melphalan to 0, 10, 20, 30, 40, 50, 75 and 100 mM solutions of $SBE_7$-β-CD (avg. M.W.=2248 g/mol) in a 25 mM phosphate buffer solution at pH 7.5. The suspensions were placed in tightly capped vials, sonicated 1 h, and agitated at 25° C. for 23 h. The solutions were then centrifuged, the clear supernatant was diluted with doubly distilled water, and analyzed by HPLC. See D. Q. Ma et al., *J. Pharm. Sci.* 89:275 (1999).

The data from the free base melphalan solubilization studies are provided in FIG. 1. Referring to FIG. 1, free base melphalan displayed a significantly lower solubility enhancement than that provided in a previous literature report. See id. Because the solubility enhancement of free base melphalan provided by $SBE_{6.5}$-β-CD was lower than expected, additional phase solubility tests were performed using melphalan hydrochloride.

Example 3

The binding of melphalan hydrochloride (USP reference standard) and free base melphalan (Chemwerth) with a cyclodextrin derivative ($SBE_{6.5}$-β-CD, CAPTISOL®, avg. M.W.=2163 g/mol) was determined as a function of cyclodextrin derivative concentration at pH 7.5. The temperature was maintained at 22° C., and a 25 mM phosphate buffer was added to each solution. The data was compared with a literature report of free-base melphalan binding with $SBE_7$-β-CD (avg. M.W.=2248 g/mol) in a 25 mM phosphate buffer at pH 7.5 (see Example 2).

Figure 2:
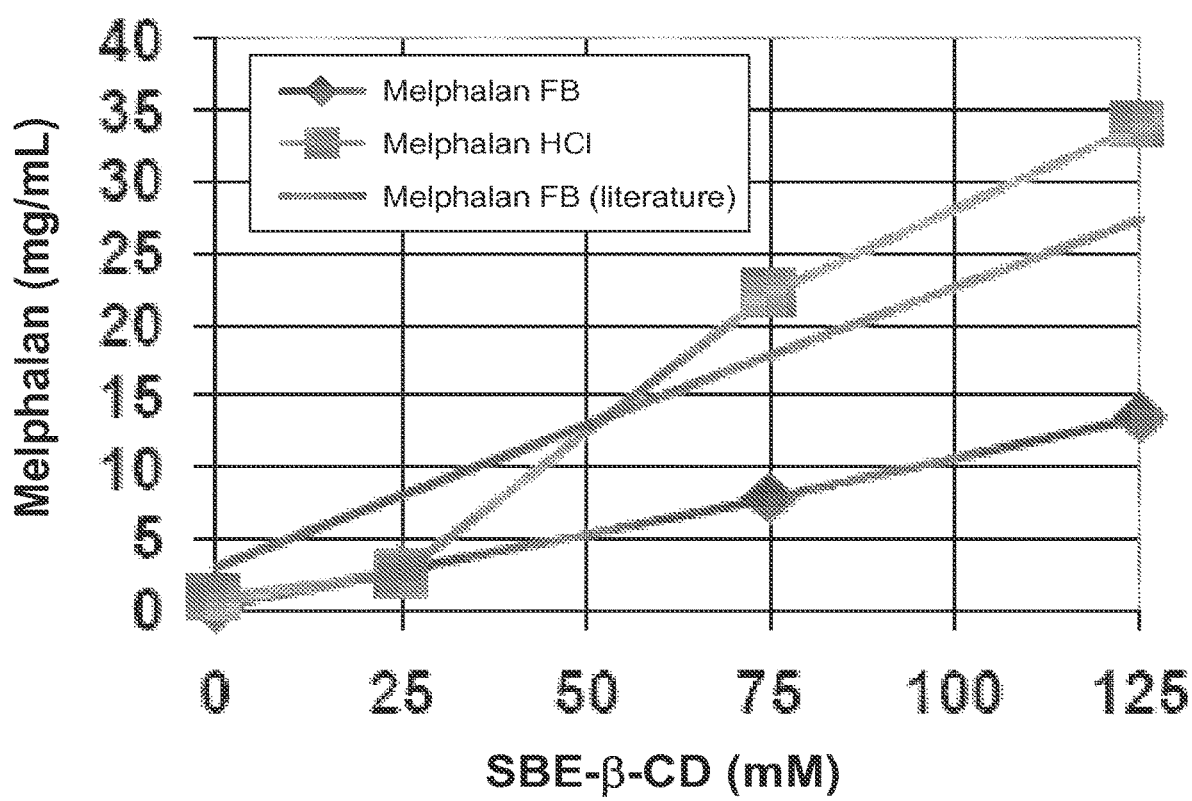
FIG. 2 provides a graphic representation of the solubility of free base melphalan and melphalan hydrochloride at pH 7.5 as a function of the concentration of a cyclodextrin derivative.

The samples were prepared by adding excess melphalan hydrochloride or free base melphalan to a 1 mL sample of various $SBE_{6.5}$-(β-CD solutions. The samples were vortex mixed for 30 seconds, sonicated at 20-24° C. for 60 minutes, and then mixed by end-over-end rotation at 22° C. for 60 minutes. The samples were then centrifuged, the clear supernatant was diluted with water, and analyzed by HPLC. The data are provided in FIG. 2. Referring to FIG. 2, the melphalan hydrochloride salt displayed a significant solubility enhancement compared to free base melphalan for all cyclodextrin derivative concentrations above 25 mM.

Example 4

Figure 3:
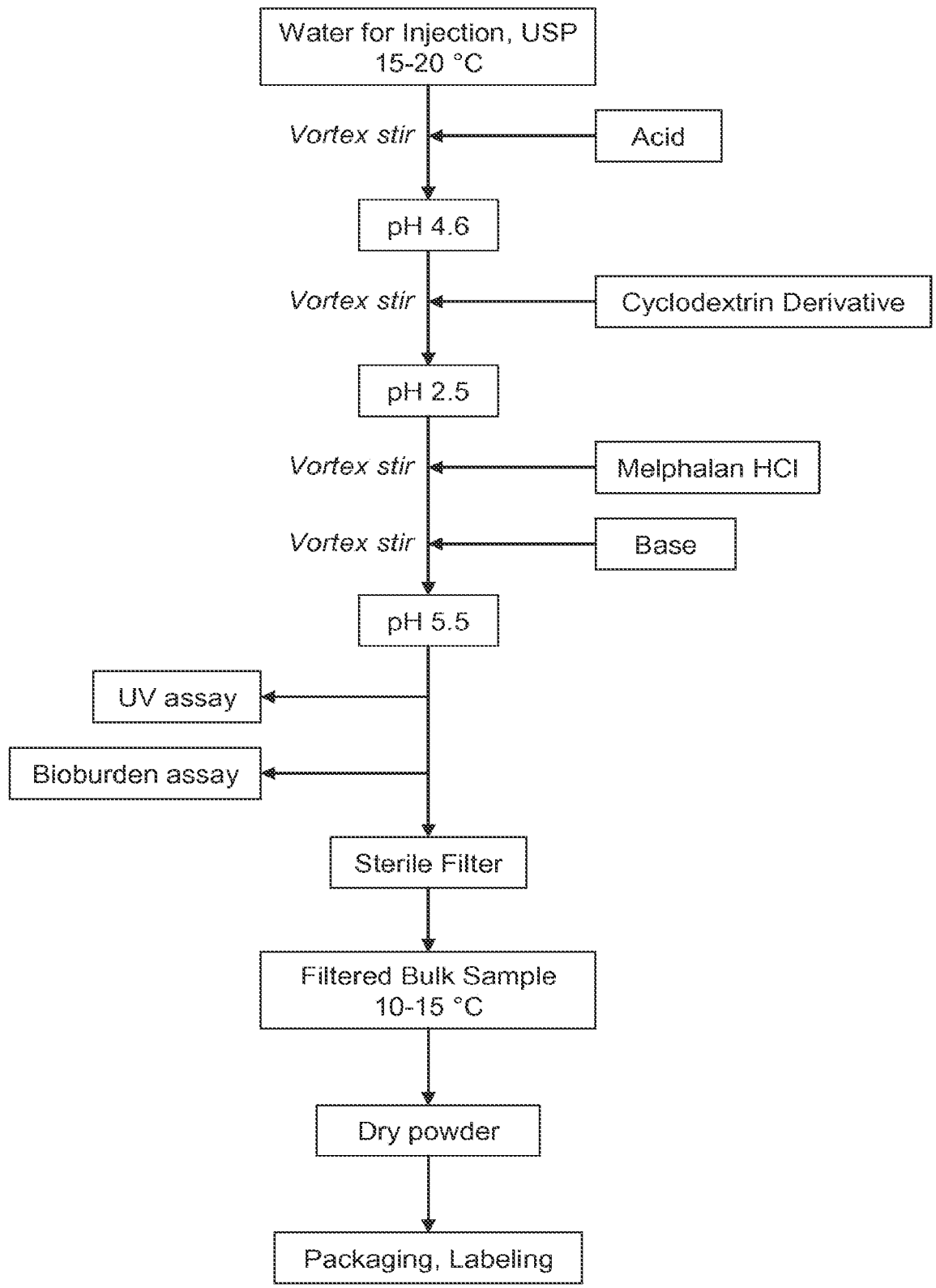
FIGS. 3 and 4 provide flow charts that describe processes for preparing a unit dosage form.

A pharmaceutical composition comprising melphalan as a hydrochloride salt was prepared by the process outlined schematically in FIG. 3. Referring to FIG. 3, water for injection, USP was placed in a stainless steel mixer at a temperature of 15-20° C., and hydrochloric acid was added until a pH of about 4.6 was achieved. The resulting solution was stirred at a speed sufficient to produce a vortex (but without foaming or frothing) for about 15 minutes, a cyclodextrin derivative (27.2 g $SBE_{6.5}$-β-CD, CAPTISOL®) was added slowly while vortex stirring, and the resulting solution was stirred for about 15 minutes to ensure complete dissolution. The resulting solution had a pH of about 2.5. Melphalan as a hydrochloride salt (516 mg) was added slowly while vortex stirring, and the resulting solution was stirred for about 15 minutes to ensure complete dissolution. A base (2 N NaOH) was then slowly added while vortex stirring until the solution had a pH of about 5.6. The solution was then assayed using a UV/vis spectrophotometer (detection wavelength of 260 nm). The solution comprised melphalan at a concentration of 5.16 mg/mL, and the melphalan was present in a ratio of about 1:55 w/w relative to the cyclodextrin derivative. The solution was then passed through a sterile filter (0.22 μm PVDF) and cooled to 10-15° C.

Example 5

The liquid pharmaceutical composition provided in Example 4 was lyophilized to provide a reconstitutable and/or dilutable dry powder comprising 50 mg of melphalan as a hydrochloride salt. Glass vials were filled with the solution (10 mL) and placed in trays on a pre-cooled shelf at 5° C. The vials were allowed to thermally equilibrate for about 30 minutes, and were then lyophilized to provide a dry powder in each vial. The vials were back-filled with nitrogen at a pressure of about 400 mTorr, and then sealed.

Example 6

A pharmaceutical composition comprising melphalan as a hydrochloride salt was prepared by the process described in Example 4, and outlined schematically in FIG. 3, except that the final solution contained melphalan at a concentration of 10 mg/mL, and the melphalan was present in a ratio of about 1:27 w/w relative to the cyclodextrin derivative.

Example 7

The liquid pharmaceutical composition provided in Example 6 was lyophilized to provide a reconstitutable and/or dilutable dry powder comprising 200 mg of melphalan as a hydrochloride salt. Glass vials were filled with the solution (20 mL) and placed in trays on a pre-cooled shelf at 5° C. The vials were allowed to thermally equilibrate for about 30 minutes, and were then lyophilized to provide a dry powder in each vial. The vials were back-filled with nitrogen at a pressure of about 400 mTorr, and then sealed, packaged, and labeled. The vials were protected from exposure to light during all aspects of the lyophilization, back-filling, sealing, packaging and labeling procedures.

Prophetic Example A

The liquid pharmaceutical composition provided in Examples 4 and 6 will be aseptically spray dried to provide a free-flowing powder to be filled aseptically. The free-flowing powder will meet or exceed the dissolution properties of the lyophilized powder prepared in Examples 4 or 6.

Example 8

Figure 4:
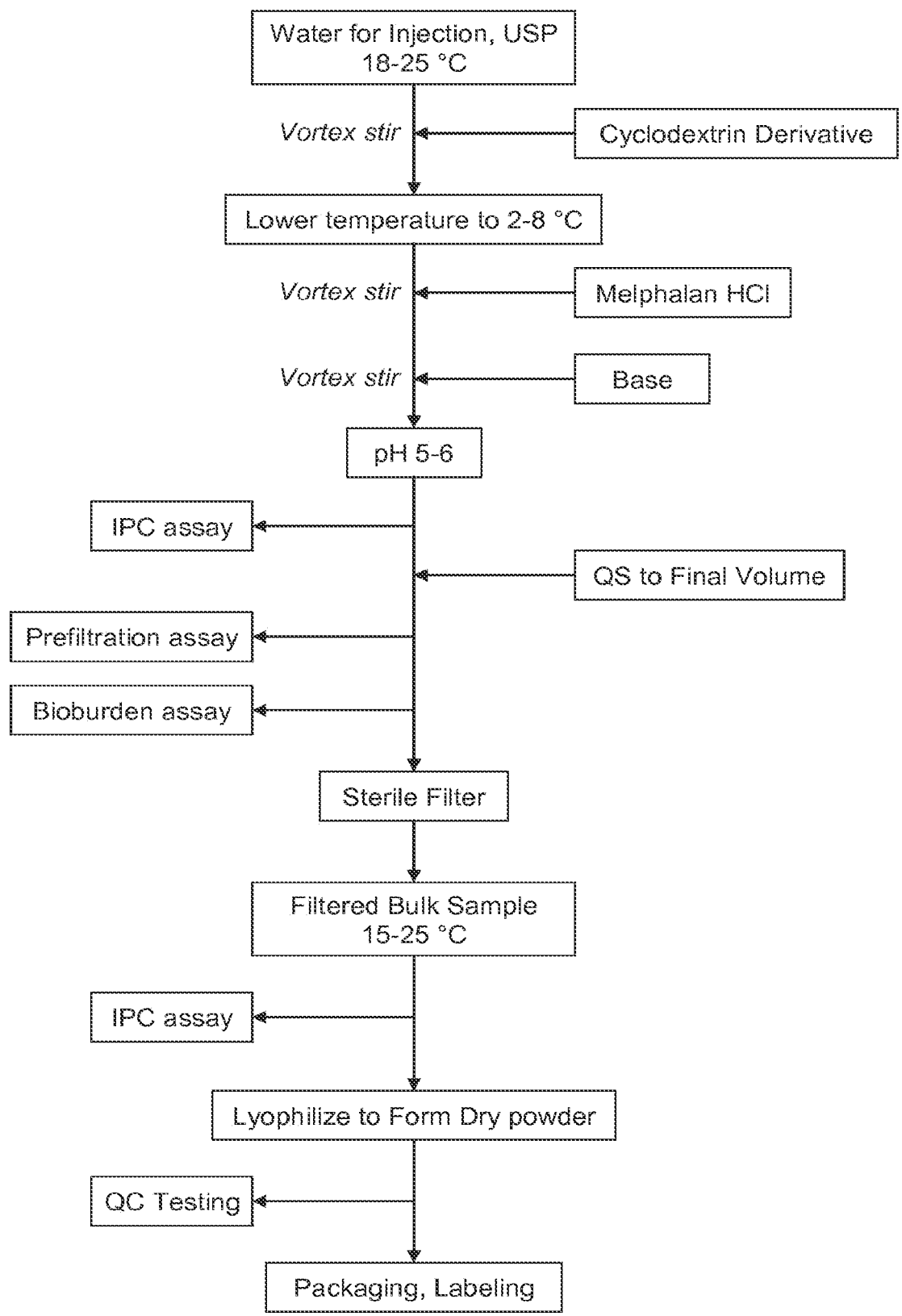

A pharmaceutical composition comprising melphalan as a hydrochloride salt was prepared by the process outlined schematically in FIG. 4. Referring to FIG. 4, water for injection, USP was placed in a stainless steel mixer at a temperature of 18-25° C., and the resulting solution was stirred at a speed sufficient to produce a vortex (but without foaming or frothing). A cyclodextrin derivative ($SBE_{6.5}$-β-CD, CAPTISOL®) was added slowly while vortex stirring, and the resulting solution was stirred for about 15 minutes to ensure complete dissolution. The resulting solution was then cooled to about 2-8° C. Melphalan as a hydrochloride salt was added slowly while vortex stirring, and the resulting solution was stirred for about 15 minutes to ensure complete dissolution. A base (2 N NaOH) was then slowly added while vortex stirring until the solution had a pH of about 5-6 (target pH 5.5). An in-process control ("IPC") assay was then performed to monitor pH, and the solution was diluted to the final target volume using water for injection, USP. The solution was then assayed using a UV/vis spectrophotometer (detection wavelength of 260 nm) and a bioburden assay was performed. The solution was then passed through a sterile filter (0.22 μm PVDF) and cooled to 15-25° C. Finally, an IPC assay was conducted.

Example 9

The solution prepared in Example 8 was lyophilized to provide a reconstitutable and/or dilutable dry powder comprising melphalan as a hydrochloride salt. For the lyophilization, glass vials were filled with the solution (10 mL) and placed in trays on a pre-cooled shelf at 5° C. The vials were allowed to thermally equilibrate for about 1 hour, and were lyophilized to provide a dry powder in each vial. The vials were back-filled with nitrogen, sealed, packaged, and labeled. The vials were protected from exposure to light during all aspects of the lyophilization, back-filling, sealing, packaging and labeling procedures.

Prophetic Example B

The liquid pharmaceutical composition provided in Example 8 will be aseptically spray dried to provide a free-flowing powder to be filled aseptically. The free-flowing powder will meet or exceed the dissolution properties of the lyophilized powder prepared in Example 9.

Example 10

The properties of the pharmaceutical compositions of the present disclosure after dilution with Water for Injection, USP, were analyzed by a variety of analytical methods. The results are listed in the Table below. Compositions A-D were prepared by the process described in Examples 8-9. The diluted compositions contained $SBE_{6.5}$-β-CD (CAPTISOL®) in a concentration of 75 mM, 100 mM, 125 mM, and 125 mM, respectively. Each of the compositions had a moisture content of about 1.3% to about 2.5% prior to dilution.

TABLE

Properties of pharmaceutical compositions of the present disclosure containing varying concentrations of a cyclodextrin derivative.

| | Dilution Volume | $SBE_{6.5}$-β-CD Conc. | Dissolution Time | pH | Density (22° C.) | Viscosity | Time for 5% loss |
|---|---|---|---|---|---|---|---|
| A | 10 mL | 75 mM | <30 s | 5.05 | 1.07 g/cc | 2.06 cP | 10 h |
| B | 10 mL | 100 mM | <30 s | 4.9 | 1.08 g/cc | 2.28 cP | 23 h |
| C | 10 mL | 125 mM | 45 s | 5.05 | 1.11 g/cc | 2.95 cP | 49 h |
| D | 5 mL | 125 mM | 105 s | 5.2 | 1.11 g/cc | 3.02 cP | 25 h |

Example 11

The stability of melphalan hydrochloride upon dilution of a pharmaceutical composition of the present disclosure was determined. Pharmaceutical compositions containing a cyclodextrin derivative ($SBE_{6.5}$-β-CD, CAPTISOL®, avg. M.W.-2163 g/mol) were diluted with isotonic saline to provide 0.45 mg/mL melphalan solutions that contained the cyclodextrin derivative at a concentration of 75 mM and 125 mM, respectively. Melphalan was assayed as a function of time, and the time necessary for a 5% or 10% loss of melphalan (based on an initial melphalan concentration of 100%) was determined. The data is provided in the Table below. The times required for melphalan to fall to 90% or 95% of its initial concentration in the solutions that contained the cyclodextrin derivative were compared to the stability of melphalan in a Reference product (ALKERAN® for Injection, GlaxoSmithKline).

TABLE

Melphalan stability as a function of cyclodextrin derivative concentration, compared to a reference melphalan standard.

| | Time for 5% loss | Time for 10% loss |
|---|---|---|
| $SBE_{6.5}$-β-CD (75 mM) | 5.4 h | 11 h |
| $SBE_{6.5}$-β-CD (125 mM) | 8.8 h | 18 h |
| Reference | 1.3 h | 2.7 h |

Referring to the data in the above Table, the stability of melphalan after dilution from a pharmaceutical composition of the present disclosure shows an improvement of approximately 4.2 times and 6.8 times at a cyclodextrin derivative concentration of 75 mM and 125 mM, respectively, compared to a reference melphalan formulation that does not contain a cyclodextrin derivative.

Example 12

The stability of melphalan hydrochloride upon dilution of a pharmaceutical composition of the present disclosure was determined as a function of temperature and storage conditions. Pharmaceutical compositions containing melphalan (50 mg) and a cyclodextrin derivative ($SBE_{6.5}$-β-CD, CAPTISOL®, avg. M.W.=2163 g/mol, 270 mg) were diluted with isotonic saline (8.5 mL) to provide a concentrated solution. The concentrated solution was further diluted 10-fold to provide a dilute solution. Each of the concentrated and diluted melphalan solutions were stored at 25° C./60% relative humidity, or in a refrigerator (~10° C.), and the melphalan content was monitored as a function of time. The data is provided in the Table below.

TABLE

Melphalan stability as a function of temperature and storage conditions.

| Solution | Time | Storage Conditions | Melphalan Assay | Monohydroxy Melphalan Assay |
|---|---|---|---|---|
| Conc. Sol'n | 0 | Refrigerator | 99% | 0.8% |
| " | 6.5 | " | 98.9% | 0.8% |
| " | 24.5 | " | 98.8% | 0.9% |
| " | 48.5 | " | 98.4% | 1% |

TABLE-continued

Melphalan stability as a function of temperature and storage conditions.

| Solution | Time | Storage Conditions | Melphalan Assay | Monohydroxy Melphalan Assay |
|---|---|---|---|---|
| Conc. Sol'n | 0 | 25° C./60% R.H. | 99% | 0.8% |
| " | 6 | " | 98% | 1.5% |
| " | 24 | " | 96% | 3.4% |
| " | 48 | " | 93% | 5.7% |
| Dilute Sol'n | 0 | Refrigerator | 99% | 1% |
| " | 5 | " | 98.4% | 1.4% |
| " | 24.3 | " | 97.8% | 2% |
| " | 48.4 | " | 96.7% | 2.7% |
| Dilute Sol'n | 0 | 25° C./60% R.H. | 99% | 1% |
| " | 5.3 | " | 94% | 5.3% |
| " | 23.8 | " | 81% | 15.5% |
| " | 47.2 | " | 70% | 20.2% |

Referring to the data in the above Table, the stability of melphalan after dilution from a pharmaceutical composition of the present disclosure provides a significant improvement compared to currently available melphalan pharmaceutical compositions that do not contain a cyclodextrin derivative.

Example 13

The stability of a lyophilized melphalan hydrochloride composition was determined before and after dilution as a function of temperature and storage conditions. The study was performed under the direction of CyDex Pharmaceuticals, Inc. by BioConvergence LLC, Bloomington, Ind.

Compositions comprising melphalan (50 mg) and povidone (20 mg) were diluted with compositions comprising a cyclodextrin derivative ($SBE_{6.5}$-β-CD, CAPTISOL®, avg. M.W.=2163 g/mol, 270 mg), sodium citrate (200 mg), and distilled water (10 mL) to provide concentrated melphalan solutions (5 mg/mL). In addition to testing the stability of the concentrated solutions, further dilution 11-fold to provide dilute solutions containing melphalan (0.45 mg/mL).

The kinetic stability of a reconstituted concentrated solution (5 mg/mL melphalan) was determined upon storage in a glass vial, and the kinetic stability of a reconstituted diluted solution (0.45 mg/mL melphalan) was determined upon storage in a 50 mL Baxter INTRAVIA® bag, at refrigerated (about 2°-8° C.) and room (about 25° C., monitored under fluorescent light) temperatures.

Evaluation of the kinetic stability of the dilute (0.45 mg/ml melphalan) composition was determined in a 50 mL Type I glass container: reconstitution was performed using saline (8.5 mL), and aliquots (4.5 mL) were removed from each vial and injected into 4 glass containers that held 45.5 mL of saline. After an amount was withdrawn from each container for t=0 analysis, the containers were stored at room temperature ("RT", about 25° C., under fluorescent light), or in a refrigerator (about 2°-8° C.), and the melphalan content was monitored as a function of time. The data is provided in the Table below.

TABLE

Summary of melphalan stability as a function of temperature and storage conditions

| Run | Form | Storage Conditions | Hold Time | MEL Degradation (% w/w) |
|---|---|---|---|---|
| 1 | Lyophilized comp. | RT (~20°-25° C.) | 2 yrs | <2% |
|  | Conc. solution (5 mg/mL) | Immediately diluted | n/a | n/a |
|  | Dilute solution (0.45 mg/mL) | RT (~20°-25° C.) | 10 h | <4% |
| 2 | Lyophilized comp. | RT (~20°-25° C.) | 2 yrs | <2% |
|  | Conc. solution (5 mg/mL | RT (~20°-25° C.) | 24 h | <4% |
|  | Dilute solution (0.45 mg/mL) | RT (~20°-25° C.) | 5 h | <2% |
| 3 | Lyophilized comp. | RT (~20°-25° C.) | 2 yrs | <2% |
|  | Conc. solution (5 mg/mL) | Refrigerated (2°-8° C.) | 48 h | <4% |
|  | Dilute solution (0.45 mg/mL) | RT (~20°-25° C.) | 5 h | <2% |
| 4 | Lyophilized comp. | RT (~20°-25° C. | 2 yrs | <2% |
|  | Conc. solution (5 mg/mL) | Immediately diluted | n/a | n/a |
|  | Dilute solution (0.45 mg/mL) | 1) Refrigerated (2°-8° C.) 2) RT (~20°-25° C.) | 1) 24 h 2) 5 h | 1) <2% 2) <2% |

Referring to the data in the above Table, the stability of melphalan after dilution from a pharmaceutical composition of the present disclosure provides a stable composition that can be maintained at room temperature for up to 5 hours and exhibit less than 2% melphalan degradation, or up to 10 hours and exhibit less than 4% melphalan degradation. When refrigerated, a diluted melphalan composition can be stored up to 24 hours and exhibit less than 2% melphalan degradation. Additionally, a lyophilized pharmaceutical composition can be stored up to 2 years at room temperature and exhibit less than 2% melphalan degradation.

Furthermore, referring to Examples 12 and 13, the pharmaceutical compositions of the present disclosure provide a significant improvement in melphalan stability compared to other formulations in which the use of a cyclodextrin derivative has been proposed. For example, D. Q. Ma et al., *Int. J. Pharm.* 189:227 (1999) provide a melphalan composition that upon dilution with a solution containing a cyclodextrin derivative, exhibits a melphalan loss of more than 60% after 48 hours at room temperature. Significantly, the data in the above Tables illustrates that upon dilution of a pharmaceutical composition of the present disclosure, a melphalan loss of at most 30% is observed within 48 hours at room temperature. The melphalan loss can be reduced to as low as 2% or 3% when the solution is stored at a reduced temperature (e.g., in a refrigerator).

Example 14

The hemolytic potential of a cyclodextrin derivative suitable for use with the pharmaceutical composition of the present disclosure was analyzed in comparison to a previously marketed diluent vehicle for melphalan (ALKERAN® For Injection, GlaxoSmithKline). The hemolytic potential was evaluated in rodent (SPRAGUE DAWLEY® or Wistar Han IGS rats) and human red blood cells obtained from fasted subjects using a spectrophotometric technique. Normal saline (0.9% sodium chloride) was used as the blank (or background) and as a negative control for comparison against various concentrations of a cyclodextrin derivative-containing, and cyclodextrin-free diluent vehicles. A positive control containing Triton X-100 (1%) in phosphate buffered saline was also utilized. Human red blood cells were taken from fasted (≥8 h) adult subjects. The components of the various samples are listed in the following Table.

TABLE

Components of diluent vehicles used for hemolysis studies.

| Identification | Constituents |
|---|---|
| Negative Control/Blank | 0.9% Sodium Chloride |
| Positive Control | 1% TRITON ® X-100 in phosphate buffered saline |
| Cyclodextrin Derivative Diluent | SBE$_{6.5}$-β-CD (CAPTISOL ®, 9.72 g) q.s. 400 mL with normal saline |
| ALKERAN ® for Injection (GlaxoSmithKline) Diluent | Povidone (K-12, 72 mg) Sodium citrate (720 mg) Propylene glycol (21.6 mL, 22.4 g) Ethanol (1.87 mL, 1.48 g) Water (12.2 mL) q.s. 400 mL with normal saline |

The rat and human red blood cells were exposed to various concentrations of the diluent vehicles and the hemolytic potential was evaluated using equation (1):

$$sA_{540}(\text{test article}) - A_{540}(\text{negative control}) \times 100 = \% \text{ Hemolysis} \quad (1)$$

The hemolysis results are provided in the following Table, where Group A refers to rat red blood cells exposed to the cyclodextrin derivative vehicle; Group B refers to rat red blood cells exposed to the ALKERAN® for Injection (GlaxoSmithKline) diluent vehicle; Group C refers to human red blood cells exposed to the cyclodextrin derivative vehicle; and Group D refers to human red blood cells exposed to the ALKERAN® for Injection (GlaxoSmithKline) diluent vehicle. The negative controls for each experiment provided absorbances below 0.13, and the positive controls for each experiment provided absorbances of about 2.8 to 3.

TABLE

Hemolysis results for rat and human red blood cells exposed to various diluent vehicles.

| Group | Meas. | none | 1:2 | 1:4 | 1:8 | 1:16 | 1:32 | 1:64 | 1:128 |
|---|---|---|---|---|---|---|---|---|---|
| A | Abs. (a.u.) | 0.11 | 0.114 | 0.11 | 0.117 | 0.116 | 0.118 | 0.119 | 0.118 |
|   | Hem. (%) | 1% | 0 | 0 | 0 | 0 | 0 | 0 | 0 |
| B | Abs. (a.u.) | 0.178 | 0.155 | 0.141 | 0.128 | 0.125 | 0.121 | 0.123 | 0.124 |
|   | Hem. (%) | 2% | 1% | 1% | 0 | 0 | 0 | 0 | 0 |
| C | Abs. (a.u.) | 0.021 | 0.021 | 0.022 | 0.019 | 0.017 | 0.016 | 0.017 | 0.025 |
|   | Hem. (%) | 0 | 0 | 0 | 0 | 0 | 0 | 0 | 0 |
| D | Abs. (a.u.) | 0.037 | 0.031 | 0.033 | 0.02 | 0.025 | 0.022 | 0.027 | 0.027 |
|   | Hem. (%) | 0 | 0 | 0 | 0 | 0 | 0 | 0 | 0 |

Referring to the hemolysis data in the above Table, the solution that contained the cyclodextrin derivative at high concentrations (e.g., no dilution, 1:2 dilution with saline, and 1:4 dilution with saline) provided reduced hemolysis in rat red blood cells, which was also exhibited as a reduction in spectrophotometric absorption of about 30% compared to the ALKERAN® for Injection (GlaxoSmithKline) diluent. While the hemolysis tests in human blood cells exhibited a similar reduction in spectrophotometric absorbance at high concentrations, neither the cyclodextrin derivative solution or the ALKERAN® for Injection (GlaxoSmithKline) diluent vehicle induced hemolysis in human red blood cells.

Example 15

A study was conducted that determined melphalan associated with SAE$_{6.5}$-β-CD (CAPTISOL®, CyDex Pharmaceuticals, Inc., Lenexa, Kans.) exhibits the same protein binding as unassociated melphalan. The study was performed under the direction of CyDex Pharmaceuticals, Inc. by Analytical Biochemistry Laboratories, Inc., Columbia, Mo.

Preliminary Study

A preliminary study was performed that determined radioactive-labeled melphalan, [$^{14}$C]-melphalan (Moravek Biochemicals, Inc., Brea, Calif.), does not bind non-specifically to ultrafiltration devices. The following mixtures of compounds were added to human plasma ultrafiltrate (Biochemed, Winchester, Va.) to determine the protein binding of [$^{14}$C]-melphalan alone or in combination with $SAE_{6.5}$-β-CD:

1. [$^{14}$C]-melphalan with melphalan; and
2. [$^{14}$C]-melphalan with melphalan and $SAE_{6.5}$-β-CD.

Radioactive-labeled warfarin, [$^{3}$H]-warfarin (Moravek Biochemicals, Inc., Brea, Calif.), a compound with well-documented protein binding properties was used as a positive control in all experiments.

Powdered material (as applicable) was weighed into scintillation vials (20 mL) and the radiolabeled compounds were added to the vials using a positive displacement pipette. Blank human plasma ultrafiltrate (5 mL) was then added to the vials using a glass serological pipette. The mixtures were then blended briefly. The time-dependence of plasma protein binding was determined by sampling the mixtures 0.5, 1, and 5 minutes after addition of the test compounds to the human plasma ultrafiltrate. The sample aliquots (3×1 mL) were dispensed into the ultrafiltration devices, and the samples were immediately centrifuged (1600 g for 5 minutes at 25° C.). The solution remaining in the vials was then aliquoted for Liquid Scintillation Counting (LSC) analysis (2×0.1 mL).

More than 95% recovery was observed for [$^{3}$H]-warfarin in all experiments. In the protein-binding experiments, [$^{3}$H]-warfarin was over 99% protein bound. Radiolabeled melphalan (alone or in combination with $SAE_{6.5}$-β-CD) applied to ultrafiltration devices having a molecular weight cutoff of 30 kD exhibited an average of over 97% radioactivity recovery: [$^{14}$C]-melphalan alone exhibited a recovery of 97.7% (n=3), and [$^{14}$C]-melphalan with $SAE_{6.5}$-β-CD exhibited a recovery of 97.6% (n=3). The results demonstrate that there was minimal (i.e., less than 2.4%) non-specific binding of radiolabeled melphalan to the ultrafiltration devices.

Protein-Binding Study

For the protein-binding study, the radiolabeled melphalan, non-radiolabeled melphalan, and $SAE_{6.5}$-β-CD (as applicable) were added to a scintillation vial (20 mL) and blown to dryness under a nitrogen stream to standardize the amount of solvent present in each experiment. Methanol (50 μL) was added to the vials and blank human plasma (5 mL) was added to the vials using a glass serological pipette. The mixtures were then blended briefly. Aliquots (3×1 mL) were then dispensed from the vials into the ultrafiltration devices, followed by centrifugation (2,000 g for 5 minutes at 25° C.). The time interval between adding human plasma to the vials and the start of centrifugation was 0.5, 1, 5, 10, and 30 minutes. The solution remaining in the vials was then aliquoted in duplicate (at a volume of 0.1, 0.05, and 0.025 mL) for LSC analysis.

Sample radioactivity was quantified using a scintillation counter (Beckman Instruments, Inc. Schaumberg, Ill.) equipped with the H-number method for cpm to dpm conversion. LSC analysis was performed with samples (5 mL) in glass scintiallation vials (7 mL), from which background measurements were made using the same amount of scintillation fluid added to the vials. The results are provided in the following Table:

TABLE

Protein binding of radiolabeled melphalan ("[$^{14}$C]-mel") with unlabeled melphalan ("mel") in the presence and absence of $SAE_{6.5}$-β-CD.

| Mixture | Conc. (dpm/mL) | Conc. (μg/mL) | Rep. | Total Recovery (%) Data | Avg. | % Binding Data | Avg. |
|---|---|---|---|---|---|---|---|
| [$^{14}$C]-mel + mel (1 min.) | 112, 105 | 14 | 1 | 96.4 | 97.1 | 64.5 | 64.3 ± 0.34 |
|  |  |  | 2 | 96.9 |  | 63.9 |  |
|  |  |  | 3 | 98.0 |  | 64.4 |  |
| [$^{14}$C]-mel + mel + $SAE_{6.5}$-β-CD (0.5 min) | 112, 382 | 14 | 1 | 92.9 | 91.5 | 63.7 | 64.3 ± 0.69 |
|  |  |  | 2 | 95.4 |  | 64.1 |  |
|  |  |  | 3 | 86.4 |  | 65.1 |  |
| [$^{14}$C]-mel + mel + $SAE_{6.5}$-β-CD (1 min.) | 108, 085 | 13 | 1 | 97.3 | 97.5 | 63.8 | 64.4 ± 0.59 |
|  |  |  | 2 | 97.0 |  | 64.8 |  |
|  |  |  | 3 | 98.3 |  | 64.6 |  |
| [$^{14}$C]-mel + mel + $SAE_{6.5}$-β-CD (5 min.) | 109, 621 | 13 | 1 | 96.5 | 95.9 | 65.8 | 67.2 ± 1.96 |
|  |  |  | 2 | 95.7 |  | 69.5 |  |
|  |  |  | 3 | 96.5 |  | 66.4 |  |
| [$^{3}$H]-warfarin | 114, 932 | 0.052 | 1 | 98.5 | 101 | 98.9 | 98.8 ± 0.01 |
|  |  |  | 2 | 100 |  | 98.8 |  |
|  |  |  | 3 | 103 |  | 98.8 |  |

The results showed that [$^{14}$C]-melphalan in the absence of $SAE_{6.5}$-β-CD was 64.3% protein bound after 1 minute in human plasma. Similar degrees of protein binding were observed for [$^{14}$C]-melphalan in the presence of $SAE_{6.5}$-β-CD: 64.3% (0.5 minutes, n=3), 64.4% (1 minute, n=3), and 67.2% (5 minutes, n=3). The study showed that $SAE_{6.5}$-β-CD did not affect the protein-binding of radiolabeled [$^{14}$C]-melphalan.

Example 16

A study was performed to investigate the potential for a sulfoalkyl ether cyclodextrin to perturb the in vivo pharmacokinetics of melphalan. Pharmacokinetic parameters were determined for melphalan following intravenous administration to male Sprague Dawley rats in the presence or absence of $SBE_{6.5}$-β-CD in the delivery vehicle.

The pharmacokinetics of melphalan were studied in overnight-fasted male Sprague Dawley rats. All experimental procedures were approved and performed in accordance with the guidelines of the Institutional Animal Experimentation Ethics Committee (Monash University Ethics approval number VCPA/2008/02).

On the day prior to dosing, a commercially available BASi CULEX® cannula (for use with a CULEX® automated blood sampling device) was inserted into the left carotid artery of each rat under isoflurane anesthesia (2%). A polyethylene cannula was also inserted into the right jugular vein. Cannulae were exteriorized by tunneling subcutaneously to emerge above the scapulae.

Immediately following surgery and through to the end of the experiment, rats were housed in RATURN® metabolic cages in the CULEX® automated blood sampler. All rats returned to normal grooming, drinking and sleeping behavior within an hour of surgery. Animals were given a small amount of food just after they awoke from the anesthetic, but were then fasted for 16-18 hours prior to drug administration. Animals had access to water ad libitum at all times. Food was reinstated 4 hours following drug administration. At the conclusion of each experiment, rats were killed by a single lethal injection of pentobarbitone.

The cyclodextrin derivative-free melphalan formulation was prepared as per the product insert for ALKERAN® for Injection (GlaxoSmithKline). The contents of a single ALKERAN® for Injection (GlaxoSmithKline) vial were reconstituted with 10 mL of sterile diluent (provided with the ALKERAN® product, and containing 0.2 g sodium citrate, 6 mL propylene glycol, 0.52 mL ethanol (96%) and water). The solution was then further diluted with 0.9% normal saline (2 mL ALKERAN® for Injection (GlaxoSmithKline) in 10 mL of 0.9% saline, i.e., 12 mL total volume), and the resultant formulation was sterilized by filtering through a 0.22 μm syringe filter before administering to rats. The measured concentration of melphalan in the IV formulation was 0.54 mg/mL (as free base) and the pH of the final solution was between 5 and 6 (checked using pH paper). The formulation was administered to animals within 30 minutes of preparation.

A formulation containing $SBE_{6.5}$-β-CD (27% w/v) was prepared by dissolving $SBE_{6.5}$-β-CD in Milli-Q water. Contents of an ALKERAN® for Injection (GlaxoSmithKline) vial were then reconstituted with 10 mL of the $SBE_{6.5}$-β-CD solution. This solution was then diluted with 0.9% saline (2 mL in 10 mL of 0.9% saline) and the resultant formulation was sterilized by filtering through a 0.22 μm syringe filter before administering to rats. Thus, the final formulation contained 4.5% (w/v) $SBE_{6.5}$-β-CD. The measured concentration of melphalan (as free base) was 0.58 mg/mL and the pH of the final solution was between 5 and 6 (checked using pH paper). The formulation was administered to animals within 30 minutes of preparation.

The total dose volume was 1 mL and all doses were infused manually via the jugular vein cannula. The complete dose was delivered over a 10-minute period and the cannula was flushed with heparinized saline (10 U/mL) to ensure complete administration of the dose.

Samples of arterial blood and urine were collected according to the following schedules: blood/plasma sampling times were pre-dose, and 5, 10 (end of infusion), 15, 25, 40, 55, 70, 100, 130, 190, 250, 370, and 490 minutes post-dose; and urine sampling intervals were 0-70 minutes, 70-130 minutes, 130-190 minutes, 190-250 minutes, 250-310 minutes, 310-370 minutes, 370-430 minutes, 430-490 minutes, and 490-1450 minutes.

Arterial blood was collected directly into borosilicate vials (at 4° C.) containing heparin, COMPLETE® (a protease inhibitor cocktail), potassium fluoride, and EDTA to minimize potential for ex vivo degradation in blood/plasma samples. Once collected, an aliquot (50 μL) of whole blood was transferred into a fresh micro-centrifuge tube. The remaining blood was centrifuged and supernatant plasma removed. All blood, plasma and urine samples were immediately (snap) frozen on dry ice and then transferred to −20° C. freezer for storage until analysis.

The melphalan concentration in whole blood, plasma, urine and samples of dosing solutions were determined using LC-MS.

Sample preparation was performed using protein precipitation with acetonitrile. Aliquots of the plasma and blood (50 μL) were treated with internal standard (10 μL), acetonitrile (130 μL), vortexed and centrifuged. The supernatant was removed and analyzed by LC/MS. Standard samples were prepared by spiking solution standards in the respective blank matrix. A stock solution of melphalan free base was prepared at a concentration of 10 mg/mL in dimethylsulfoxide. This stock solution was further diluted in aqueous acetonitrile (50% v/v) to obtain spiking solutions for the preparation of calibration standards.

All samples were assayed via LC-MS/MS on a Micromass Quattro Premier PR triple quadrupole instrument coupled with a Waters Acquity UPLC (Waters Corp., Milford, Mass.). Analytical separations were performed on a Phenomenex Polar reverse-phase column (50 mm×1.0 mm inner diameter, 4 μm particle size) equipped with a Phenomenex Polar Security Guard column of the same material (Torrance, Calif.). Samples (7.5 μL) were injected onto the column and compounds were eluted (at a flow rate of 0.15 mL/min) using a ternary gradient solvent system consisting of an aqueous solution of methanol (2% v/v) and formic acid (0.05% v/v) in Milli-Q water (solvent A), and acetonitrile containing formic acid (0.05% v/v) (solvent B). The gradient conditions used for LC-MS analysis are listed in the following table.

TABLE

Gradient chromatography conditions used for the analysis of melphalan.

| Time (minutes) | Solvent A | Solvent B |
| --- | --- | --- |
| 0-0.2 | 89 | 2 |
| 0.3 | 80 | 20 |
| 2.7 | 20 | 80 |
| 2.8 | 5 | 95 |
| 3.3 | 5 | 95 |
| 3.5-4.5 | 98 | 2 |

Elution of analytes was confirmed by multiple reaction monitoring (MRM) using diazepam (0.2 μg/mL) as the internal standard (diazepam). Inlet cone voltages were 20 eV and 40 eV for melphalan and the internal standard, respectively, and collision energies of 15 eV and 27 eV for melphalan and the internal standard, respectively. The elution of melphalan and internal standard was monitored using the following transitions 304.94>267.88 and 285.17>154.02, respectively. Melphalan exhibited a retention time of 2.0 minutes and the internal standard exhibited a retention time of 2.8 minutes.

Mass spectrometry was performed using positive mode electrospray ionization with a capillary voltage of 3.2 kV, detector multiplier gain of 650 V, and source block and desolvation temperatures of 90° C. and 300° C., respectively. A desolvation gas (nitrogen) and collision gas (argon) flow of 500 L/h and 0.38 mL/min, respectively, was maintained. The lower limit of quantitation (LLQ) for blood and plasma standards was 5.0 ng/mL, and the LLQ for diluted urine samples was 0.5 ng/m L.

Both plasma and blood concentration data were analysed to obtain pharmacokinetic parameters using WINNONLIN® software (WINNONLIN® professional version 5.2.1, Pharsight Corp., Mountain View, Calif.). The total clearance ($CL_{total}$, for whole blood or plasma) after intravenous administration was calculated as: $CL_{total}$=Dose/AUC, where AUC is the area under the whole blood or plasma concentration versus time curve obtained using the linear trapezoidal method. The volume of distribution ($V_z$) was calculated as: $V_z = CL_{total}/\lambda_z$, where $\lambda_z$, is the elimination rate constant after i.v. administration.

The mean dose-normalized concentration versus time profiles of melphalan in whole blood and plasma following intravenous administration using a formulation containing $SBE_{6.5}$-β-CD (n=4) and a cyclodextrin-free (n=5) formulation are presented in the following table.

TABLE

Pharmacokinetic parameters for melphalan in whole blood and plasma following intravenous administration to male Sprague Dawley rats at a nominal dose of 2.0 mg/kg with a formulation containing a cyclodextrin derivative ($SBE_{6.5}$-β-CD) and a formulation free from a cyclodextrin derivative ("CD-free formulation").

| Melphalan | Whole Blood | | Plasma | |
| --- | --- | --- | --- | --- |
| | $SBE_{6.5}$-β-CD (27% w/v) | CD-free formulation | $SBE_{6.5}$-β-CD (27% w/v) | CD-free formulation |
| Apparent $t_{1/2}$ (h) | 0.8 ± 0.1 | 0.9 ± 0.1 | 0.8 ± 0.1 | 0.9 ± 0.1 |
| $CL_{total}$ (mL/min/kg) | 10.9 ± 2.0 | 12.2 ± 1.3 | 8.1 ± 1.1 | 9.3 ± 1.4 |
| $V_z$ (L/kg) | 0.8 ± 0.2 | 1.0 ± 0.2 | 0.6 ± 0.1 | 0.7 ± 0.2 |
| $AUC_{0-inf}/D$ (μM · min · kg/μmol) | 94.2 ± 16.6 | 82.8 ± 8.8 | 125.4 ± 15.0 | 109.6 ± 16.1 |

Figure 5A:
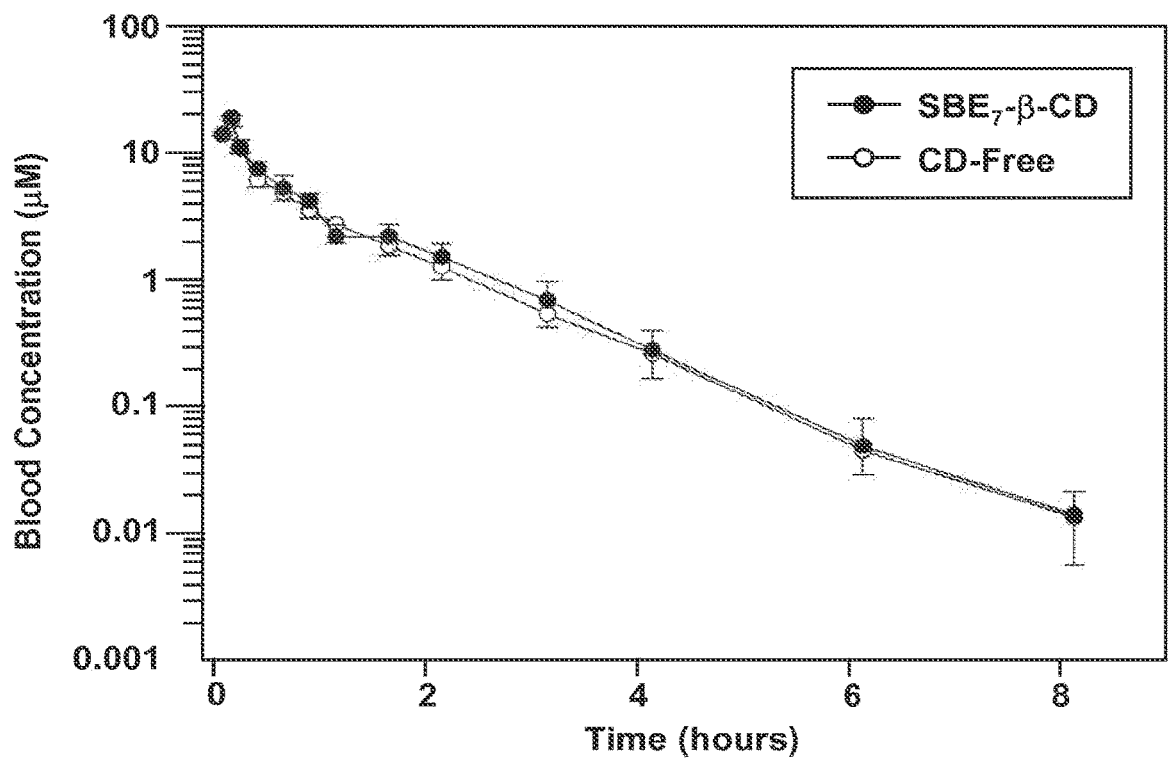
FIGS. 5A-5B provide a graphic representation of dose-normalized whole blood (FIG. 5A) and plasma (FIG. 5B) concentrations of melphalan following intravenous administration to male Sprague-Dawley rats using a melphalan formulation containing a cyclodextrin derivative ($SBE_{6.5}$-β-CD) and a cyclodextrin-free melphalan formulation (ALKERAN® for Injection, GlaxoSmithKline).
Figure 5B:
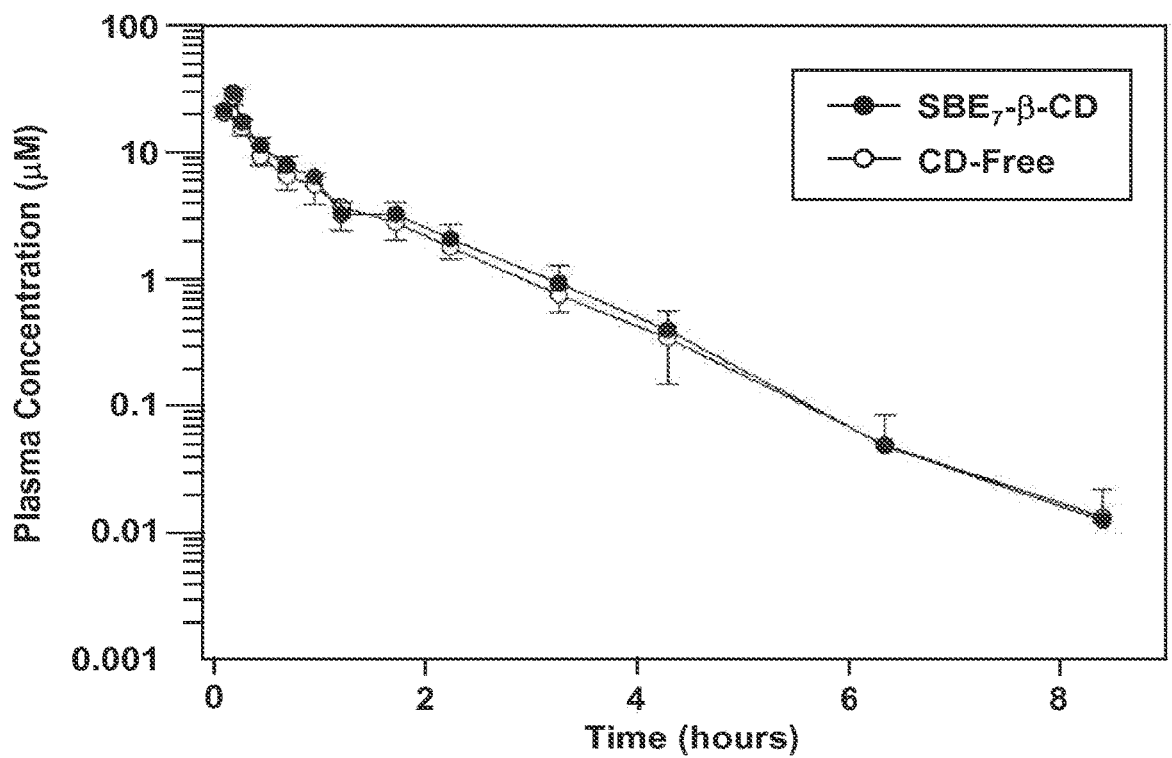

FIGS. 5A-5B provide graphic representations of the dose-normalized whole blood (FIG. 5A) and plasma (FIG. 5B) concentrations of melphalan following intravenous administration for the $SBE_{6.5}$-β-CD-containing melphalan formulation (●), n=4, and the cyclodextrin-free (○), n=5, melphalan formulation (ALKERAN® for Injection, GlaxoSmithKline). Referring to FIGS. 5A-5B, the data is presented as mean with error bars indicating a single standard deviation. Melphalan exhibited bi-exponential pharmacokinetics in both whole blood and plasma and the apparent terminal elimination phase was well-defined within the 8 hour post-dose blood sampling period, with the apparent terminal elimination half-life. The mean whole blood and plasma concentration versus time profiles for the formulation that contained $SBE_{6.5}$-β-CD (27% w/v) and cyclodextrin-free formulation were essentially super-imposable and there were no statistically significant differences in any of the pharmacokinetic parameters between the two formulations (p>0.05). Thus, as shown in the above table, in the rat the in vivo pharmacokinetic parameters for a melphalan formulation containing $SBE_{6.5}$-β-CD are essentially identical to the pharmacokinetic parameters for a cyclodextrin-free formulation (i.e., ALKERAN® for Injection, GlaxoSmithKline).

Additionally, in both formulations the percentage of the melphalan dose excreted in urine excreted as unchanged compound up to 24 hours post-dose was low: for the cyclodextrin-free formulation the average was 2.7±1.7%, and for the formulation containing $SBE_{6.5}$-β-CD the average was 2.3±2%.

The data show that pharmacokinetic parameters, including half-life, AUC, volume of distribution, clearance, and the extent of renal elimination of melphalan were essentially unchanged between ALKERAN® for Injection (GlaxoSmithKline) and the melphalan formulation that contained $SAE_{6.5}$-β-CD. Specifically, the mean whole blood and plasma concentration versus time profile of melphalan with and without $SBE_{6.5}$-β-CD are essentially super-imposable. The results demonstrate that $SBE_{6.5}$-β-CD had no observable difference in blood or plasma versus time profiles for melphalan in the rat model. Furthermore, there was no apparent difference in the urinary excretion of melphalan in the rat model.

Example 17

A Phase IIa, multicenter, open-label, randomized, efficacy and safety study of melphalan hydrochloride administered by injection using a propylene glycol-free diluent vehicle has been conducted in 3 human multiple myeloma patients who underwent myeloablative conditioning in preparation for autologous transplantation. The study is on-going.

The primary goal of the study was/is to determine the rate of myeloablation and neutrophil engraftment in multiple myeloma patients who receive a high-dose of melphalan hydrochloride via injection in which one dose is administered using a propylene glycol diluent and one dose is administered using a propylene glycol-free diluent. The administering is used as myeloablative therapy prior to autologous stem cell transplantation.

The secondary goal of the study is to determine: (a) the rate of platelet engraftment in multiple myeloma patients receiving high-dose melphalan hydrochloride via injection using both a propylene glycol diluent and a propylene glycol-free diluent prior to autologous stem cell transplantation; (b) the median time to engraftment of neutrophil and platelets in multiple myeloma patients receiving high-dose melphalan hydrochloride via injection using both a propylene glycol diluent and a propylene glycol free diluent prior to autologous stem cell transplantation; (c) the response rate (stringent complete response [sCR], complete response [CR], very good partial response [VGPR], partial response [PR], stable disease [SD], or progressive disease [PD]) at autologous stem cell transplantation at day +100 in multiple myeloma patients receiving high-dose melphalan hydrochloride via injection using a propylene glycol diluent and a propylene glycol-free diluent prior to autologous stem cell transplantation; (d) the toxicity profile of high-dose melphalan hydrochloride via injection using both a propylene glycol diluent and a propylene glycol-free diluent in multiple myeloma patients undergoing autologous stem cell transplantation; (e) the rate of treatment-related mortality during the first 100 days after autologous stem cell transplantation in multiple myeloma patients receiving high-dose melphalan hydrochloride via injection using a propylene glycol diluent and a propylene glycol-free diluent; and (f) the pharmacokinetics of melphalan hydrochloride via injection using a propylene glycol diluent compared with the pharmacokinetics of melphalan hydrochloride via injection using a propylene glycol-free diluent (i.e., a cyclodextrin derivative) in multiple myeloma patients undergoing autologous stem cell transplantation.

Patients were screened prior to enrollment in the study. Patients from any of the following classes were qualified for inclusion in the study:

Patients with symptomatic multiple myeloma requiring treatment at diagnosis or anytime thereafter;

Patients with multiple myeloma who qualify for autologous stem cell transplantation therapy who have received appropriate primary induction therapy for transplantation;

Patients who are 70 years of age or younger at time of transplantation (patients greater than 70 years of age may qualify on a case-by-case basis if the patient meets criterion based on institution's standard of practice);

Patients with an adequate autologous graft, defined as an un-manipulated, cryopreserved, peripheral blood stem cell or bone marrow stem cell graft containing at least $2 \times 10^6$ CD34+ cells/kg based upon patient weight, along with a reserve of $2 \times 10^6$ CD34+ cells/kg that is stored in a separate bag; and Patients with adequate organ function as measured by:
Cardiac: Left ventricular ejection fraction at rest >40%;
Hepatic: Bilirubin <2× the upper limit of normal and ALT/AST<3×ULN;
Renal: Creatinine clearance >40 mL/minute; and
Pulmonary: DLCO, $FEV_1$, FVC>50% of predicted value (corrected for Hgb) or $O_2$ saturation >92% on room air.

All patients have received antiemetics, hydration, and infection prophylaxis according to institutional guidelines. Patients followed institutional guidelines regarding hospitalization. Patients returned for daily laboratory tests (CBC with differential and platelets and a basic chemistry panel) until neutrophil engraftment, and then returned for weekly safety evaluations until autologous stem cell transplantation Day +30. The following safety, efficacy, and pharmacokinetic evaluations were performed prior to the first dose of melphalan, and at the following post-dose time points:

Twelve blood samples were taken at specific time points for a pharmacokinetic evaluation. Blood samples were collected immediately prior to and after receiving the melphalan dose;

Vital signs were recorded hourly during the first eight hours after receiving each dose of melphalan, then repeated once daily until hospital discharge, and then weekly until Day +30. Weight were collected at hospital discharge and at Day +30;

A 12-lead electrocardiograph, (ECG) along with a 10 to 20 second rhythm strip was collected twice weekly until hospital discharge, then a 12-lead ECG (without a rhythm strip) was collected weekly until Day +30;

A focused physical examination was performed daily until hospital discharge, then a complete physical examination was performed weekly until Day +30;

Toxicity grading and evaluation for AEs/SAEs was according to NCI-CTC AE Version 3.0 during the entire Study Period;

Complete blood count with differential and platelet count was performed daily until neutrophil and platelet engraftment, then weekly until Day +30;

Eastern Cooperative Group performance status was examined at the time of hospital discharge, then weekly until Day +30;

Basic serum chemistry panel (sodium, potassium, chloride, glucose, creatinine, bicarbonate, and BUN) daily until neutrophil engraftment;

Full serum chemistry panel (sodium, potassium, chloride, magnesium, bicarbonate, glucose, total protein, albumin, calcium, phosphate, uric acid, BUN, creatinine, CPK, total bilirubin, alkaline phosphatase, LDH, SGOT, and SGPT) will be monitored weekly until Day +30;

Urinalysis (specific gravity, pH, protein, glucose, ketones, nitrite, RBCs, and WBCs) was monitored twice weekly until hospital discharge, then weekly until Day +30; and Concomitant medications was recorded during the entire study period.

A melphalan dose of 200 $g/m^2$ was divided into two separate, consecutive doses of 100 $mg/m^2$ administered on two separate days (Day −3 and Day −2) prior to the patients receiving an autologous stem cell transplantation. For the calculation of body surface area, actual body weight was used for patients who weighed less than or between 100% to 130% of their ideal body weight. Patients who weighed more than 130% of their ideal body weight were dosed based on a body surface area obtained by calculating the patient's adjusted body weight.

Patients were randomly chosen to receive the first melphalan dose of 100 $mg/m^2$ (on Day −3) via either a composition comprising a propylene glycol diluent (i.e., Melphalan HCl Injectable, Bioniche Pharma USA) or a composition comprising a cyclodextrin derivative ($SBE_{6.5}$-β-CD, CAPTISOLe, at a concentration of 125 mM). Patients who randomly received the first melphalan dose of 100 $mg/m^2$ as a composition comprising a cyclodextrin derivative (on Day −3) then received a second melphalan dose of 100 $mg/m^2$ (on Day −2) using the composition comprising a propylene glycol diluent. Conversely, patients who randomly received the first melphalan dose of 100 $mg/m^2$ as a composition comprising a propylene glycol diluent (on Day −3) then received a second melphalan dose of 100 $mg/m^2$ (on Day −2) using the composition comprising a cyclodextrin derivative.

For the composition comprising a cyclodextrin derivative, a dry powder composition containing melphalan as a hydrochloride salt was diluted with normal saline to a melphalan concentration no greater than 0.45 mg/mL and a cyclodextrin concentration of 125 mM. The diluted solution was infused over 60 minutes via a central venous catheter.

The composition comprising a propylene glycol diluent was administered using a cyclodextrin-free composition (Melphalan HC1 Injectable, Bioniche Pharma USA) using the protocol described herein supra.

Following one day of rest after the myeloablative conditioning (Day −1), patients received an autologous graft with a minimum cell dose of $2 \times 10^6$ CD34+ cells/kg of patient body weight (Day 0). Cryopreservation and thawing of the product was consistent with Foundation for the Accreditation of Cellular Therapy standards and local institutional practice. The graft was infused per institutional protocol. Starting on Day +5, G-CSF was be administered at a dose of 5 μg/kg/day until absolute neutrophil count was greater than 500/$mm^3$.

Blood samples for pharmacokinetic evaluation of melphalan were collected after each dose of melphalan and the pharmacokinctic parameters for in vivo melphalan distribution were evaluated. Samples for evaluation of the pharmacokinetic parameters were collected by taking 5 mL venous blood samples immediately prior to melphalan administration and at 0, 10, 20, 30, 60, 90, 120, 180, 240, 360, and 480 minutes following the end of the melphalan infusion. Pharmacokinetic parameters were determined by nonparametric pharmacokinetic data analysis techniques. Pharmacokinetic parameters computed from plasma drug concentration-time data include the following:

$C_{max}$, derived from the individual raw data;
$T_{max}$, derived from the individual raw data;
Apparent terminal first-order elimination rate constant ($k_{el}$);
Apparent elimination $t_{1/2}$;
Area under the plasma concentration-time curve to the last measurable time point ($AUC_{0-t}$), calculated by the trapezoidal rule; and
Area under the plasma concentration-time curve from the last measurable time point extrapolated to infinity ($AUC_{t-\infty}$), determined from the concentration at the last measurable time point divided by the $k_{el}$.

The plasma concentrations and pharmacokinetic parameters were summarized using descriptive statistics. The data from patients 1-3 is shown in the following table.

TABLE

Individual patient melphalan pharmacokinetic parameters after intravenous administration of a melphalan formulation that contained SBE6.5-β-CD and a cyclodextrin-free melphalan formulation (i.e., Melphalan HCl Injectable, Bioniche Pharma USA).

| Patient | Parameter | SBE$_{6.5}$-β-CD (27% w/v) | CD-free formulation | Ratio |
|---|---|---|---|---|
| 1[a] | $C_{max}$ (ng/mL) | 3,230 | 2,160 | 1.50 |
| | $T_{max}$ (min) | 10 | 20 | — |
| | $AUC_{0-t}$ | 259,073 | 202,714 | 1.28 |
| | $AUC_{0-\infty}$ | 264,656 | 208,028 | 1.27 |
| | $\lambda_z$(min$^{-1}$) | 0.0105 | 0.0103 | — |
| | $t_{1/2}$(min) | 65.8 | 67.1 | — |
| 2[b] | $C_{max}$ (ng/mL) | 2,730 | 2,010 | 1.36 |
| | $T_{max}$ (min) | 10 | 10 | — |
| | $AUC_{0-t}$ | 198,051 | 151,456 | 1.31 |
| | $AUC_{0-\infty}$ | 202,728 | 154,130 | 1.32 |
| | $\lambda_z$(min$^{-1}$) | 0.0103 | 0.0113 | — |
| | $t_{1/2}$(min) | 67.4 | 61.6 | — |
| 3[a] | $C_{max}$ (ng/mL) | 4,590 | 2,890 | 1.59 |
| | $T_{max}$ (min) | 10 | 10 | — |
| | $AUC_{0-t}$ | 306,432 | 230,681 | 1.33 |
| | $AUC_{0-\infty}$ | 314,108 | 236,059 | 1.33 |
| | $\lambda_z$(min$^{-1}$) | 0.0101 | 0.0104 | — |
| | $t_{1/2}$(min) | 68.5 | 66.4 | — |

[a]Patients 1 and 3 were administered the SBE$_{6.5}$-β-CD-containing formulation on Day −3 and the CD-free formulation on Day −2.
[b]Patient 2 was administered the CD-free formulation on Day −3 and the SBE$_{6.5}$-β-CD-containing formulation on Day −2.

Figure 6:
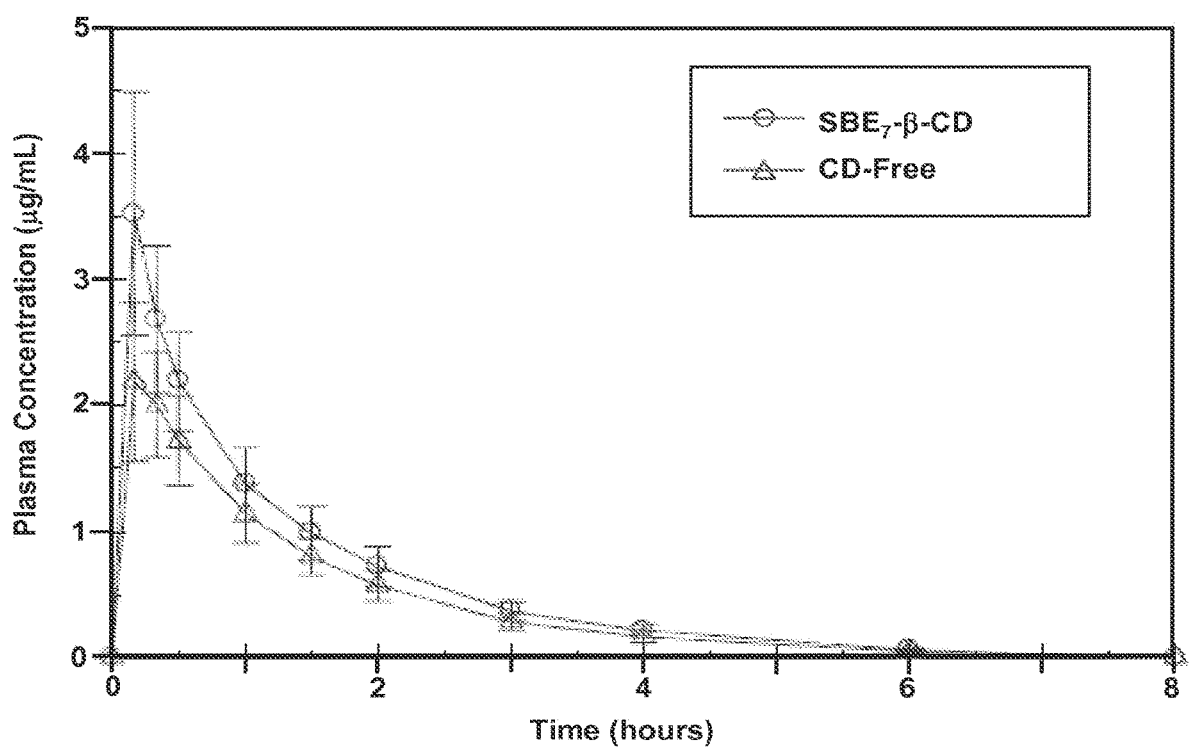
FIG. 6 provides a graphic representation of the mean plasma melphalan concentration in a human patient after intravenous administration of a melphalan formulation containing a cyclodextrin derivative ($SBE_{6.5}$-β-CD) and after intravenous administration of a cyclodextrin-free melphalan formulation (Melphalan HCl Injectable, Bioniche Pharma USA).

FIG. 6, provides a graphic representation of the mean plasma melphalan concentration in a human patient after intravenous administration of a melphalan formulation containing a cyclodextrin derivative (SBE$_{6.5}$-β-CD) and after intravenous administration of a cyclodextrin-free melphalan formulation (Melphalan HCl Injectable, Bioniche Pharma USA). Referring to FIG. 6 and the data in the above table, the in vivo distribution of melphalan administered with a sulfoalkyl ether cyclodextrin derivative provides a nearly 50% increase in the maximum in vivo concentration of melphalan, and approximately a 30% increase in the area under the plasma concentration curves (i.e., for both $AUC_{0-t}$ and $AUC_{0-\infty}$). As shown in the table above, the data for patients 2 and 3 exhibited similar pharmacokinetic results. In view of pharmacokinetic data obtained for these melphalan formulations in the rat model, the enhancement in $C_{max}$ and AUC for the SBE$_{6.5}$-β-CD-containing melphalan formulation in human patients is wholly unexpected.

As noted above, the study is on-going. The primary efficacy end points, which will be based on an intent-to-treat analysis of all patients, will be the rate of myeloablation and the rate neutrophil engraftment. The following definitions will be used for these end points:

Myeloablation will be defined as any of the following:
Absolute neutrophil count less than 0.5×10$^9$/L;
Absolute lymphocyte count less than 0.1×10$^9$/L; or
Platelet count less than 20,000/mm$^3$ or bleeding requiring transfusion.

The first of two consecutive days for which cell counts drop below these cut-off levels will be recorded as the date of myeloablation.

Neutrophil engraftment is defined as absolute neutrophil count greater than 0.5×10$^9$/L on three consecutive daily assessments.

Secondary efficacy end points will be based on the following criteria:

The rate of platelet engraftment, which will be defined as an un-transfused platelet measurement >20,000/mm$^3$ on three consecutive daily assessments;
The time to neutrophil engraftment, which will be defined as the first of three assessments where absolute neutrophil count is greater than 0.5×10$^9$/L;
The time to platelet engraftment, which will be defined as the first of three consecutive daily assessments where un-transfused platelet measurement is greater than 20,000/mm$^3$;
The rate of non-engraftment, which will be defined as a failure to reach an absolute neutrophil count greater than 0.5×10$^9$/L on three consecutive daily assessments by autologous stem cell transplantation Day +100;
The rate of late graft failure or late rejection, which will be defined as development of absolute neutrophil count less than 0.5×10$^9$/L after having engrafted within the first 100 days;
The rate of multiple myeloma response (sCR, CR, VGPR, PR, SD, or PD), which will be defined according to International Working Group criteria at Day +100; and
The rate of treatment-related mortality, which will be defined as death without relapse or progression at Day +100.

The clinical trial is expected to demonstrate that melphalan administered with a cyclodextrin derivative (SBE$_{6.5}$-β-CD) is therapeutically effective and safe for use in subjects for whom a stem cell transplantation has been indicated as conditioning prior to stem cell transplantation.

Example 18

A Phase IIb, multi-center, open-label, non-randomized, efficacy and safety study of melphalan hydrochloride administered by injection using a propylene glycol-free vehicle will be conducted in human multiple myeloma patients who have symptomatic multiple myeloma and qualify for ASCT.

The parameters of the study will be similar to those described in Example 17, except that all patients will be administered a propylene glycol-free melphalan composition (100 mg/m$^2$) on Day −3 and Day −2 using a melphalan composition that includes a cyclodextrin derivative. Otherwise, the inclusion criteria, exclusion criteria, safety criteria, dosing, treatment, and efficacy endpoints will be similar to those described above in Example 17.

Example 19

A pharmaceutical composition comprising mechlorethamine as a hydrochloride salt is prepared by the process described in Example 4, except that mechlorethamine is used in place of melphalan.

Example 20

The liquid pharmaceutical composition provided in the previous example is lyophilized to provide a reconstitutable and/or dilutable dry powder comprising about 50 mg of mechlorethamine as a hydrochloride salt. Glass vials are filled with the solution (10 mL) and placed in trays on a pre-cooled shelf at 5° C. The vials are allowed to thermally equilibrate for about 30 minutes, and are then lyophilized to provide a dry powder in each vial. The vials are back-filled with nitrogen at a pressure of about 400 mTorr, and then sealed.

Example 21

A pharmaceutical composition comprising mechlorethamine as a hydrochloride salt is prepared by the process described in Example 8, except that mechlorethamine is used in place of melphalan.

Example 22

The solution prepared in the previous example is lyophilized to provide a reconstitutable and/or dilutable dry powder comprising mechlorethamine as a hydrochloride salt. For the lyophilization, glass vials are filled with the solution (10 mL) and placed in trays on a pre-cooled shelf at 5° C. The vials are allowed to thermally equilibrate for about 1 hour, and are lyophilized to provide a dry powder in each vial. The vials are back-filled with nitrogen, sealed, packaged, and labeled. The vials are protected from exposure to light during all aspects of the lyophilization, back-filling, sealing, packaging and labeling procedures.

Example 23

A pharmaceutical composition comprising cyclophosphamide as a hydrochloride salt is prepared by the process described in Example 4, except that cyclophosphamide is used in place of melphalan.

Example 24

The liquid pharmaceutical composition provided in the previous example is lyophilized to provide a reconstitutable and/or dilutable dry powder comprising about 50 mg of cyclophosphamide as a hydrochloride salt. Glass vials are filled with the solution (10 mL) and placed in trays on a pre-cooled shelf at 5° C. The vials are allowed to thermally equilibrate for about 30 minutes, and are then lyophilized to provide a dry powder in each vial. The vials are back-filled with nitrogen at a pressure of about 400 mTorr, and then sealed.

Example 25

A pharmaceutical composition comprising cyclophosphamide as a hydrochloride salt is prepared by the process described in Example 8, except that cyclophosphamide is used in place of melphalan.

Example 26

The solution prepared in Example the previous example is lyophilized to provide a reconstitutable and/or dilutable dry powder comprising cyclophosphamide as a hydrochloride salt. For the lyophilization, glass vials are filled with the solution (10 mL) and placed in trays on a pre-cooled shelf at 5° C. The vials are allowed to thermally equilibrate for about 1 hour, and are lyophilized to provide a dry powder in each vial. The vials are back-filled with nitrogen, sealed, packaged, and labeled. The vials are protected from exposure to light during all aspects of the lyophilization, back-filling, sealing, packaging and labeling procedures.

Example 27

A pharmaceutical composition comprising ifosfamide as a hydrochloride salt is prepared by the process described in Example 4, except that ifosfamide is used in place of melphalan.

Example 28

The liquid pharmaceutical composition provided in the previous example is lyophilized to provide a reconstitutable and/or dilutable dry powder comprising about 50 mg of ifosfamide as a hydrochloride salt. Glass vials are filled with the solution (10 mL) and placed in trays on a pre-cooled shelf at 5° C. The vials are allowed to thermally equilibrate for about 30 minutes, and are then lyophilized to provide a dry powder in each vial. The vials are back-filled with nitrogen at a pressure of about 400 mTorr, and then sealed.

Example 29

A pharmaceutical composition comprising ifosfamide as a hydrochloride salt is prepared by the process described in Example 8, except that ifosfamide is used in place of melphalan.

Example 30

The solution prepared in Example the previous example is lyophilized to provide a reconstitutable and/or dilutable dry powder comprising ifosfamide as a hydrochloride salt. For the lyophilization, glass vials are filled with the solution (10 mL) and placed in trays on a pre-cooled shelf at 5° C. The vials are allowed to thermally equilibrate for about 1 hour, and are lyophilized to provide a dry powder in each vial. The vials are back-filled with nitrogen, sealed, packaged, and labeled. The vials are protected from exposure to light during all aspects of the lyophilization, back-filling, sealing, packaging and labeling procedures.

Example 31

A pharmaceutical composition comprising bendamustine as a hydrochloride salt is prepared by the process described in Example 4, except that bendamustine is used in place of melphalan.

Example 32

The liquid pharmaceutical composition provided in the previous example is lyophilized to provide a reconstitutable and/or dilutable dry powder comprising about 50 mg of bendamustine as a hydrochloride salt. Glass vials are filled with the solution (10 mL) and placed in trays on a pre-cooled shelf at 5° C. The vials are allowed to thermally equilibrate for about 30 minutes, and are then lyophilized to provide a dry powder in each vial. The vials are back-filled with nitrogen at a pressure of about 400 mTorr, and then sealed.

Example 33

A pharmaceutical composition comprising bendamustine as a hydrochloride salt is prepared by the process described in Example 8, except that bendamustine is used in place of melphalan.

Example 34

The solution prepared in Example the previous example is lyophilized to provide a reconstitutable and/or dilutable dry powder comprising bendamustine as a hydrochloride salt. For the lyophilization, glass vials are filled with the solution (10 mL) and placed in trays on a pre-cooled shelf at 5° C. The vials are allowed to thermally equilibrate for about 1 hour, and are lyophilized to provide a dry powder in each vial. The vials are back-filled with nitrogen, sealed, packaged, and labeled. The vials are protected from exposure to light during all aspects of the lyophilization, back-filling, sealing, packaging and labeling procedures.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An injectable aqueous pharmaceutical formulation comprising 8.5 mL of an aqueous solution at a pH of 5, said solution consisting of 9 g/L sodium chloride, a sulfobutyl ether-β-cyclodextrin, and 5 mg/mL melphalan, wherein said sulfobutyl ether-β-cyclodextrin and said melphalan are present in a weight ratio of 54:1; and
wherein said aqueous pharmaceutical formulation is stable at room temperature for at least one hour, as compared to a cyclodextrin-free reference melphalan standard.

2. The aqueous formulation of claim 1, wherein less than 2% by weight of said melphalan is degraded after 5 hours at room temperature as compared to the amount of melphalan present before holding said formulation at room temperature for 5 hours.

3. The aqueous formulation of claim 1, wherein less than 4% by weight of said melphalan is degraded when said formulation is held at room temperature for 10 hours as compared to the amount of melphalan present before holding said formulation at room temperature for 10 hours.

4. An injectable aqueous pharmaceutical formulation comprising 10 mL of an aqueous solution with a pH of 5, said formulation consisting of a sulfobutyl ether-β-cyclodextrin and 0.45 mg/mL melphalan;
wherein said sulfobutyl ether-β-cyclodextrin and said melphalan are present in a weight ratio of at least 54:1; and
wherein said aqueous pharmaceutical formulation is stable at room temperature for at least 4 hours, as compared to a cyclodextrin-free reference melphalan standard.

5. The aqueous formulation of claim 4, wherein less than 2% by weight of said melphalan is degraded when said formulation is held at room temperature for 5 hours as compared to the amount of melphalan present before holding said formulation at room temperature for 5 hours.

6. The aqueous formulation of claim 4, wherein less than 4% by weight of said melphalan is degraded when said formulation is held at room temperature for 10 hours as compared to the amount of melphalan present before holding said formulation at room temperature for 10 hours.

7. An injectable aqueous pharmaceutical formulation comprising 8.5 mL of an aqueous solution at a pH of 5, said solution consisting of at least one of an antioxidant, preservative, or buffer, 9 g/L sodium chloride, a sulfobutyl ether-β-cyclodextrin, and 5 mg/mL melphalan, wherein said sulfobutyl ether-β-cyclodextrin and said melphalan are present in a weight ratio of 54:1;
wherein said aqueous pharmaceutical formulation is stable at room temperature for at least one hour, as compared to a cyclodextrin-free reference melphalan standard.

8. The aqueous formulation of claim 1 or 4 or 7, wherein administration of the formulation provides up to a 30% increase in the area under the melphalan plasma concentration curve as compared to administration of a cyclodextrin-free melphalan formulation.

9. An injectable aqueous pharmaceutical formulation consisting of 5 mg/mL melphalan, sulfobutyl ether-β-cyclodextrin and 9 g/L sodium chloride; wherein said sulfobutyl ether-β-cyclodextrin and said melphalan are present in a weight ratio of 54:1;
wherein the aqueous pharmaceutical formulation has a pH of 5;
wherein said aqueous pharmaceutical formulation is stable at room temperature for at least one hour, as compared to a cyclodextrin-free reference melphalan standard; and
further wherein administering the formulation provides a melphalan $AUC_{0-t}$ in a subject that is at least 20% greater than a melphalan $AUC_{0-t}$ provided by a melphalan formulation containing an equivalent dose of melphalan and lacking the cyclodextrin derivative.

10. An injectable aqueous pharmaceutical formulation consisting of 0.45 mg/mL melphalan, sulfobutyl ether-β-cyclodextrin and 9 g/L sodium chloride; wherein said sulfobutyl ether-β-cyclodextrin and said melphalan are present in a weight ratio of at least 54:1;
wherein the aqueous pharmaceutical formulation has a pH of 5;
wherein said aqueous pharmaceutical formulation is stable at room temperature for at least 4 hours, as compared to a cyclodextrin-free reference melphalan standard; and
further wherein administering the formulation provides a melphalan $AUC_{0-t}$ in a subject that is at least 20% greater than a melphalan $AUC_{0-t}$ provided by a melphalan formulation containing an equivalent dose of melphalan and lacking the cyclodextrin derivative.

* * * * *